US005773476A

United States Patent [19]

Chen et al.

[11] Patent Number: 5,773,476
[45] Date of Patent: Jun. 30, 1998

[54] METHODS AND COMPOSITIONS FOR INHIBITING CELL PROLIFERATIVE DISORDERS

[75] Inventors: Hui Chen, Palo Alto, Calif.; Aviv Gazit; Alexander Levitzki, both of Jerusalem, Israel; Klaus Peter Hirth, San Francisco, Calif.; Elaina Mann, Alameda, Calif.; Laura K. Shawver, San Francisco, Calif.; Jianming Tsai, San Francisco, Calif.; Peng Cho Tang, Moraga, Calif.

[73] Assignees: Sugen, Inc., Redwood City; Yissum Research and Development Company of the Hebrew University of Jerusalem, Jerusalem, both of Israel

[21] Appl. No.: 486,775

[22] Filed: Jun. 7, 1995

Related U.S. Application Data

[63] Continuation of Ser. No. 399,967, Mar. 7, 1995, which is a continuation-in-part of Ser. No. 207,933, Mar. 7, 1994, abandoned.

[51] Int. Cl.$^6$ .................................................. A01N 37/18
[52] U.S. Cl. ........................ 514/620; 514/618; 514/619; 564/162; 564/164; 564/165; 564/167; 564/168; 564/170
[58] Field of Search ..................................... 558/388, 393, 558/395, 401–402, 403, 404, 408, 410, 392; 564/161, 162, 163, 164, 165, 167, 168, 170, 171, 174; 514/516, 521, 523

[56] References Cited

U.S. PATENT DOCUMENTS 5,217,999  6/1993  Levitzki et al. ........................ 514/613

FOREIGN PATENT DOCUMENTS

| 3101093 | 1/1993 | Australia . |
| 2069857 | 5/1992 | Canada . |
| 0520722 | 6/1992 | European Pat. Off. . |
| 0537742 | 4/1993 | European Pat. Off. . |
| 0566226 | 10/1993 | European Pat. Off. . |
| 2240104 | 1/1991 | United Kingdom . |
| 9202444 | 2/1992 | WIPO . |
| 9203736 | 6/1992 | WIPO . |
| 9220642 | 11/1992 | WIPO . |
| 9221641 | 12/1992 | WIPO . |
| WO 94/24095 | 10/1994 | WIPO . |

OTHER PUBLICATIONS

G. Kaur, A. Gazit, A. Levitzki, E. Stowe, D. Cooney, E. Sausville, Anti–Cancer Drugs 1994, vol. 5, pp. 213–222, Mar. 1994.

Aaronson, S., "Growth Factors and Cancer," *Science* 254:1146–1153 (1991).

Affleck et al., *Proc. Annu. Meeting American Associate Cancer Research* 34:A2298 (1993).

Anafi et al., "Selective Interactions of Transforming and Normal abl Proteins with ATP, Tyrosine–Copolymer Substrates, and Tyrphostins," *J. Bio. Chem.* 267:4518–4523 (1992).

Andrews et al. (American Veterinary Medicine Association Panel on Euthanasia), "1993 Report of the AVMA Panel on Authanasia," *J. American Veterinary Medicine Association* 202(2):229–249 (1993).

Baselga et al., "Antitumor Effects of Doxorubicin in Combination With Anti–epidermal Growth Factor Receptor Monoclonal Antibodies," *J. of Natl. Cancer Institute* 85(16):1327–1333 (1993).

(List continued on next page.)

*Primary Examiner*—Charles T. Jordan
*Assistant Examiner*—John R. Hardee
*Attorney, Agent, or Firm*—Lyon & Lyon LLP

[57] ABSTRACT

The present invention concerns compounds and their use to inhibit the activity of a receptor tyrosine kinase. The invention is preferably used to treat cell proliferative disorders such as cancers charcterized by over-activity or inappropriate activity HER2 or EGFR.

17 Claims, 12 Drawing Sheets

OTHER PUBLICATIONS

Bilder et al., "Tyrphostins inhibit PDGF–induced DNA synthesis and associated early events in smooth muscle cells," *Am. J. Physiol.* 260 (Cell Physiol.29):C721–C730 (1991).

Birchall et al., "Compositions for killing internal parasites containing 3–teri–alkyl–4–hydroxy–5–halobenzylidene–malononitriles," *Chemical Abstracts* 88:535 (1978).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Caraglia et al., "Cytosine arabinoside increases the binding of $^{125}$I–labelled epidermal growth factor and $^{125}$I–transferrin and enhances the in vitro targeting of human tumour cells with anti–(growth factor receptor)mAb," *Cancer Immunol. Immunother.* 37:150–156 (1993).

Carboni et al., "Cyanocarbon Chemistry. XI. Malononitrile Dimer," *J. Am. Chem. Soc.* 80:2838–2840 (1958).

Lee and Salemnick, "Purine N–Oxides, LXII. 2,4–Dioxopyrido[2,3–d]pyrimidine N–Oxides," *J. Org. Chem.* 40(24):3608–3610 (1975).

Levitzki, A., "Tyrphostins—Potential Antiproliferative Agents and Novel Molecular Tools," *Biochem. Pharm.* 40(5):913–918 (1990).

Ley and Seng, "Synthesen unter Verwendung von Benzofuroxan," *Synthesis* 1975:415–422 (1975).

Lyall et al., "Tyrphostins Inhibit Epidermal Growth Factor (EGF)–Receptor Tyrosine Kinase Activity in Living Cells and EGF–stimulated Cell Proliferation," *J. Bio. Chem.* 264:14503–14509 (1989).

Marshall, E., "Search for a Killer: Focus Shifts from Fat to Hormones," *Science* 259:618–621 (1993).

Mosmann, "Rapid Colorimetric Assay for Cellular Growth and Survival: Application to Proliferation and Cytotoxicity Assays," *J. Immunol. Methods* 65:55–63 (1983).

Mitus and Rosenthal, "Ch. 30—Adult Leukemias," *Textbook of Clincal Oncology*, Holleb, Fink and Murphy eds., pp. 410–432.

Ohmichi et al., "The Tyrosine Kinase Inhibitor Tyrphostin Blocks the Cellular Actions of Nerve Growth Factor," *Biochemistry* 32:4650–4658 (1993).

O'Rourke and Kalter, "Ch. 28—Leukemia" in *Clinical Oncology*, Weiss et al. eds, Appleton & Lange, Norwalk Conn., pp. 272–283 (1993).

Osborne et al., "Effect of Estrogens and Antiestrogens on Growth of Human Breast Cancer Cells in Athymic Nude Mice," *Cancer Research* 45:584–590 (1985).

Osherov et al., "Selective Inhibition of the EGF and Neu receptors by Tyrophostins," *J. Cell Biochem.* S17A:237 (1993).

Osherov et al., "Selective Inhibition of the Epidermal Growth Factor and HER2/Neu Receptors by Tyrphostins," *J. Bio. Chem.* 268:11134–11142 (1993).

Ozzello and Sordat, "Behavior of Tumors Produced by Transplantation of Human Mammary Cell Lines in Athymic Nude Mice," *Eur. J. Cancer* 16:553–559 (1980).

Pawson and Schlessinger, "SH2 and SH3 domains," *Current Biology* 3(7):434–441 (1993).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Pigott et al., "Expression of epidermal growth factor receptor in human glioblastoma multiforme," *Brit. J. of Neurosurgery* 7:261–265 (1993).

Plowman et al., "Heregulin induces tyrosine phosphorylation of HER4/p180$^{erbB4}$," *Nature* 366:473–475 (1993).

Pui and Rivera, "Ch. 31—Childhood Leukemias," *Textbook of Clincal Oncology*, Holleb, Fink and Murphy eds., pp. 433–452.

Reddy et al., "Inhibition of Breast Cancer Cell Growth in Vitro by a Tyrosine Kinase Inhibitor," *Cancer Research* 52:3636–3641 (1992).

Rendu et al., "Inhibition of Platelet Activation by Tyrosine Kinase Inhibitors," *Biochem. Pharm.* 44(5):881–888 (1992).

Rusch et al., "Differential Expression of the Epidermal Growth Factor Receptor and Its Lgands in Primary Non–Small Cell Lung Cancers and Adjacent Benign Lung," *Cancer Research* 53:2379–2385 (1993).

Rubens, "Improving Treatment for Advanced Breast Cancer," *Cancer Surveys* 18:199–209 (1993).

Rygaard and Povlsen, "Heterotransplantation of a Human Malignant Tumour to 'Nude' Mice," *Acta path. microbiol. scand.* 77:758–760 (1969).

Samanta, "Ligand and p185$^{c-neu}$ density govern receptor interactions and tyrosine kinase activation," *Proc. natl. Acad. Sci. USA* 91:1711–1715 (1994).

Sammes et al., "α–Cyano–sulphonyl Chlorides: Their Preparation and Reactions with Amines, Alcohols and Enamines," *J. Chem. Soc.* pp. 2151–2155 (1971).

Sarup, "Characterization of an Anti–p185$^{HER2}$ Monoclonal Antibody that Stimulates Receptor Function and Inhibits Tumor Cell Growth," *Growth Regulation* 1:72–82 (1991).

Schlessinger, J., "Signal transduction by allosteric receptor oligomerization," *Trends Biochem. Sci.* 13:443–447 (1988).

Schlessinger and Ullrich, "Growth Factor Signalling by Receptor Tyrosine Kinases," *Neuron* 9:383–391 (1992).

Schornagel et al., "Synthesis and Evaluation of 2,4–Diaminoquinazoline Antifolates with Activity Against Methotrexate–Resistant Human Tumor Cells," *Biochem. Pharm.* 33(20):3251–3255 (1984).

Scott et al., "p185$^{HER2}$ Signal Transduction in Breast Cancer Cells," *J. Bio. Chem.* 266(22):14300–14305 (1991).

Seibert et al., "Clonal Variation of MCF–7 Breast Cancer Cells in Vitro and in Athymic Nude Mice," *Cancer Research* 43:2223–2239 (1983).

Shafie and Grantham, "Role of Hormones in Growth and Regression of Human Breast Cancer Cells (MCF–7) Transplanted into Athymic Nude Mice," *J. Natl Cancer Institute* 67(1):51–56 (1981).

Shepard, "Monoclonal Antibody Therapy of Human Cancer: taking the HER2 Protooncogene to the Clinic," *Journal of Clinical Immunology* 11:117–126 (1991).

Skehan et al., "New Colorimetric Cytotoxicity Assay for Anticancer–Drug Screening," *J. Natl. Cancer Inst.* 82:1107–1112 (1990).

Slamon et al., "Human Breast Cancer: Correlation of Relapse and Survival with Amplification of the HEr–2/neu Oncogene," *Science* 235:177–185 (1987).

Sliwkowski et al., "Coexpression of erbB2 and erbB3 Proteins Reconstitutes a High Affinity Receptor for Heregulin," *J. Biol. Chem.* 269:14661–14665 (1994).

Stein et al., "The SH2 domain protein GRB–7 is co–amplified, overexpressed and in a tight complex with HER2 in breast cancer," *EMBO Journal* 13(6):1331–1340 (1994).

Ullrich and Schlessinger, "Signal Transduction by Receptors with Tyrosine Kinase Activity," *Cell* 61:203–212 (1990).

Wada et al., "Anti–receptor antibodies reverse the phenotype of cells transformed by two interacting proto–oncogene encoded receptor proteins," *Oncogene* 5:489–495 (1990).

Wada, "Intermolecular Association of the p185$^{neu}$ Protein and EGF Receptor Modulates EGF Receptor Function," *Cell* 61:1339–1347 (1990).

Warri et al., "Estrogen Suppression of erbB2 Expression is Associated with Increased Growth Rate of ZR–75–I Human Breast Cancer Cells In Vitro and in Nude Mice," *Int. J. Cancer* 49:616–623 (1991).

Yaish et al., "Blocking of EGF–Dependent Cell Proliferation by EGF Receptor Kinase Inhibitors," *Science* 242:933–935 (1988).

Yarden, "Growth factor receptor tyrosine kinase," *Ann. Rev. Biochem.* 57:443–478 (1988).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

Zeillinger et al., "EGF–R and Steroid Receptors in Breast Cancer: A Comparison with Tumor Grading, Tumor Size, Lymph Node Involvement, and Agen," *Clin. Biochem.* 26:221–227 (1993).

Carraway and Cantley, "A Neu Acquaintance for ErbB3 and ErbB4: A Role for Receptor Hereodimerization in Growth Signaling," *Cell* 78:5–8 (1994).

Carraway et al., "The erbB3 Gene Product Is a Receptor for Heregulin," *J. Biol. Chem.* 269:14303–14306 (1994).

Dati et al., "Inhibition of c–erbB–2 oncogene expression by estrogens in human breast cancer cells," *Oncogene* 5:1001–1006 (1990).

Decker and Lohmann–Matthes, "A quick and simple method for the quantitation of lactate dehydrogenase release in measurements of cellular cytotoxicity and tumor necrosis factor (TNF) activity," *J. Immunol. Methods* 15:61–69 (1988).

Dougall et al., "The neu–oncogene: signal transduction pathways, transformation mechanisms evolving employees" *Oncogene* 9:2109–2123 (1994).

Ferris et al., "Synthesis of Zuinazoline Nucleosides from Ribose and Anthranilonitrile. Application of Phase–Transfer Catalysis in Nucleoside Synthesis," *J. Org. Chem.* 44(2):173–178 (1979).

Floege et al., "Factors involved in the regulation of mesangial cell proliferation in vitro and in vivo," *Kidney International* 43S:47–54 (1993).

Gazit et al., "Tyrphostins. 1. Synthesis and Biological Activity of Protein Tyrosine Kinase Inhibitors," *J. Med. Chem.* 32:2344–2352 (1989).

Gazit et al., "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* 34:1896–1907 (1991).

Gazit et al., "Tyrphostins. 3. Structure–Activity Relationship Studies of a α–Substituted Benzylidenemalononitrile 5–S–Aryltyrphostins" *J. Med. Chem.* 36:3556–3564 (1993).

Gottardis et al., "Estradiol–Stimulated Growth of MCF–7 Tumors Implanted in Athymic Mice: A Model to Study the Tumoristatic Action of Tamoxifen," *J. Steroid Biochem.* 30(1–6):331–314 (1988).

Hale et al., "Prognostic value of epidermal growth factor receptor expression in cervical carcinoma," *J. Clin. Pathol.* 46:149–153 (1993).

Harris et al., "Breast Cancer (First of Three Parts)," *New England J. of Medicine* 327(5):319–328 (1992).

Hoekstra et al., "Differential effects of steurosporine and tyrphostins on receptor tyrosine kinase autophosphorylation and peptide substrate phosphorylation," *Experimental Therapeutics* from 84th Annual Meeting of American Association for Cancer Research, vol. 34, #2455 (1993).

Honegger et al., "Point Mutation at the ATP Binding Site of EGF Receptor Abolishes Protein–Tyrosine Kinase Activity and Alters Cellular Routing," *Cell* 5:199–209 (1987).

Hudziak et al., "p185$^{HER2}$ Monoclonal Antibody Has Antiproliferative Effects In Vitro and Sensitizes Human Breast Tumor Cells to Tumor Necrosis Factor," *Molecular and Cellular Biology* 9:1165–1172 (1989).

Issidorides and Haddadin, "Benzofurazan Oxide. II. Reactions with Enolate Anions," *J. Org. Chem.* 31:4067–4068 (1966).

Karameris et al., "Expression of Epidermal Growth Factor (EGF) and Epidermal Growth Factor Receptor (EGFR) in Gastric and Colorectal Carcinomas, An Immunohistological Study of 63 Cases," *Path. Res. Pract.* 189:133–137 (1993).

Koenders et al., "Epidermal growth factor receptor and prognosis in human breast cancer: a prospective study," *Breast Cancer Research and Treatment* 25:21–27 (1993).

Korzeniewski and Callewaert, "An Enzyme–Release Assay for Natural Cytotoxicity[1]," *J. Immunol. Methods* 64:313 (1983).

GROUP 1

GROUP 1

GROUP 1

M17

M18

M19

GROUP 1

M20

M21

M22

GROUP 1

M23

M24

M25

GROUP 1

M26

M27

M28

GROUP 1

M29

M30

M31

GROUP 1

M32

M33

M34

GROUP 1

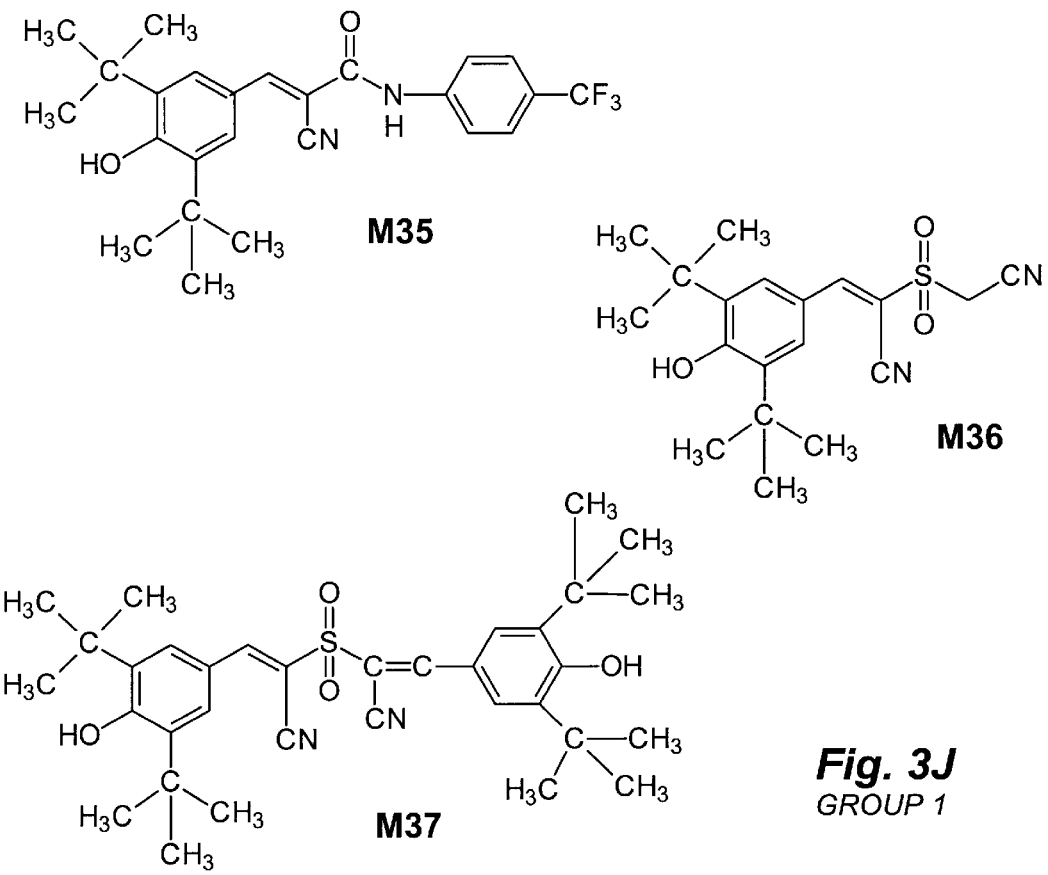
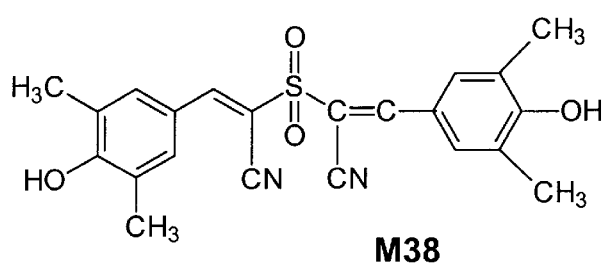
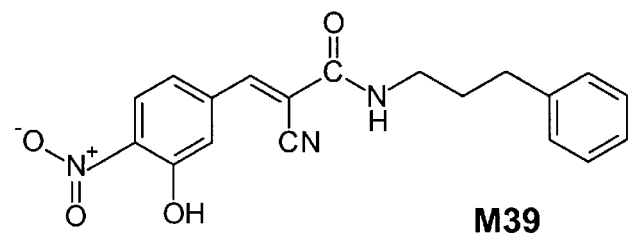
Fig. 3J GROUP 1
Fig. 3K GROUP 1

M40

M41

M42

M43

M44

M45

GROUP 2

GROUP 2

GROUP 2

GROUP 2

GROUP 2

GROUP 3

GROUP 3

GROUP 4

OTHERS

R9

R13

R14

R15

OTHERS

N29

OTHERS

5,773,476

METHODS AND COMPOSITIONS FOR INHIBITING CELL PROLIFERATIVE DISORDERS

RELATED APPLICATIONS

The present application is a continuation of U.S. patent application Serial No. 08/399,967, filed Mar. 7, 1995 which is a continuation-in-part of Chen et al., entitled "METHODS AND COMPOSITIONS FOR INHIBITING CELL PROLIFERATION DISORDERS," U.S. Ser. No. 08/207,933, filed Mar. 7, 1994, now abandoned, the entire contents of which, including the drawings, are hereby incorporated into the present application.

FIELD OF THE INVENTION

The present invention relates to methods and compositions for inhibiting cell proliferative disorders. The described methods are particularly useful for inhibiting cell proliferative disorders characterized by over-activity and/or inappropriate activity of a receptor tyrosine kinase.

BACKGROUND OF THE INVENTION

Receptor tyrosine kinases belong to a family of transmembrane proteins and have been implicated in cellular signaling pathways. The predominant biological activity of some receptor tyrosine kinases is the stimulation of cell growth and proliferation, while other receptor tyrosine kinases are involved in arresting growth and promoting differentiation. In some instances, a single tyrosine kinase can inhibit, or stimulate, cell proliferation depending on the cellular environment in which it is expressed. (Schlessinger, J. and Ullrich, A., *Neuron*, 9(3) : 383–391, 1992.)

Receptor tyrosine kinases contain at least seven structural variants. All of the receptor tyrosine kinases are composed of at least three domains: an extracellular glycosylated ligand binding domain, a transmembrane domain and a cytoplasmic catalytic domain that can phosphorylate tyrosine residues. Ligand binding to membrane-bound receptors induces the formation of receptor dimers and allosteric changes that activate the intracellular kinase domains and result in the self-phosphorylation (autophosphorylation and/or transphosphorylation) of the receptor on tyrosine residues.

Receptor phosphorylation stimulates a physical association of the activated receptor with target molecules. Some of the target molecules are in turn phosphorylated, which transmits the signal to the cytoplasm. For example, phosphorylation of phospholipase C-$\lambda$ activates this target molecule to hydrolyze phosphatidylinositol 4,5-bisphosphate, generating two secondary signal transducing molecules: inositol triphosphate, which causes release of stored intracellular calcium, and diacylglycerol, which is the endogenous activator of a serine/threonine kinase, protein kinase C. Other target molecules are not phosphorylated, but assist in signal transmission by acting as docking or adapter molecules for secondary signal transducer proteins. For example, receptor phosphorylation and the subsequent allosteric changes in the receptor recruit the Grb-2/ SOS complex to the catalytic domain of the receptor where its proximity to the membrane allows it to activate ras (reviewed in Schlessinger, J. and Ullrich, A., *Neuron*, supra).

The secondary signal transducer molecules generated by activated receptors result in a signal cascade that regulates cell functions such as cell division or differentiation. Reviews describing intracellular signal transduction include Aaronson, S. A., *Science*, 254:1146–1153, 1991; Schlessinger, J. *Trends Biochem. Sci.*, 13:443–447, 1988; and Ullrich, A., and Schlessinger, J., *Cell*, 61:203–212, 1990.

Various cell proliferative disorders have been associated with defects in different signaling pathways mediated by receptor tyrosine kinases. According to Aaronson, S.A., supra:

Signaling pathways that mediate the normal functions of gr,owth factors are commonly subverted in cancer.

Examples of specific receptor tyrosine kinases associated with cell proliferative disorders include, platelet derived growth factor receptor (PDGFR), epidermal growth factor receptor (EGFR), and HER2. The gene encoding HER2 (her-2) is also referred to as neu, and c-erbB-2 (Slamon, D. J., et al., *Science*, 235:177–182, 1987).

HER2/ neu gene amplification has been linked by some investigators to neoplastic transformation. For example Slamon et al., supra, (hereby incorporated by reference herein) asserts:

The Her-2/ neu oncogene is a member of the erB-like oncogene family, and is related to but distinct from the epidermal growth factor receptor. The gene has been shown to be amplified in human breast cancer cells.

According to Scott et al., supra, (hereby incorporated by reference herein):

Amplification and/or overexpression of HER2/ neu has been detected in gastrointestinal, non-small cell lung, and ovarian adenocarcinomas and occurs in a significant fraction of primary human breast cancers where it correlates with regionally advanced disease, increased probability of tumor recurrence, and reduced patient survival. (Citations omitted).

Publications discussing EGFR and cancer include Zeillinger et al., *Clin. Biochem.* 26:221–227, 1993; where it is asserted:

Increased expression of this receptor [EGFR] has been found in various malignancies. In carcinomas of the cervix, ovaries, esophagus, and stomach, positive EGF-R status is definitely associated with the aggressiveness of the tumor.

With regard to breast cancer the importance attached to the determination of EGF-R has been confirmed by reports by several groups on the positive correlation between EGF-R and relapse-free interval, as well as overall survival. (Citations omitted.)

Other references discussing cancer and EGFR include Karameris et al., *Path. Res. Pract*. 189:133–137, 1993; Hale et al., *J. Clin. Pathol* 46:149–153, 1993; Caraglia et al., *Cancer Immunol Immunother* 37:150–156, 1993; and Koenders et al., *Breast Cancer Research and Treatment* 25:21–27, 1993). (These references, which are not admitted to be prior art, are hereby incorporated by reference herein.)

Compounds able to inhibit the activity of receptor tyrosine kinases have been mentioned in various publications. For example, Gazit et al., *J. Med. Chem*. 34:1896–1907 (1991), examined the receptor tyrosine kinase inhibitory effect of different tyrphostins. According to Gazit:

Among the novel tyrphostins examined we found inhibitors which discriminate between the highly homologous EGF receptor kinase (HER1) and ErbB2/ neu kinase (HER2) . These findings may lead to selective tyrosine kinase blockers for the treatment of diseases in which ErbB2/ neu is involved.

In a later publication Gazit et al., *J. Med. Chem*. 36:3556–3564 (1993) (not admitted to be prior art) describe tyrphostins having a S-aryl substituent in the 5 position. According to Gazit:

We find that these compounds are potent blockers of EGFR kinase and its homolog HER-2 kinase.

Interestingly, we find that certain S-aryltyrphostins discriminate between EGFR and HER-2 kinase in favor of the HER-2 kinase domain by almost 2 orders of magnitude. When examined in intact cells it was found that these selective S-aryltyrphostins are equipotent in inhibiting EGF dependent proliferation of NIH 3T3 harboring either the EGF receptor or the chimera EGF/neu HER1-2.

OSherov et al., *Journal of Biological Chemistry* 268:11134, 1993 (not admitted to be prior art), mentions the development of two groups of tyrphostins:

one is highly selective in inhibiting HER1 [EGF] as compared with HER2 kinase activity, and the other is highly selective in inhibiting HER2 activity compared with HER1 kinase activity.

SUMMARY OF THE INVENTION

The present invention concerns methods and compounds which can be used to inhibit EGFR and/or HER2 activity, preferably HER2 activity. The described methods and compositions are particularly useful for treating cell proliferative disorders, such as cancers characterized by over-activity or inappropriate activity of HER2 or EGFR.

Groups of compounds able to inhibit HER2, and groups of compounds able to inhibit EGFR are described herein (See, FIG. 1). Also described, are exemplary compounds belonging to different groups, and guidelines which can be used to obtain additional compounds belonging to the different groups.

In addition to use as a therapeutic additional uses of the described compounds including use for in vitro studies to determine the mechanism of action of receptor tyrosine kinases, preferably HER2 or EGFR; use as lead compounds to design and screen for additional compounds able to effect receptor tyrosine kinase activity, preferably inhibit HER2 or EGFR, activity; and use to help diagnose the role of a receptor tyrosine kinase in a cell proliferative disorder. For example using standard assays, the active site of the kinase acted upon by any one of the compounds described herein may be determined, and other compounds active at the same site determined.

"Cell proliferative disorders" refer to disorders wherein unwanted cell proliferation of one or more subset(s) of cells in a multicellular organism occurs, resulting in harm (e,g., discomfort or decreased life expectancy) to the multicellular organism. Cell proliferative disorders can occur in different types of animals and in humans. Cell proliferative disorders include cancers, blood vessel proliferative disorders, and fibrotic disorders.

A particular disorder is considered to be "driven" or caused by a particular receptor tyrosine kinase if the disorder is characterized by over-activity, or inappropriate activity, of the kinase and a compound which can inhibit one or more receptor tyrosine kinase activities exerts a therapeutic effect when administered to a patient having the disorder.

A "therapeutic effect" generally refers to either the inhibition, to some extent, of growth of cells causing or contributing to a cell proliferative disorder; or the inhibition, to some extent, of the production of factors (e.g., growth factors) causing or contributing to a cell proliferative disorder. A therapeutic effect relieves to some extent one or more of the symptoms of a cell proliferative disorder. In reference to the treatment of a cancer, a therapeutic effect refers to one or more of the following: 1) reduction in the number of cancer cells; 2) reduction in tumor size; 3) inhibition (i.e., slowing to some extent, preferably stopping) of cancer cell infiltration into peripheral organs; 3) inhibition (i.e., slowing to some extent, preferably stopping) of tumor metastasis; 4) inhibition, to some extent, of tumor growth; and/or 5) relieving to some extent one or more of the symptoms associated with the disorder. In reference to the treatment of a cell proliferative disorder other than a cancer, a therapeutic effect refers to either: 1) the inhibition, to some extent, of the growth of cells causing the disorder; 2) the inhibition, to some extent, of the production of factors (e.g., growth factors) causing the disorder; and/or 3) relieving to some extent one or more of the symptoms associated with the disorder.

When used as a therapeutic the compounds described herein are preferably administered with a physiologically acceptable carrier. A physiologically acceptable carrier is a formulation to which the compound can be added to dissolve it or otherwise facilitate its administration. Examples of physiologically acceptable carriers include water, saline, physiologically buffered saline, cyclodextrins and PBTE:D5W (described below). Hydrophobic compounds are preferably administered using a carrier such as PBTE:D5W. An important factor in choosing an appropriate physiologically acceptable carrier is choosing a carrier in which the compound remains active or the combination of the carrier and the compound produces an active compound. The compound may also be administered in a continuous fashion using a slow release formulation or a pump to maintain a constant or varying drug level in a patient.

Thus, a first aspect of the present invention describes a class of receptor tyrosine kinase inhibitor compositions. By an "inhibitor" of a receptor tyrosine kinase is meant that the compound reduces to some extent one or more activities of HER2, EGFR and/or PDGFR. Preferably, tyrosine kinase inhibitors can significantly inhibit the activity of HER2, EGFR and/or PDGFR. By "significantly inhibit" is meant the compound has an $IC_{50}$ less than 50 $\mu M$ in an assay described in the examples below. The compositions are made up of a compound having the chemical formula:

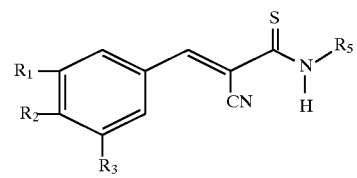

where $R_1$, $R_2$, and $R_3$, is each independently selected from the group consisting of alkyl, alkenyl, alkynyl, lkoxy, alkylaryl, OH, amine, thioether, SH, halogen, hydrogen, $NO_2$ and $NH_2$; and $R_5$, is an alkylaryl comprising an alkyl group, and an aryl group having the following structure:

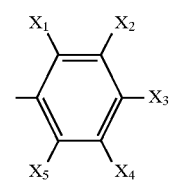

where $X_1$, $X_2$, $X_3$, $X_4$, and $X_5$, is each independently selected from the group consisting of hydrogen, halogen, alkyl, alkoxy, OH, trihalomethyl, and $NO_2$; preferably hydrogen, halogen, alkyl, trihalomethyl, and $NO_2$.

Another aspect of the present invention describes a second class of receptor tyrosine kinase inhibitor compositions. These compositions are made up a compound having the chemical formula:

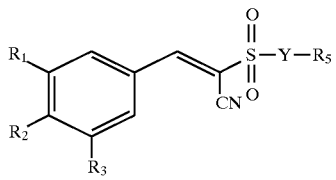

where $R_1$, $R_2$, and $R_3$ is each independently selected from the group consisting of alkyl, alkenyl, alkynyl, alkoxy, alkylaryl, OH, amine, thioether, SH, halogen, hydrogen, $NO_2$, and $NH_2$;

Y is either, nothing, —C(CN)=C—, -alkyl-, —NH-alkyl-; and $R_5$, is either CN or aryl.

Another aspect of the present invention describes a third class of receptor tyrosine kinase inhibitor compositions. These compositions are made up of a compound having the chemical formula:

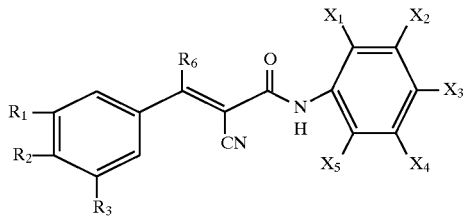

where $R_1$, $R_2$, $R_3$ and $R_6$ is each independently selected from the group consisting of alkyl, alkenyl, alkynyl, alkoxy, alkylaryl, halogen, hydrogen, OH, $NO_2$, amine, thioether, SH and $NH_2$; and $X_1$, $X_2$, $X_3$, $X_4$, and $X_5$ are each independently selected from the group consisting of hydrogen, halogen, trihalomethyl, and $NO_2$, provided that at least one of $X_1$, $X_2$, $X_3$, $X_4$, and $X_5$ is a trihalomethyl.

Another aspect of the present invention describes a fourth class of receptor tyrosine kinase compositions. These compositions are made up of a compound having the chemical formula:

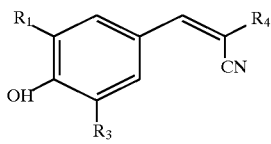

where $R_1$ and $R_3$ is each independently selected from the group consisting of alkyl, alkenyl, alkynyl, alkoxy, alkylaryl; and $R_4$ is selected from the group consisting of alkyl, alkylaryl, amide, and thioamide.

Another aspect of the present invention describes a fifth class of receptor tyrosine kinase compositions. These compositions are made up of a compound having the chemical formula:

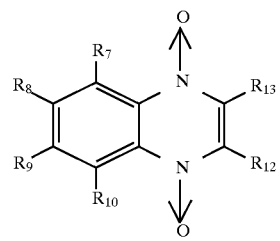

where $R_7$, $R_8$, $R_9$, and $R_{10}$, is each independently selected from the group consisting of alkyl, alkenyl, alkynyl, alkoxy, alkylaryl, OH, $NO_2$, amine, thioether, SH, halogen, hydrogen and $NH_2$;

$R_{12}$ has the chemical structure:

where $X_6$ is either O or S and $X_7$ is either methyl or trihalomethyl; and $R_{13}$ is either aryl or alkylaryl.

Another aspect of the present invention describes a compound able to inhibit protein tyrosine kinase activity selected from the group consisting of: M16, N17, N21, N22, N23, N29, R9, R10, R11, R12 and R13.

Another aspect of the present invention describes a method of treating a patient having a cell proliferative disorder characterized by over-activity or inappropriate activity of a receptor tyrosine kinase, preferably EGFR, PDGFR, or HER2, more preferably HER2. The method involves the step of administering to a patient a therapeutically effective amount of one the compounds described herein. Preferably, the cell proliferative disorder is a cancer.

Another aspect of the present invention describes a method of treating a patient having a cell proliferative disorder characterized by inappropriate or over-activity of HER2. The method involves administering to the patient a therapeutically effective amount of a compound able to significantly inhibit HER2 activity. Preferably, the compound selectively inhibits HER2. The composition is selected from one of the following:

a) a compound having the chemical formula:

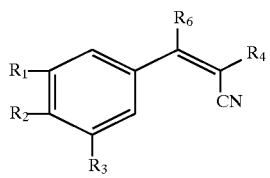

where $R_1$, $R_2$, $R_3$, and $R_6$ is each independently selected from the group consisting of alkyl, alkenyl, alkynyl, alkoxy, alkylaryl, OH, $NO_2$, amine, thioether, SH, halogen, hydrogen and $NH_2$; and $R_4$ is selected from the group consisting of alkyl, alkylaryl, thioamide, amide, CN, and sulfonyl.

b) a compound having the chemical formula:

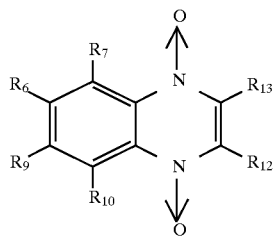

where $R_7$, $R_8$, $R_9$, and $R_{10}$, is each independently selected from the group consisting of alkyl, alkenyl, alkynyl, alkoxy, alkylaryl, OH, $NO_2$, amine, thioether SH, halogen, hydrogen and NH2;

$R_{12}$ is selected from the group consisting of alkyl, alkenyl, alkynyl, alkoxy, ester, amide, thioamide, alkylaryl, trihalomethyl, CN, OH, amine, thioether, SH, $NH_2$, and hydrogen; and $R_{13}$, is selected from the group consisting of aryl, alkyl, alkenyl, alkynyl, CN, alkylaryl, amide, and thioamide;

c) a compound having the chemical formula:

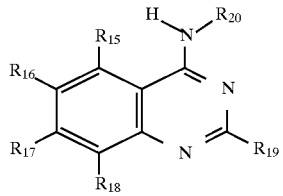

where $R_{15}$, $R_{16}$, $R_{17}$, $R_{18}$ and $R_9$, is each independently selected from the group consisting of hydrogen alkyl, alkenyl, alkynyl, alkoxy, OH, $NO_2$, amine, thioether, and SH; and $R_{20}$ is selected from the group consisting of alkyl, aryl, and alkylaryl; and d) a compound having the chemical formula:

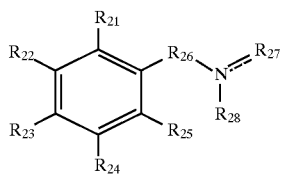

where $R_{21}$, $R_{22}$, $R_{23}$, $R_{24}$, and $R_{25}$, are each independently selected from the group consisting of hydrogen, halogen, OH, SH, alkyl, aryl, trihaloalkyl, preferably hydrogen, halogen, OH, or SH;

$R_{26}$ is either $CH_2$ or NH;

$R_{27}$ is either aryl or $=C(CN)_2$; and $R_{28}$ is either nothing or H, provided that if $R_{28}$ is nothing a double bond is present between N and $R_{27}$.

e) compound R9, R11, R13, and R15.

Different types of cell proliferative disorders characterized by inappropriate or over-activity of HER2 can be treated using the compounds and methods described herein. Examples of such disorders include: cancers such as blood cancers; breast carcinomas, stomach adenocarcinomas, salivary gland adenocarcinomas, endometrial cancers, ovarian adenocarcinomas, gastric cancers, colorectal cancers, and glioblastomas, where the cancer is characterized by overactivity or inappropriate activity of HER2.

Another aspect of the present invention describes a method of treating a patient having a cell proliferative disorder characterized by inappropriate EGFR activity. The method involves administering to the patient a therapeutically effective amount of a compound able to significantly inhibit EGFR activity. Preferably, the compound selectively inhibits EGFR. Several EGFR inhibitor compounds fall within the generic structures of HER2 compounds described in the previous aspects. Additionally, compounds R10 and R11 can selectively inhibit EGFR activity.

Another aspect of the present invention describes a method of determining the importance of a receptor tyrosine kinase in cellular growth. The method involves the steps of:

a) contacting a cell with a composition comprising a compound which significantly inhibits the activity of one or more receptor tyrosine kinases selected from the group consisting of: EGF-R, PDGF-R, and HER2; and b) measuring cell growth after step (a). Other features and advantages of the invention will be apparent from the following description of the preferred embodiments thereof, and from the claims.

BRIEF DESCRIPTION OF THE FIGURES

FIGS. 3a–l illustrate the chemical structures of exemplary tyrosine kinase inhibitors belonging to Group I.

DETAILED DESCRIPTION OF THE INVENTION

Figure 1A:
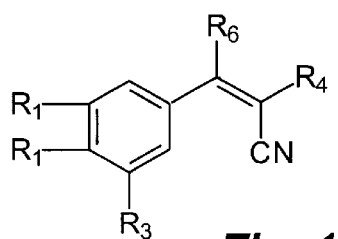
FIGS. 1a–1d illustrate the chemical structures of Groups I, II, III, and IV compounds respectively.
Figure 1B:
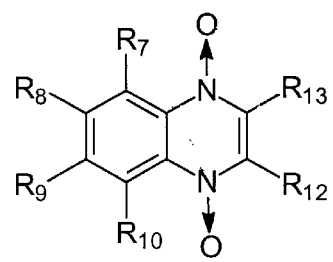
Figure 1C:
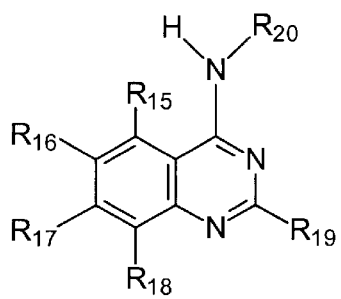
Figure 1D:
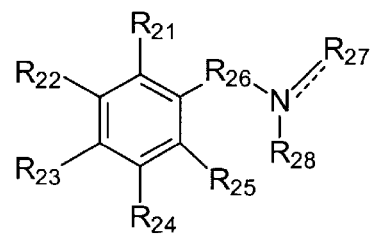
Figure 2A:
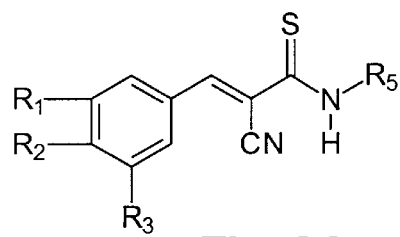
FIGS. 2a–e illustrate the chemical structures of five novel classes of tyrosine receptor kinase inhibitors.
Figure 2B:
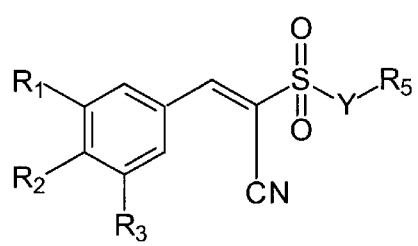
Figure 2C:
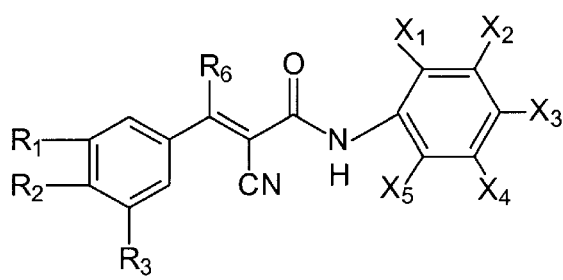
Figure 2D:
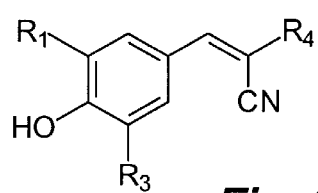
Figure 2E:
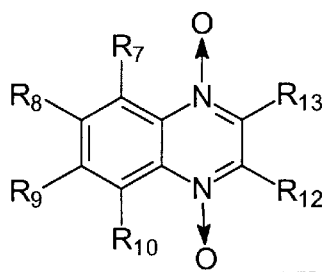
Figure 3A:
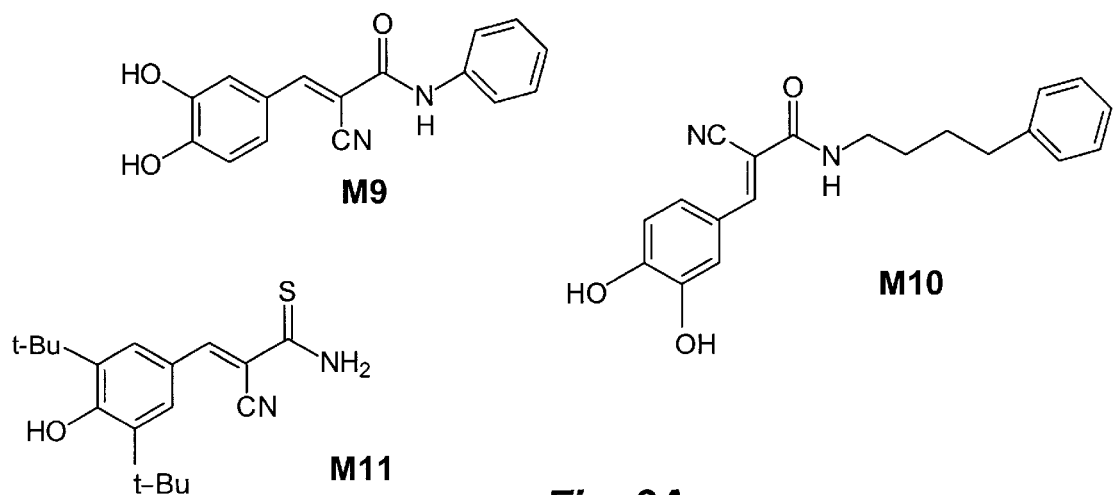
Figure 3B:
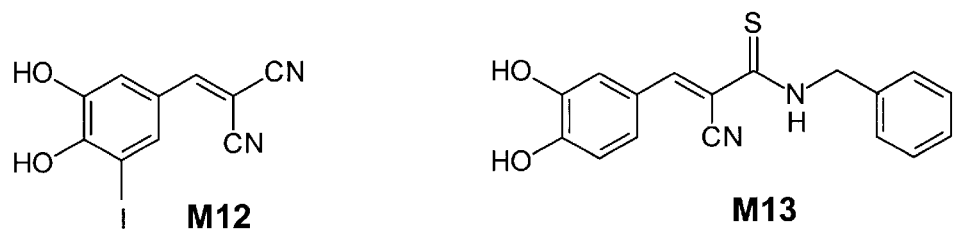
Figure 3C:
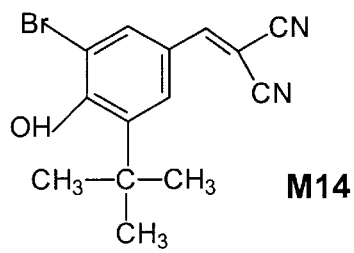
Figure 3C:
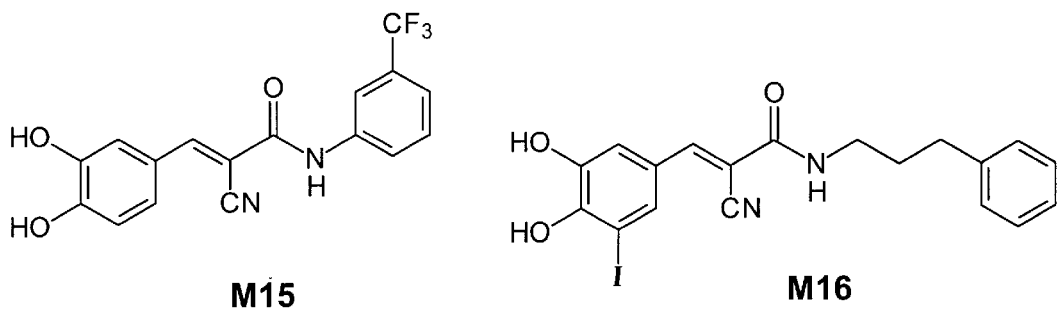
Figure 3D:
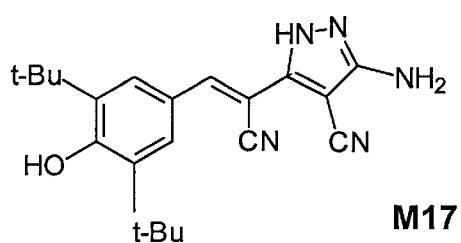
Figure 3D:
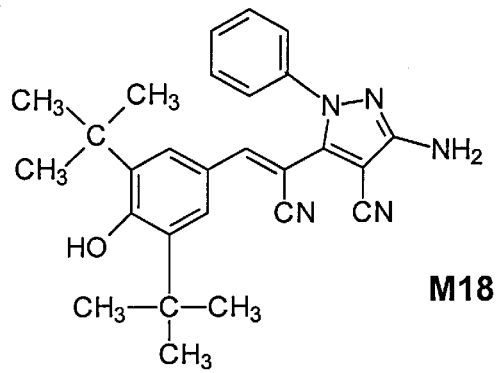
Figure 3D:
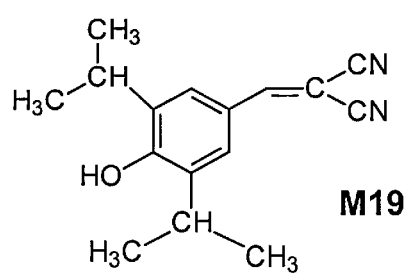
Figure 3E:
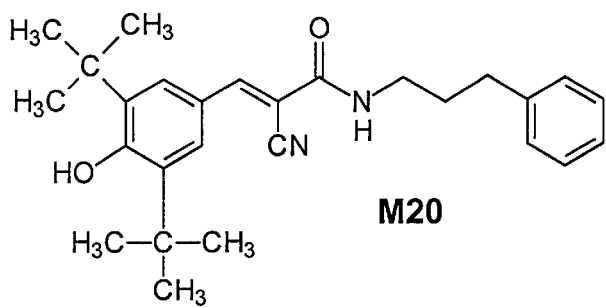
Figure 3E:
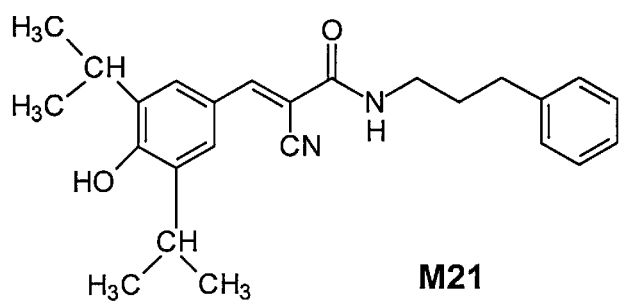
Figure 3E:
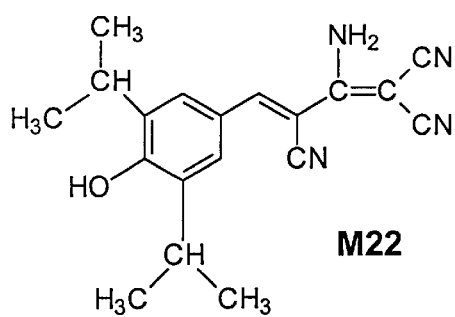
Figure 3F:
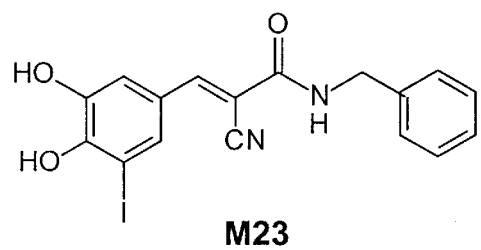
Figure 3F:
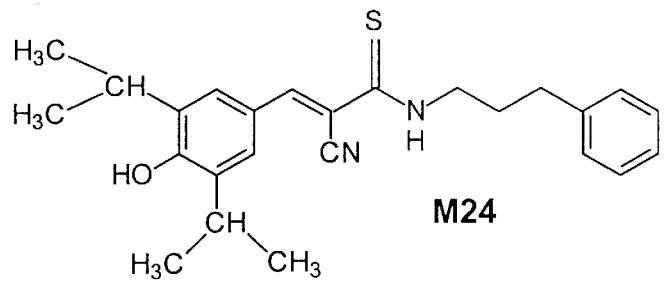
Figure 3F:
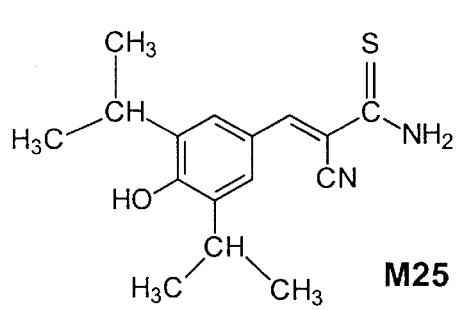
Figure 3G:
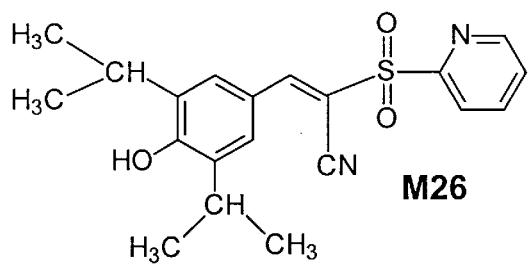
Figure 3G:
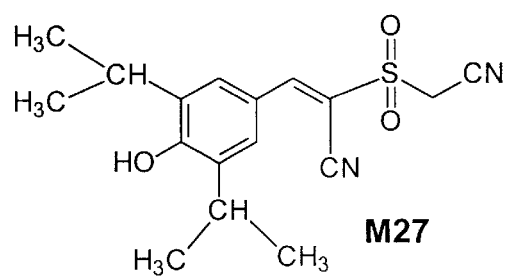
Figure 3G:
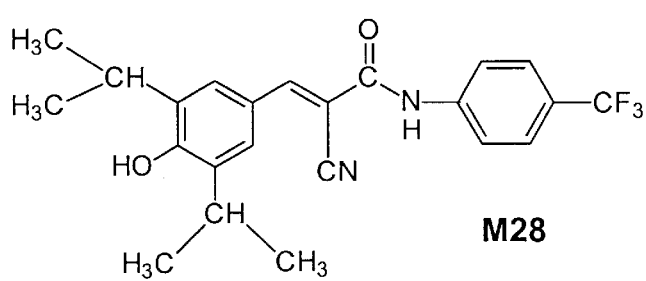
Figure 3H:
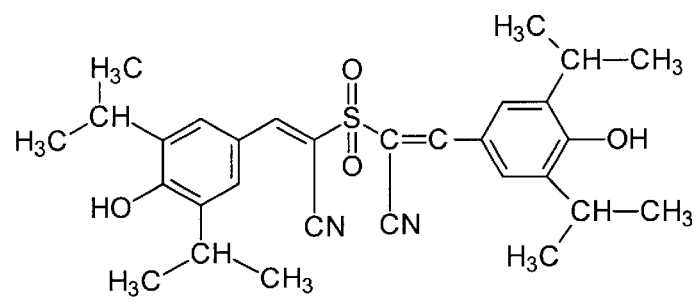
Figure 3H:
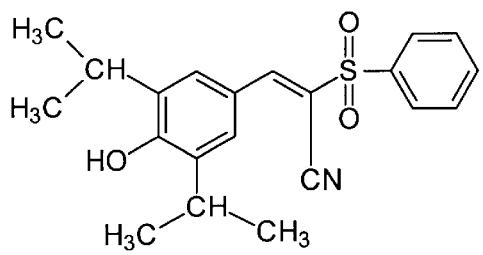
Figure 3H:
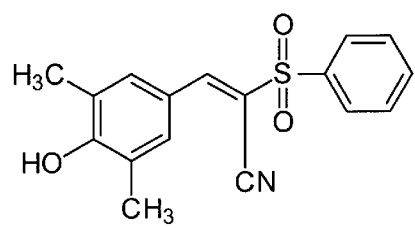
Figure 3I:
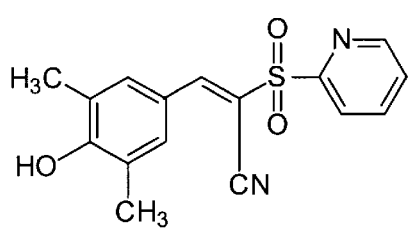
Figure 3I:
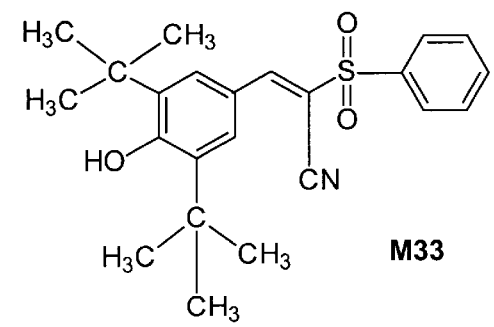
Figure 3I:
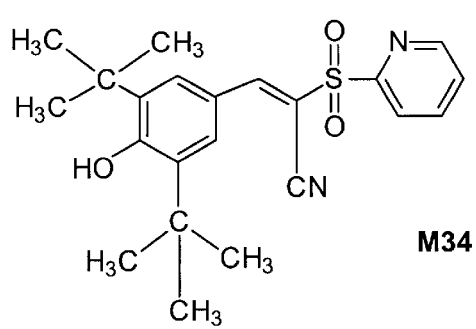
Figure 3L:
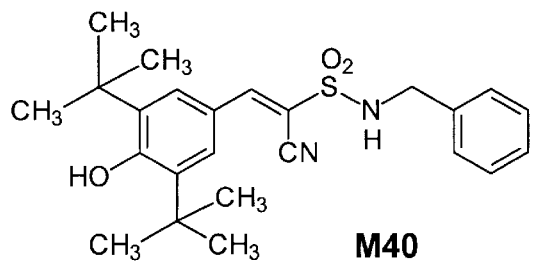
Figure 3L:
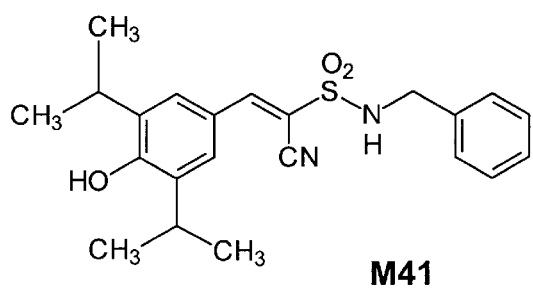
Figure 3L:
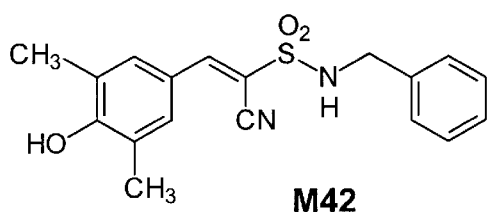
Figure 3L:
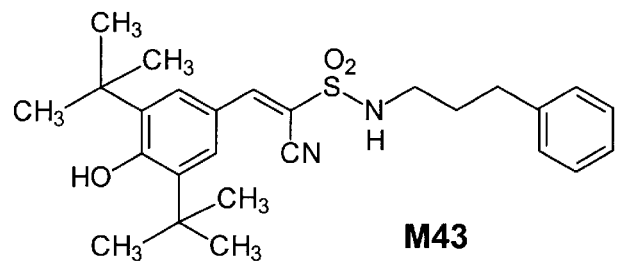
Figure 3L:
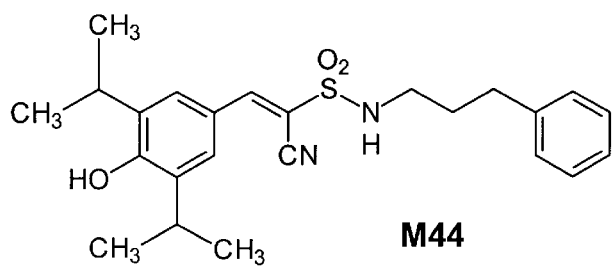
Figure 3L:
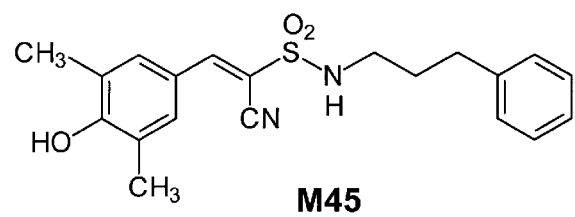
Figure 4A:
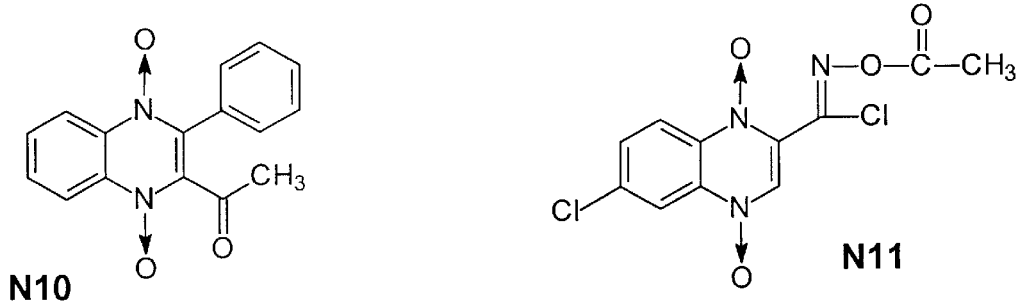
FIG. 4a–e illustrates the chemical structures of exemplary tyrosine kinase inhibitors belonging to Group II.
Figure 4B:
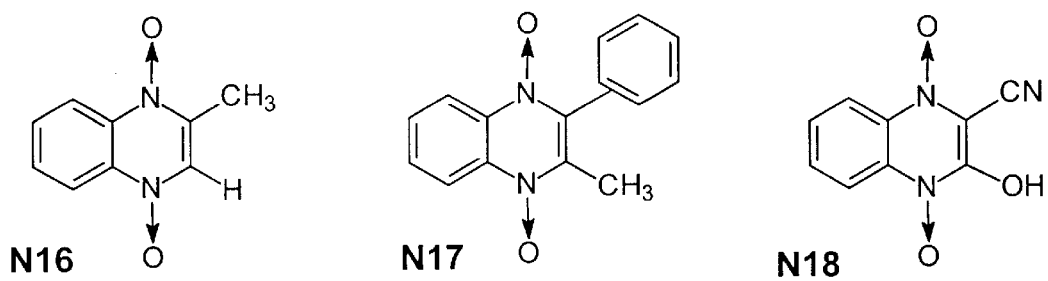
Figure 4C:
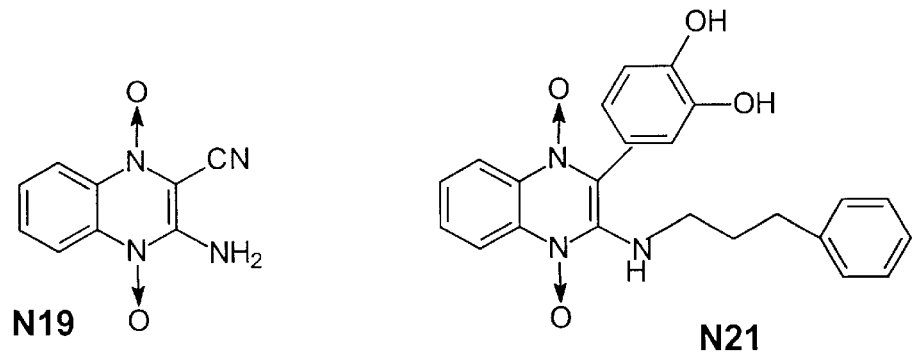
Figure 4D:
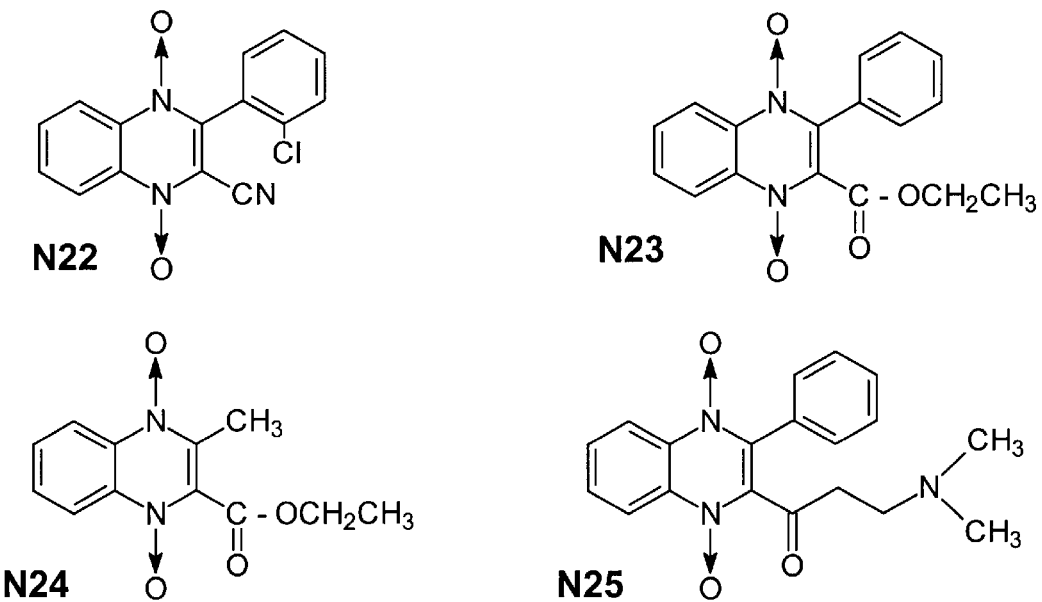
Figure 4E:
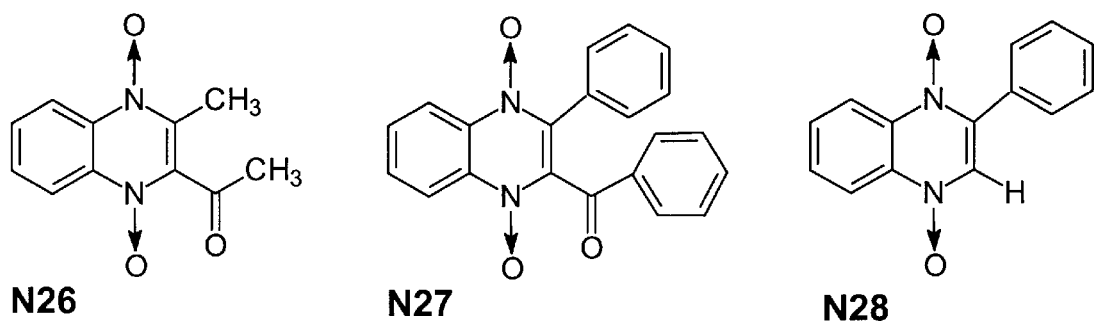
Figure 5A:
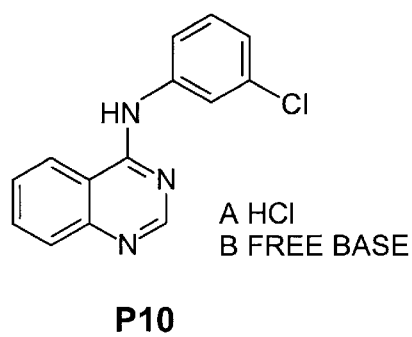
FIGS. 5a–b illustrate the chemical structures of exemplary tyrosine kinase inhibitors belonging to Group III.
Figure 5A:
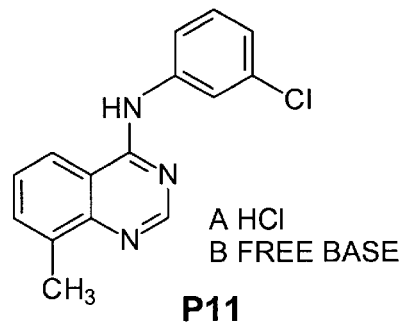
Figure 5A:
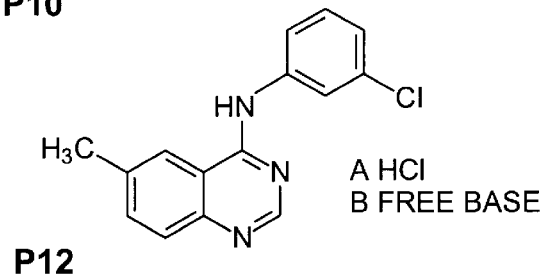
Figure 5B:
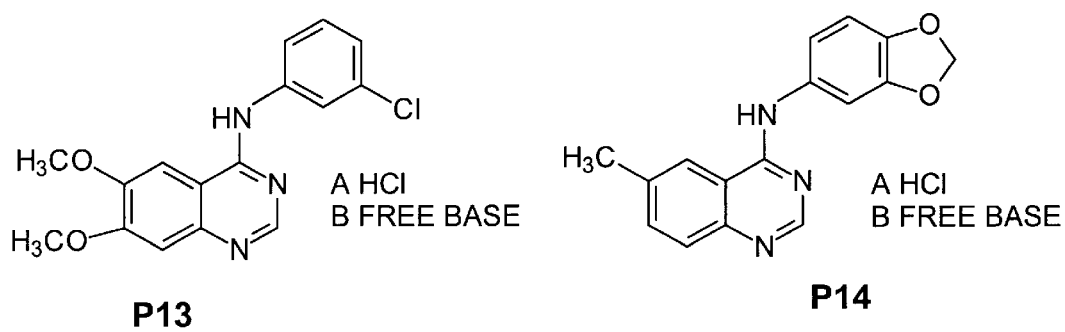
Figure 5B:
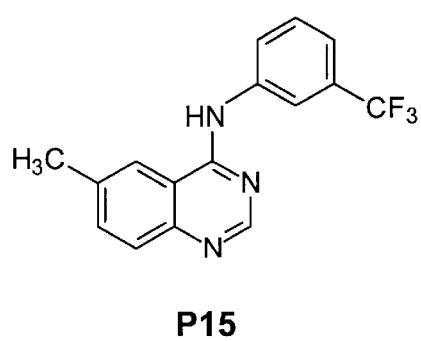

The present disclosure describes compounds and methods which can be used to inhibit receptor tyrosine kinase activity. The compounds and methods are preferably used in the treatment of cell proliferative disorders characterized by over-activity or inappropriate activity of a receptor tyrosine kinase. Different groups of HER2 and EGFR compounds are described, as are novel compounds which can inhibit one more receptor tyrosine kinase selected from the group consisting of HER2 and EGFR.

The compounds described herein can differ in their selectivity. Selectivity, or selective inhibition refers to the ability of a compound to significantly inhibit the activity of a first receptor tyrosine kinase (i.e., HER2, EGFR, or PDGFR) or growth of a cell containing the first receptor tyrosine kinase, but not significantly inhibit a second receptor tyrosine kinase (i.e., HER2, EGFR, or PDGFR) or growth of a cell containing the second receptor tyrosine kinase. Preferably, the activity is measured in an assay measuring cell growth as described below.

In general, it is preferred that a therapeutic compound be selective for a particular receptor tyrosine kinase. Receptor tyrosine kinases are important in many biological processes including cell growth, differentiation, aggregation, chemotaxis, cytokine release, and muscle contraction. Many of these events are mediated through different tyrosine kinase receptors. In addition, different tyrosine kinase receptors may be important for a particular biological function in different cell types. By developing selective inhibitors for a particular receptor tyrosine kinase, such as HER2 or EGFR, the potential toxic effect of the compound is decreased. In those conditions where more than one receptor tyrosine kinase plays a role (e.g., HER2 and EGFR) a compound which can inhibit both of these activities, but not other receptor kinases (e.g., PDGFR), would be preferred.

Various examples are provided below illustrating different aspects of the invention. Unless otherwise stated these examples are not intended to limit the invention.

I. Chemical Definitions

The following is a list of some of the definitions used in the present disclosure. An "alkyl" group refers to a saturated aliphatic hydrocarbon, including straight-chain, branched-chain, and cyclic alkyl groups. Preferably, the alkyl group has 1 to 12 carbons. More preferably, it is a lower alkyl of from 1 to 7 carbons, more preferably 1 to 4 carbons. The alkyl group may be substituted or unsubstituted. When substituted the substituted group(s) is preferably, hydroxyl, cyano, alkoxy, =O, =S, $NO_2$, N $(CH_3)_2$, amino, or SH.

An "alkenyl" group refers to an unsaturated hydrocarbon group containing at least one carbon-carbon double bond, including straight-chain, branched-chain, and cyclic groups. Preferably, the alkenyl group has 2 to 12 carbons. More preferably it is a lower alkenyl of from 2 to 7 carbons, more preferably 2 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH.

An "alkynyl" group refers to an unsaturated hydrocarbon group containing at least one carbon-carbon triple bond, including straight-chain, branched-chain, and cyclic groups. Preferably, the alkynyl group has 2 to 12 carbons. More preferably, it is a lower alkynyl of from 2 to 7 carbons, more preferably 1 to 4 carbons. The alkynyl group may be substituted or unsubstituted. When substituted, the substituted group(s) is preferably, hydroxyl, cyano, alkoxy, =O, =S, $NO_2$, $N(CH_3)_2$, amino or SH.

An "alkoxy" group refers to an "—O-alkyl" group, where "alkyl" is defined as described above.

An "aryl" group refers to an aromatic group which has at least one ring having a conjugated pi electron system and includes carbocyclic aryl, heterocyclic aryl and biaryl groups, all of which may be optionally substituted. Preferably, the aryl is a substituted or unsubstituted phenyl or pyridyl. Preferred aryl substituent(s) preferably phenyl or pyridyl) are halogen, trihalomethyl, hydroxyl, SH, OH, $NO_2$, amine, thioether, cyano, alkoxy, alkyl, and amino groups.

An "alkylaryl" group refers to an alkyl (as described above), covalently joined to an aryl group (as described above). Preferably, the alkyl is a lower alkyl.

"Carbocyclic aryl" groups are groups wherein the ring atoms on the aromatic ring are all carbon atoms. The carbon atoms are optionally substituted.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted.

An "amide" refers to an —C(O)—NH—R, where R is either alkyl, aryl, alkylaryl or hydrogen.

A "thioamide" refers to —C(S) —NH—R, where R is either alkyl, aryl, alkylaryl or hydrogen. An "ester" refers to an —C(O)—OR', where R' is either alkyl, aryl, or alkylaryl.

An "amine" refers to a —N(R")R'", where R" and R'", is independently either hydrogen, alkyl, aryl, or alkylaryl, provided that R" and R'" are not both hydrogen.

A "thioether" refers to —S—R, where R is either alkyl, aryl, or alkylaryl.

A "sulfonyl" refers to —S(O)$_2$—R, where R is aryl, C(CN)=C-aryl, $CH_2$—CN, alkylaryl, NH-alkyl, NH-alkylaryl, or NH-aryl.

II. Receptor Tyrosine Kinase Inhibitory Compounds

Different groups of receptor tyrosine kinase inhibitor compounds are described below.

A. Group I Compounds

Group I compounds have the general structure:

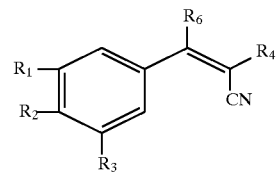

where $R_1$, $R_2$, $R_3$, and $R_6$ is each independently either alkyl, alkenyl, alkynyl, alkoxy, alkylaryl, OH, $NO_2$, amine, thioether, SH, halogen, hydrogen or $NH_2$; and $R_4$, is either alkyl, alkylaryl, amide, thioamide, CN, or sulfonyl.

Examples of Group I compounds are listed in Table I and shown in FIG. 3.

TABLE I

| Compound | $R_1$ | $R_2$ | $R_3$ | $R_4$ | $R_6$ |
|---|---|---|---|---|---|
| M9 | OH | OH | H | C(=O)NH-phenyl | H |
| M10 | H | OH | OH | C(=O)NHCH$_2$CH$_2$CH$_2$CH$_2$-phenyl | H |
| M11 | t-butyl | OH | t-butyl | C(=S)NH$_2$ | H |
| M12 | OH | OH | I | CN | H |
| M13 | OH | OH | H | C(=S)NHCH$_2$C$_6$H$_6$ | H |
| M14 | Br | OH | t-butyl | CN | H |
| M15 | OH | OH | H | C(=O)NH(3-CF$_3$-phenyl) | H |
| M16 | OH | OH | I | C(=O)NHCH$_2$CH$_2$CH$_2$-phenyl | H |
| M17 | t-butyl | OH | t-butyl | 3-amino-4-cyano-1-pyrazol-5-yl | H |

TABLE I-continued

| Compound | $R_1$ | $R_2$ | $R_3$ | $R_4$ | $R_6$ |
|---|---|---|---|---|---|
| M18 | t-butyl | OH | t-butyl | 2-phenyl-3-amino-4-cyano-2-pyrazol-5-yl | H |
| M19 | isopropyl | OH | isopropyl | CN | H |
| M20 | t-butyl | OH | t-butyl | C(=O)NH(CH$_2$)$_3$-phenyl | H |
| M21 | isopropyl | OH | isopropyl | C(=O)NH(CH$_2$)$_3$-phenyl | H |
| M22 | isopropyl | OH | isopropyl | C(NH$_2$)=C(CN)$_2$ | H |
| M23 | OH | OH | I | C(=O)NHCH$_2$-phenyl | H |
| M24 | isopropyl | OH | isopropyl | C(=S)NH(CH$_2$)$_3$-phenyl | H |
| M25 | isopropyl | OH | isopropyl | C(=S)NH$_2$ | H |
| M26 | isopropyl | OH | isopropyl | SO$_2$-pyrid-2-yl | H |
| M27 | isopropyl | OH | isopropyl | SO$_2$—CH$_2$—CN | H |
| M28 | isopropyl | OH | isopropyl | C(=O)NH-4-CF$_3$-phenyl | H |
| M29 | isopropyl | OH | isopropyl | SO$_2$C(CN)=C-3,5-diisopropyl-4-hydroxy-phenyl | H |
| M30 | isopropyl | OH | isopropyl | SO$_2$-phenyl | H |
| M31 | methyl | OH | methyl | SO$_2$-phenyl | H |
| M32 | methyl | OH | methyl | SO$_2$-pyrid-2-yl | H |
| M33 | t-butyl | OH | t-butyl | SO$_2$-phenyl | H |
| M34 | t-butyl | OH | t-butyl | SO$_2$-pyrid-2-yl | H |
| M35 | t-butyl | OH | t-butyl | C(=O)NH-4-CF$_3$-phenyl | H |
| M36 | t-butyl | OH | t-butyl | SO$_2$—CH$_2$—CN | H |
| M37 | t-butyl | OH | t-butyl | SO$_2$C(CN)=C-3,5-di-t-butyl-4-hydroxyl-phenyl | H |
| M38 | methyl | OH | methyl | SO$_2$—C(CN)=C-3,5-dimethyl-3-hydroxyl-phenyl | H |
| M39 | H | NO$_2$ | OH | C(=O)NH(CH$_2$)$_2$-phenyl | H |
| M40 | t-butyl | OH | t-butyl | SO$_2$—NH—CH$_2$-phenyl | H |
| M41 | isopropyl | OH | isopropyl | SO$_2$—NH—CH$_2$-phenyl | H |
| M42 | methyl | OH | methyl | SO$_2$—NH—CH$_2$-phenyl | H |
| M43 | t-butyl | OH | t-butyl | SO$_2$—NH—(CH$_2$)$_2$-phenyl | H |
| M44 | isopropyl | OH | isopropyl | SO$_2$—NH—(CH$_2$)$_2$-phenyl | H |
| M45 | methyl | OH | methyl | SO$_2$—NH—(CH$_2$)$_2$-phenyl | H |

In general, it appears that $R_1$ and $R_3$ are important positions for the placement of hydrophobic groups such as alkoxy, bromine, halogen, alkyl, and alkylaryl.

Thus, in one preferred embodiment of Group I HER2 inhibitors the preferred R group are as follows:

$R_1$ and $R_3$ are independently selected from the group consisting of alkoxy, iodine, alkyl, or alkylaryl. More preferably, $R_1$, and $R_3$ are independently t-butyl, isopropyl, or iodine;

$R_2$ is OH;

$R_4$ is either CN, alkyl, alkylaryl, amide, thioamide, or sulfonyl. Preferably, $R_4$ is either sulfonyl, C(=O)NH(CH$_2$)$_4$-phenyl, C(=S)NH$_2$, CN, C(=S)NHCH$_2$-phenyl, C(=O)NH(3-CF$_3$-phenyl), C(=O)NH(CH$_2$)$_3$-phenyl, 3-amino-4-cyano-1-pyrazol-5-yl, 2-phenyl-3-amino-4-cyano-2-pyrazol-5-yl, C(=O)NH(CH$_2$)$_3$-phenyl, C(NH$_2$)=C(CN)$_2$. When $R_4$ is a sulfonyl having the structure SO$_2$—R (see definition section supra), R is preferably, aryl, alkylaryl, NH-alkylaryl, C(CN)=C-aryl, or CH-CN-aryl. Preferably, the aryl (including the aryl in alkylaryl) has 1 to 5 groups each independently selected from the group consisting of: hydrogen, halogen, trihalomethyl, hydroxyl, SH, OH, NO$_2$, amine, thioether, cyano, alkoxy, alkyl, and amino groups; more preferably the substituents are each independently H, alkyl, or OH, more preferably the alkyl is either methyl, t-butyl or isopropyl; more preferably 1 to 3 substituents are each independently either OH, methyl, t-butyl or isopropyl, and the remaining substituents are hydrogen; preferably, the aryl is either phenyl or pyridyl with preferred substituents as described above; and $R_6$ is hydrogen.

A second preferred embodiment describing HER2 inhibitors are describes as follows:

$R_1$ is either hydrogen, alkyl, or OH, preferably, t-butyl, isopropyl, or OH;

$R_2$ is OH;

$R_3$ is either alkyl, halogen, hydrogen or OH, preferably t-butyl, isopropyl, hydrogen or iodine;

$R_4$ is either CN, alkyl, alkylaryl, amide, thioamide, or sulfonyl. Preferably, $R_4$ is either sulfonyl, C(=O)NH(CH$_2$)$_4$-phenyl, C(=S)NH$_2$, CN, C(=S)NHCH$_2$-phenyl, C(=O)NH(3-CF$_3$-phenyl), C(=O)NH(CH$_2$)$_3$-phenyl, 3-amino-4-cyano-1-pyrazol-5-yl, 2-phenyl-3-amino-4-cyano-2-pyrazol-5-yl, C(=O)NH(CH$_2$)$_3$-phenyl, C(NH$_2$)=C(CN)$_2$. When $R_4$ is a sulfonyl having the structure SO$_2$—R (see definition section supra), R is preferably, aryl, alkylaryl, NH-alkylaryl, C(CN)=C-aryl, or CH—CN-aryl. Preferably, the aryl (including the aryl in alkylaryl) has 1 to 5 groups each independently selected from the group consisting of: hydrogen, halogen, trihalomethyl, hydroxyl, SH, OH, NO$_2$, amine, thioether, cyano, alkoxy, alkyl, and amino groups; more preferably the substituents are each independently H, alkyl, or OH, more preferably the alkyl is either methyl, t-butyl or isopropyl; more preferably 1 to 3 substituents are each independently either OH, methyl, t-butyl or isopropyl and the remaining substituents are hydrogen; preferably, the aryl is either phenyl or pyridyl with preferred substituents as described above;

$R_6$ is hydrogen.

In a preferred embodiment describing EGF-R inhibitors $R_1$ is alkyl, OH, or halogen, preferably t-butyl, OH, or Br; $R_2$ is OH; $R_3$ is alkyl or halogen, preferably t-butyl or I; $R_4$ is one of the $R_4$ substituents shown in Table I for those compounds which can inhibit EGF-R; and $R_6$ is hydrogen. Compounds M10 and M14 are mentioned in other references. M14 is mentioned by Ohmichi et al., supra, which refers to Birchall and Harney Chem. Abstr. 88:535 (1978). M10 is mentioned in Osherov et al., Journal Biological Chemistry 268:11134–11142, 1993 and Gazit et al., J. Med. Chem. 34:1896–1907, 1991 (Table III compound no. 56).

Several of the compounds in Table I are believed to novel: M11, M12, M13, M15, M16, M17, M18, M19, M26, M27, M29, M30, M31, M32, M33, M34, M36, M37, M38, M40, M41, M42, M43, M44, and M45. Of these compounds M11 (AG879) and M12 (AG974) were mentioned by Ohmichi et al, Biochemistry 32:4650–4658, (1993). (Not admitted to be prior art.)

Several of the compounds are exemplary of classes of novel compounds. Class one compounds have the following chemical formula:

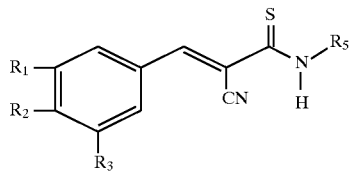

where $R_1$, $R_2$, and $R_3$ is each independently selected from the group consisting of alkyl, alkenyl, alkynyl, alkoxy, alkylaryl, OH, amine, thioether, SH, halogen, hydrogen and $NH_2$; and $R_5$ is $NH_2$, or an alkylaryl comprising an alkyl group and an aryl group having the following structure:

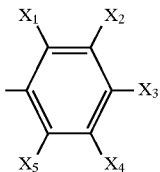

where $X_1$, $X_2$, $X_3$, $X_4$, and $X_5$ is each independently selected from the group consisting of hydrogen, halogen, alkyl, alkoxy, OH, trihalomethyl, and $NO_2$; preferably hydrogen, halogen, alkyl, trihalomethyl, and $NO_2$.

Preferably, $R_1$ is OH, $R_2$ is OH, $R_3$ is H, $R_5$ is a lower alkylaryl and four of said $X_1$, $X_2$, $X_3$, $X_4$, and $X_5$ is hydrogen while one of said $X_1$, $X_2$, $X_3$, $X_4$, and $X_5$ is $CF_3$.

An example of a class one compound is M13. Interestingly M13 differs from a compound described by Gazit supra, *J. Med. Chem.* 1991, in that compound M13 has a sulfur replacing an oxygen in compound 42 mentioned by Gazit. However, Gazit compound 42 is described as exerting over a 10 fold greater inhibition of EGFR compared to HER2, while M13 as described in Example 1 below displays at least a 7 fold greater inhibition of HER2 compared to EGF-R.

Class two compounds have the chemical formula:

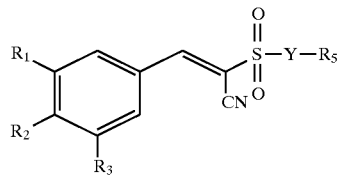

where $R_1$, $R_2$, and $R_3$ is each independently selected from the group consisting of alkyl, alkenyl, alkynyl, alkoxy, alkylaryl, OH, amine, thioether, SH, halogen, hydrogen, NO, and $NH_2$;

Y is either nothing, —C(CN)=C—, -alkyl-, —NH-alkyl-; and $R_5$ is either CN or aryl.

A preferred embodiment of class 2 compounds is described as follows:

$R_2$ is OH;

$R_1$ and $R_3$ is each independently t-butyl or isopropyl;

Y is either nothing, —C(CN)=C—, -lower alkyl-, NH-lower alkyl-, more preferably nothing, -lower alkyl- or —NH-lower alkyl-; and $R_5$ aryl is either CN or phenyl or pyridyl having 1 to 5 substituents each independently selected from the group consisting of: hydrogen, halogen, trihalomethyl, hydroxyl, SH, OH, $NO_2$, amine, thioether, cyano, alkoxy, alkyl, and amino groups; more preferably the substituents are each independently H, alkyl, or OH, more preferably the alkyl is either methyl, t-butyl or isopropyl; more preferably 1 to 3 substituents are each independently either OH, methyl, t-butyl or isopropyl and the remaining substituents are hydrogen.

Examples of class two compounds are M26, M27, M29, M30, M31, M32, M33, M34, M37, M38, M40, M41, M42, M43, M44 and M45. Bulkier $R_1$ and $R_3$ groups such as t-butyl or isopropyl are preferred. M31 and M38 containing $R_1$ and $R_3$ methyl groups have less activity in cellular assays described in the Examples below, than analogous compounds having bulkier $R_1$ and $R_3$ groups.

Class three compounds have the following chemical formula:

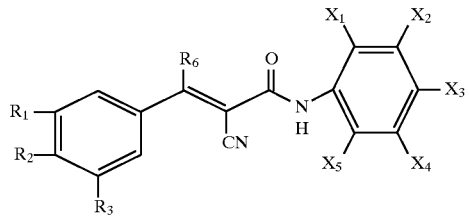

where $R_1$, $R_2$, $R_3$ and $R_6$ is each independently selected from the group consisting of alkyl, alkenyl, alkynyl, alkoxy, alkylaryl, halogen, hydrogen, OH, amine, thioether, SH and $NH_2$; and $X_1$, $X_2$, $X_3$, $X_4$, and $X_5$ are each independently selected from the group consisting of hydrogen, halogen, trihalomethyl, alkyl, alkenyl, alkynyl, alkoxy, and $NO_2$, provided that at least one of $X_1$, $X_2$, $X_3$, $X_4$, and $X_5$ is a trihalomethyl.

Preferably $R_1$ is OH, $R_2$ is OH, $R_3$ is hydrogen, $R_6$ is hydrogen, and one of $X_1$, $X_2$, $X_3$, $X_4$, and $X_5$ is trihalomethyl and the other groups are hydrogen; more preferably the trihalomethyl is $CF_3$. M15 is an example of a class 3 compound.

Class four compounds have the following chemical formula:

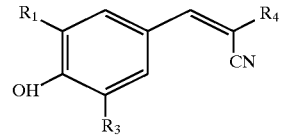

where $R_1$ and $R_3$ is each independently selected from the group consisting of alkyl, alkenyl, alkynyl, alkoxy, alkylaryl; and $R_4$ is selected from the group consisting of alkyl, alkylaryl, thioamide, and amide.

Preferably, $R_1$ and $R_3$ is each independently an alkyl, more preferably t-butyl or isopropyl. Preferably $R_4$ is alkyl, aryl, or alkylaryl. Examples of class four compounds are M11, M17, M18, and M19.

The members of classes 1 to 4 can be used to inhibit one or more receptor tyrosine kinases selected from the group consisting of EGFR and HER2, preferably HER2, and are preferably used to treat a cell proliferative disorder characterized by over-activity or inappropriate activity of EGFR or HER2, preferably HER2.

B. Group II Compounds

Group 2 are quinoxoline oxides having the following chemical formula;

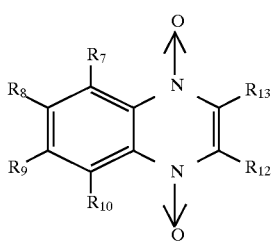

where $R_7$, $R_8$, $R_9$, and $R_{10}$, is each independently selected from the group consisting of alkyl, alkenyl, alkynyl, alkoxy, alkylaryl, OH, $NO_2$, amine, thioether, SH, halogen, hydrogen and $NH_2$;

$R_{12}$ is selected from the group consisting of alkyl, alkenyl, alkynyl, alkoxy, ester, amide, thioamide, alkylaryl, trihalomethyl, CN, OH, amine, thioether, SH, $NH_2$, and hydrogen; and $R_{13}$ is selected from the group consisting of aryl, alkyl, alkenyl, alkynyl, CN, alkylaryl, amide, and thioamide.

Examples of Group II compounds are listed in Table II and shown in FIG. 4. Preferably, as illustrated in Table II, $R_7$ and $R_{10}$ are each hydrogen.

TABLE II

| Compound | $R_8$ | $R_9$ | $R_{12}$ | $R_{13}$ | EGFR | HER2 |
|---|---|---|---|---|---|---|
| N10 | H | H | C(=O)CH$_3$ | phenyl | – | + |
| N11 | H | Cl | H | C(Cl)=NOC(=O)CH$_3$ | ND | ND |
| N16 | H | H | H | CH$_3$ | ND | ND |
| N17 | H | H | CH$_3$ | phenyl | ND | ND |
| N18 | H | H | OH | CN | ND | ND |
| N19 | H | H | NH$_2$ | CN | ND | ND |
| N21 | H | H | NHCH$_2$CH$_2$CH$_2$-phenyl | 4,5-dihydroxy-phenyl | ND | ND |
| N22 | H | H | CN | o-chloro-phenyl | ND | ND |
| N23 | H | H | C(=O)OCH$_2$CH$_3$ | phenyl | ND | ND |
| N24 | H | H | C(=O)OCH$_2$CH$_3$ | CH$_3$ | ND | ND |
| N25 | H | H | C(=O)CH$_2$CH$_2$N(CH$_3$)$_2$ | phenyl | ND | ND |
| N26 | H | H | C(=0)CH$_3$ | CH$_3$ | ND | ND |
| N27 | H | H | C(=O)-phenyl | phenyl | ND | ND |
| N28 | H | H | H | phenyl | ND | ND |

ND- not determined.
(+) inhibits receptor kinase activity with an IC$_{50}$ of less than 50 μM in a cellular kinase assay.
(–) inhibits recepter kinase activity with an IC$_{50}$ of at least 50 μM in a cellular kinase assay.

In a preferred embodiment describing HER2 inhibitors $R_7$, $R_8$, $R_9$, and $R_{10}$ is independently selected from the group consisting of alkyl, alkenyl, alkynyl, alkoxy, alkylaryl, OH, amine, thioether, SH, halogen and hydrogen, preferably $R_7$ and $R_{10}$ is hydrogen, preferably $R_8$ and $R_9$ is independently alkyl or hydrogen, more preferably hydrogen; $R_{12}$ is either alkyl, ester, amide, thioamide, alkylaryl, trihalomethyl, CN, OH, amine, thioether, SH, $NH_2$, or hydrogen, preferably one of the groups shown in Table II; and $R_{13}$ is either aryl, alkyl, CN, alkylaryl, amide, thioamide, preferably one of the groups shown in Table II.

Compounds N10, N17, N22, N23, N24, N27, and N29 are believed to be novel compounds (Class 5), which based on the present application are expected to inhibit HER2 activity, EGFR or PDGFR activity. Compounds N16, N18 and N19 are mentioned by Ley and Seng in *Synthesis* 415–422 (1975). Compounds N26, N27, and N28 are mentioned by Issidorides and Haddadin *J. Organic Chem.* 31:4067–4068. N10selectively inhibited HER2, and inhibited growth of cells characterized by over-activity of HER2.

In a more preferred embodiment, $R_7$, $R_8$, $R_9$, and $R_{10}$ are independently selected from the group consisting of alkyl, alkenyl, alkynyl, alkoxy, alkylaryl, OH, amine, thioether, SH, halogen, hydrogen, preferably hydrogen, methyl, or methoxy; $R_{12}$ has the chemical structure:

where $X_6$ is either O or S, $X_7$ is either methyl or trihalomethyl; and $R_{13}$ is either aryl or alkylaryl, preferably aryl.

C. Group III Compounds

Group III compounds have the following chemical structure:

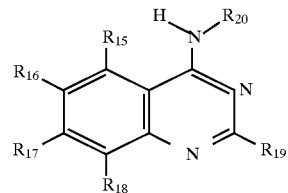

where $R_{15}$, $R_{16}$, $R_{17}$, $R_{18}$ and $R_{19}$, is each independently selected from the group consisting of hydrogen, alkyl, alkenyl, alkynyl, alkoxy, OH, amine, thioether, and SH; and $R_{20}$ is selected from the group consisting of alkyl, aryl, and alkylaryl.

Examples of Group III compounds are listed in Table III and shown in FIG. 5.

TABLE III

| Compound | $R_{16}$ | $R_{17}$ | $R_{18}$ | $R_{20}$ | EGFR | HER2 |
|---|---|---|---|---|---|---|
| P10a | H | H | H | m-chloro-phenyl | + | + |
| P10b | H | H | H | m-chloro-phenyl | + | + |
| P11 | H | H | CH$_3$ | m-chloro-phenyl | ND | ND |
| P12a | CH$_3$ | H | H | m-chloro-phenyl | + | + |
| P12b | CH$_3$ | H | H | m-chloro-phenyl | + | + |
| P13a | OCH$_3$ | OCH$_3$ | H | m-chloro-phenyl | + | + |
| P13b | OCH$_3$ | OCH$_3$ | H | m-chloro-phenyl | + | + |
| P14a | CH$_3$ | H | H | 4,5-methylene-dioxy-phenyl | + | – |
| P14b | CH$_3$ | H | H | 4,5-methylene-dioxy-phenyl | + | – |
| P15 | CH$_3$ | H | H | m-CF$_3$-phenyl | + | – |

ND- not determined.
(+) inhibits receptor kinase activity with an IC$_{50}$ of less than 50 μM in a cellular kinase assay.
(–) inhibits receptor kinase activity with an IC$_{50}$ of at least 50 μM in a cellular kinase assay.

In a preferred embodiment describing HER2 inhibitors $R_{15}$ and $R_{19}$ are each hydrogen; $R_{16}$ is hydrogen, alkyl, or alkoxy, preferably hydrogen, methyl, or methoxy; $R_{17}$ is hydrogen, alkyl, or alkoxy, preferably hydrogen or methoxy; $R_{18}$ is hydrogen, alkyl, or alkoxy, preferably hydrogen or methyl, more preferably hydrogen; $R_{20}$ is aryl, preferably a mono-substituted phenyl group where the substituent is $CF_3$ or a halogen.

In a preferred embodiment describing EGFR inhibitors $R_{15}$ and $R_{19}$ are each hydrogen; $R_{16}$ is hydrogen, alkyl, or alkoxy, preferably hydrogen, methyl, or methoxy; $R_{17}$ is hydrogen, alkyl, or alkoxy, preferably hydrogen or methoxy; $R_{18}$ is hydrogen, alkyl, or alkoxy, preferably hydrogen or methyl, more preferably hydrogen; $R_{20}$ is aryl, more preferably either 1) a mono-substituted phenyl group where the substituent is $CF_3$ or a halogen, or 2) a phenyl group substituted with a methylene dioxy.

References mentioning quinazoline derivatives include "Quinazoline Derivatives" AU-3-31010/93 (published Jul. 22, 1993), and "Therapeutic Preparations Containing Quinazoline Derivatives" 0 520 722 A1 published Dec. 30, 1992.

D. Group IV Compounds

Figure 6:
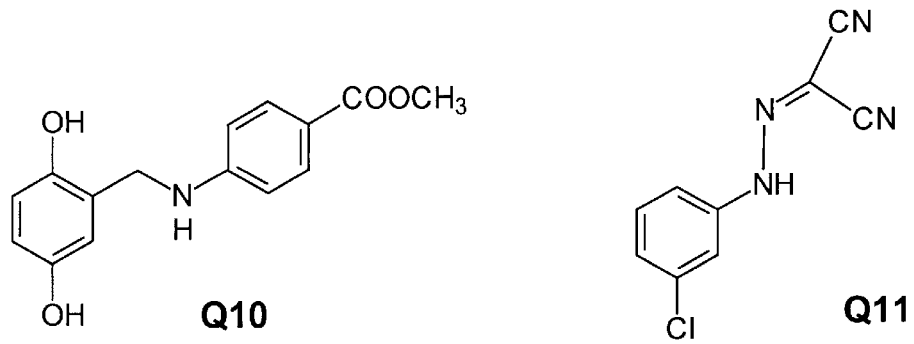
FIG. 6 illustrates the chemical structures of exemplary tyrosine kinase inhibitors belonging to Group IV.
Figure 7A:
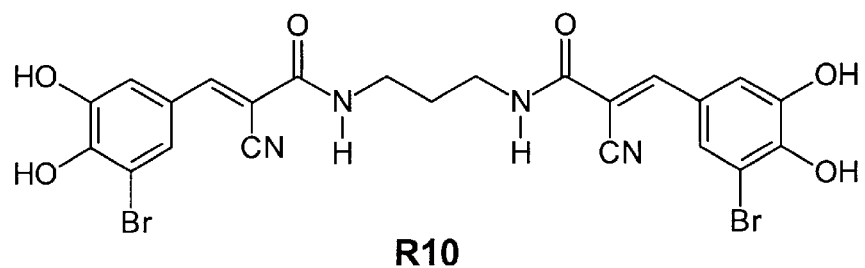
FIG. 7a–c illustrates the chemical structures of additional tyrosine kinase inhibitors.
Figure 7A:
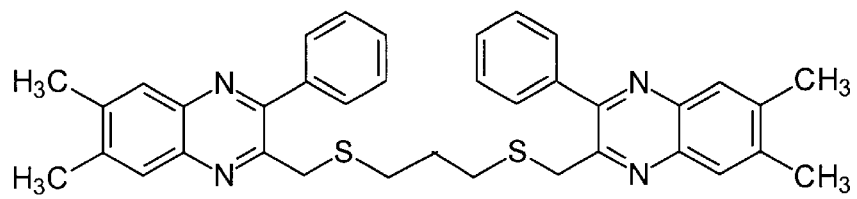
Figure 7A:
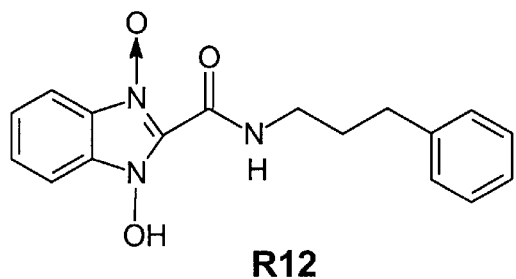
Figure 7B:
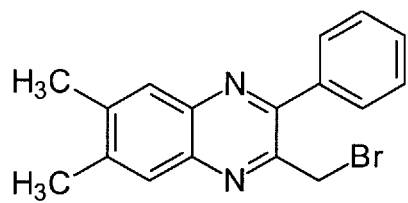
Figure 7B:
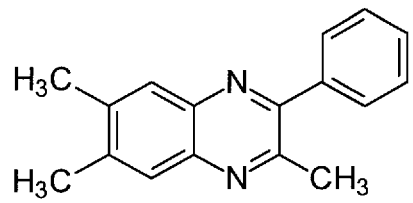
Figure 7B:
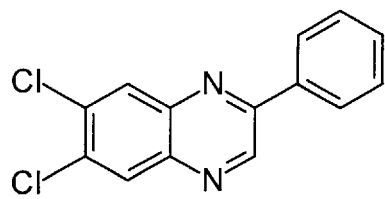
Figure 7B:
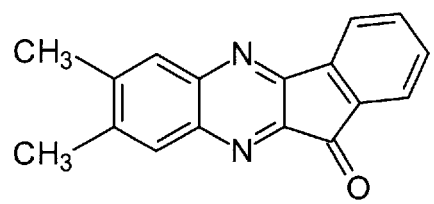
Figure 7C:
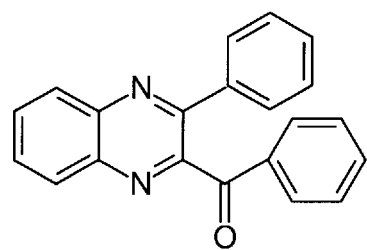

Group IV compounds have the following chemical structure:

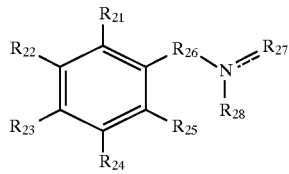

where $R_{21}$, $R_{22}$, $R_{23}$, $R_{24}$, and $R_{25}$, are each independently selected from the group consisting of hydrogen, halogen, OH, SH, alkyl, aryl, trihaloalkyl, preferably hydrogen, halogen, OH, or SH;

$R_{26}$ is either $CH_2$ or NH;

$R_{27}$ is either aryl or $=C(CN)_2$; and $R_{28}$ is either nothing or H, provided that if $R_{28}$ is nothing a double bond is present between N and $R_{27}$ Examples of Group IV compounds are listed in Table IV and shown in FIG. 6.

TABLE IV

| Compound | $R_{21}$ | $R_{22}$ | $R_{23}$ | $R_{24}$ | $R_{25}$ | $R_{26}$ | $R_{27}$ | $R_{28}$ |
|---|---|---|---|---|---|---|---|---|
| Q10 | OH | H | H | OH | H | $CH_2$ | p-COOCH$_3$-phenyl | H |
| Q11 | H | H | H | Cl | H | NH | $=C(CN)_2$ | nothing |

Q10 and Q11 both significantly inhibited HER2 activity, while Q10 also significantly inhibited EGF activity.

In a preferred embodiment describing HER2 inhibitors $R_{21}$ is hydrogen, OH, SH, or halogen, preferably hydrogen or OH; $R_{22}$ is hydrogen; $R_{23}$ is hydrogen; $R_{24}$ is hydrogen, OH, SH, or halogen, preferably Cl or OH; $R_{25}$ is hydrogen; $R_{26}$ is either $CH_2$ or NH; and $R_{27}$ is a mono-substituted phenyl group where the substituent is $COOCH_3$ or $N=C(CN)_2$.

E. Additional Compounds

The present disclosure also relates to the identification of other specific compounds belonging to the classes and groups described herein which are useful in the present invention. Identification can be carried out by assaying the ability of a compound to inhibit receptor tyrosine kinase activity, and preferably, the ability of the compound to inhibit growth of cells having a receptor tyrosine kinase driven disorder. Such assays can be preformed as described in the art, or as described in the examples below.

For example, cellular kinase assays are described below for HER2, EGFR and PDGFR, as are in vitro soft agar assays for HER2 driven cancers. The same type of soft agar assays can be used to test the ability of a compound to inhibit EGFR or PDGFR using suitable cell lines.

Examples of cell lines which can be used to study the effect of a compound, for example in vitro or in animal models, include the following: cells characterized by overactivity of HER2 include SKOV3 (ATCC# HTB77), Calu3 (ATCC# HTB25), MVA361 (ATCC# HTB27), and SW626 (ATCC# HTB78) ; cell lines characterized by inappropriate activity of PDGFR such as human glioblastoma cell line T98G; and cell lines characterized by inappropriate activity of EGFR such as A431 (ATTC# CRL1555) and KB (ATTC# CCL17). One skilled in the art can choose other suitable cell lines using standard techniques and the present application as a guide. For example, the diagnostic section described infra can be used to help determine whether a cell line (e.g., a tumor cell line) is driven by a tyrosine receptor kinase such as HER-2.

Animal model systems can also be used to further measure the therapeutic effect of a compound. Examples of suitable animal models include subcutaneous xenograft model and in situ mammary fat pad model.

1. Xenograft Model

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice by Rygaard and Povlsen (Rygaard, J. and Povlsen, C. O., Acta Pathol. Microbial. Scand., 77:758–760, 1969.), many different human tumor cell lines (e.g., mammary, lung, genitourinary, gastrointestinal, head and neck, glioblastoma, bone, and malignant melanomas) have been transplanted and successfully grown in nude mice. Human mammary tumor cell lines, including MCF-7, ZR75-1, and MDA-MB-231, have been established as subcutaneous xenografts in nude mice (Warri, A. M., et al, Int. J. Cancer, 49:616–623, 1991; Ozzello, L. and Sordat, M., Eur. J. Cancer, 16:553–559, 1980; Osborne, C. K., et al, Cancer Res., 45:584–590, 1985; Seibert, K., et al, Cancer Res., 43:2223–2239, 1983).

To study the effect of anti-tumor drug candidates on HER2 expressing tumors, the tumor cells should be able to grow in the absence of supplemental estrogen. Many mammary cell lines are dependent on estrogen for in vivo growth in nude mice (Osborne et al., supra), however, exogenous estrogen suppresses her2 expression in nude mice (Warri et al., supra, Dati, C., et al, Oncogene, 5:1001–1006, 1990). For example, in the presence of estrogen, MCF-7, ZR-75-1, and T47D cells grow well in vivo, but express very low levels of HER2 (Warri et al., supra, Dati, C., et al, Oncogene, 5:1001–1006).

The following type of xenograft protocol can be used: 1) implant tumor cells (subcutaneously) into the hindflank of five- to six-week-old female Balb/c nu/nu athymic mice; 2) administer the anti-tumor compound; 3) measure tumor growth by measuring tumor volume. The tumors can also be analyzed for the presence of a receptor, such as HER2, EGF or PDGF, by Western and immunohistochemical analyses. Using techniques known in the art, one skilled in the art can vary the above procedures, for example through the use of different treatment regimes.

2. Mammary Fat Pad Model

The mammary fat pad model is particularly useful for measuring the efficacy of compounds which inhibit HER2, because of the role HER2 plays in breast cancer. By implanting tumor cells directly into the location of interest, in situ models more accurately reflect the biology of tumor development than do subcutaneous models. Human mammary cell lines, including MCF-7, have been grown in the mammary fat pad of athymic mice (Shafie, S. M. and Grantham, F. H., *J. Natl. Cancer Instit.*, 67:51–56, 1981; Gottardis, M. M., et al, *J. Steroid Biochem.*, 30:311–314, 1988). For example the following procedure can be used: 1) MDA-MB-231 and MCF-7 cells transfected with her2 are implanted at various concentrations into the axillary mammary fat pads of female athymic mice; 2) the compound is administered; and 3) tumor growth is measured at various time points. The tumors can also be analyzed for the presence of a receptor such as HER2, by Western and immunohistochemical analyses. Using techniques known in the art, one skilled in the art can vary the above procedures, for example through the use of different treatment regimes.

F. Further Analysis

Therapeutic compounds should be more potent in inhibiting receptor tyrosine kinase activity than in exerting a cytotoxic effect. A measure of the effectiveness and cell toxicity of a compound can be obtained by determining the therapeutic index: $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques, such as using an MTT assay as described by Mossman *J. Immunol. Methods* 65:55–63 (1983), by measuring the amount of LDH released (Korzeniewski and Callewaert, *J. Immunol. Methods* 64:313 (1983); Decker and Lohmann-Matthes, *J. Immunol. Methods* 115:61 (1988), or by measuring the lethal dose in animal models. Compounds with a large therapeutic index are preferred. The therapeutic index should be greater than 2, preferably at least 10, more preferably at least 50.

In addition to measuring tumor growth to achieve a compound range which can safely be administered to a patient in the animal models, plasma half-life and biodistribution of the drug and metabolites in plasma, tumors, and major organs can be determined to facilitate the selection of drugs most appropriate for the inhibition of a disorder. Such measurements can be carried out, for example, using HPLC analysis. Compounds that show potent inhibitory activity in the screening assays, but have poor pharmacokinetic characteristics, can be optimized by altering the chemical structure and retesting. In this regard, compounds displaying good pharmacokinetic characteristics can be used as model.

Toxicity studies can also be carried out by measuring the blood cell composition. For example, toxicity studies can be carried out as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition, and the percent of lymphocytes versus polymorphonuclear cells. A comparison of results for each dosing regime with the controls indicates if toxicity is present.

At the termination of each study, further studies can be carried out by sacrificing the animals (preferably, in accordance with the American Veterinary Medical Association guidelines Report of the American Veterinary Medical Assoc. Panel on Euthanasia. *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components less preferred, as are compounds having an adverse effect on major organs. In general, the greater the adverse effect the less preferred the compound.

III. Cell Proliferative Disorders

Cell proliferative disorders which can be treated or further studied by the present invention include cancers, blood vessel proliferative disorders, and fibrotic disorders. These disorders are not necessarily independent. For example, fibrotic disorders may be related to, or overlap, with blood vessel proliferative disorders. For example, atherosclerosis (which is characterized herein as a blood vessel disorder) results, in part, in the abnormal formation of fibrous tissue.

Blood vessel proliferation disorders refer to angiogenic and vasculogenic disorders generally resulting in abnormal proliferation of blood vessels. The formation and spreading of blood vessels, or vasculogenesis and angiogenesis respectively, play important roles in a variety of physiological processes such as embryonic development, wound healing and organ regeneration. They also play a role in cancer development. Examples of blood vessels disorders include restenosis, retinopathies, and atherosclerosis.

Fibrotic disorders refer to the abnormal formation of extracellular matrix. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. PDGFR has been implicated in the maintenance of mesangial cell proliferation. (Floege, J. et al., *Kidney International* 43S:47–54 (1993).)

The primary focus of the present disclosure in on HER2 and EGFR driven cancers. A cancer cell refers to various types of malignant neoplasms, most of which can invade surrounding tissues, and may metastasize to different sites, as defined by Stedman's Medical Dictionary 25th edition (Hensyl ed. 1990).

A. HER2 Cell Proliferation Disorders

HER2 driven disorders are characterized by inappropriate or over-activity of HER2. Inappropriate HER-2 activity refers to either: 1) HER2 expression in cells which normally do not express HER2; 2) increased HER-2 expression leading to unwanted cell proliferation such as cancer; 3) increased HER-2 activity leading to unwanted cell proliferation, such as cancer; and/or over-activity of HER-2.

Over-activity of HER2 refers to either an amplification of the gene encoding HER2 or the production of a level of HER2 activity which can be correlated with a cell proliferative disorder (i.e., as the level of HER2 increases the severity of one or more of the symptoms of the cell proliferative disorder increases).

The HER-2 protein is a member of the class I receptor tyrosine kinase (RTK) family. Yarden and Ullrich, *Annu. Rev. Biochem.* 57:443, 1988; Ullrich and Schlessinger, *Cell* 61:203, 1990. HER-2 protein is structurally related to EGF-R, p180(HER-3), and pl80(HER-4). Carraway, et al ., *Cell* 78:5, 1994; Carraway, et al., *J. Biol. Chem.* 269:14303, 1994. These receptors share a common molecular architecture and contain two cysteine-rich regions within their cytoplasmic domains and structurally related enzymatic regions within their cytoplasmic domains.

Activation of HER-2 protein can be caused by different events such as ligand-stimulated homo-dimerization, ligand-stimulated hetero-dimerization and ligand-independent homo-dimerization. Ligand-stimulated hetero-dimerization appears to be induced by EGF-R to form EGF-R/HER-2 complexes and by neu differentiation factor/heregulin (NDF/HRG) to form HER-2/ HER-3 and/or HER-2/ HER-4 complexes. Wada et al., *Cell* 61:1339, 1990; Slikowski et al., *J. Biol. Chem.* 269:14661, 1994; Plowman et al., *Nature* 266:473, 1993. Ligand-dependent activation of HER-2 protein is thought to be mediated by neu-activating factor (NAF) which can directly bind to p185(HER-2) and stimulate enzymatic activity. Dougall et al., *Oncogene* 9:2109, 1994; Samata et al., *Proc. Natl. Acad. Sci. USA* 91:1711, 1994. Ligand-independent homo-dimerization of HER-2 protein and resulting receptor activation is facilitated by over-expression of HER-2 protein.

Receptor tyrosine kinases are involved in various cellular signaling pathways. Receptor phosphorylation stimulates a physical association of the activated receptor with target molecules. Receptor tyrosine kinase substrates and adaptor proteins (also known as docking proteins) are both involved in signal transduction from an activated receptor tyrosine kinase. A receptor tyrosine kinase substrate is phosphorylated by the receptor tyrosine kinase and can then act on another cellular protein. An adaptor protein, such as Grb-2, binds a receptor tyrosine kinase and to another protein helping to activate the other protein or modulate its subcellular location. Substrates and adaptor proteins typically bind to receptor tyrosine kinases by SH2 and SH3 domains. Pawson and Schlessinger, *Current Biology* 3:434, 1993.

HER-2 protein substrates are acted upon by activated HER-2 complexes such as HER-2/EGF-R, HER-2/HER-2, HER-2/ HER-3, and HER-2/HER-4 activated complexes. An activated HER-2 complex acts as a phosphokinase and phosphorylates different cytoplasmic proteins. Examples of HER-2 substrates include, IP$_3$ kinase and PI 4-kinase. Scott et al., *Journal of Biological Chemistry* 22:14300, 1991.

HER-2 adaptor proteins bind to an activated HER-2 complex and then another protein. For example, GRB-7 binding to a HER-2 complex may be sufficient to initiate the GRB-7 signaling pathway without phosphorylation. Stein et al., *EMBO Journal* 13:1331, 1993.

Thus, HER-2 protein activities include: (1) phosphorylation of HER-2 protein, HER-3 protein or HER-4 protein; (2) phosphorylation of a HER-2 protein substrate; (3) interaction with a HER-2 adapter protein; and/or (4) HER-2 protein surface expression. Additional HER-2 protein activities can be identified using standard techniques. For example, a partial agonistic monoclonal antibody recognizing HER-2 protein can be used to activate HER-2 protein and examine signal transduction of HER-2 protein. Scott et al., *Journal of Biological Chemistry* 22:14300, 1991.

HER2 activity can be assayed by measuring one or more of the following activities: (1) phosphorylation of HER2; (2) phosphorylation of a HER2 substrate; (3) activation of an HER2 adapter molecule; and (4) increased cell division. These activities can be measured using techniques described below and known in the art.

Treatment of patients suffering from a HER2 disorder is facilitated by first determining whether the cell proliferative disorder is characterized by an over-activity of HER2. After the disorder is identified, patients suffering from such a disorder can be identified by analysis of their symptoms using procedures well known to medical doctors. Such identified patients can then be treated as described herein.

HER2 driven disorders are typically cell proliferative disorders such as cancers. HER2 driven disorders appear to be responsible for a sub-population of different types of cancers. For example, as noted above, Slamon et al., found about 30% of breast cancer cells to have increased HER2 gene expression. Slamon et al., also found a correlation between her2 (c-erbB-2) amplification and poor patient prognosis.

The use of the present invention to treat breast cancer is preferred because of the prevalence and severity of breast cancer. Carcinoma of the breast is the most common cancer among women and their second leading cause of cancer death (Marshall, E., *Science* 259:618–621, 1993). The incidence of breast cancer has been increasing over the past several decades (Marshall, supra, and Harris, J. R., et al, *New Engl. J . Med.*, 327(5):319–328, 1992).

In addition to breast cancers, increased HER2 activity or gene expression has been associated with certain types of blood cancers, stomach adenocarcinomas, salivary gland adenocarcinomas, endometrial cancers, ovarian adenocarcinomas, gastric cancers, colorectal cancers, non-small cell lung cancer, and glioblastomas. The methods described herein can be used to identify the sub-populations of these different cancers which are characterized by over-activity of HER2.

B. EGFR Disorders

Some of the featured compounds can be used to treat cell proliferative disorders characterized by inappropriate EGFR activity. "Inappropriate EGFR" activity refers to either: 1) EGF-receptor (EGFR) expression in cells which normally do not express EGFR; 2) EGF expression by cells which normally do not express EGF; 3) increased EGF-receptor (EGFR) expression leading to unwanted cell proliferation; 4) increased EGF expression leading to unwanted cell proliferation; and/or 5) muta- tions leading to constitutive activation of EGF-receptor (EGFR). The existence of inappropriate or abnormal EGF and EGFR levels or activities is determined by procedures well known in the art.

An increase in EGF activity or expression is characterized by an increase in one or more of the activities which can occur upon EGF ligand binding such as: (1) EGF-R dimerization; (2) auto-phosphorylation of EGFR, (3) phosphorylation of an EGFR substrate (e.g., PLCλ, see Fry supra), (4) activation of an adapter molecule, and/or (5) increased cell division. These activities can be measured using techniques described below and known in the art. For example auto-phosphorylation of EGFR can be measured as described in the examples below using an anti-phosphotyrosine antibody, and increased cell division can be performed by measuring $^3$H-thymidine incorporation into DNA. Preferably, the increase in EGFR activity is characterized by an increased amount of phosphorylated EGFR and/or DNA synthesis.

Unwanted cell proliferation can result from inappropriate EGFR activity occurring in different types of cells including cancer cells, cells surrounding a cancer cell, and endothelial cells. Examples of disorders characterized by inappropriate EGF activity include cancers such as glioma, head, neck, gastric, lung, breast, ovarian, colon, and prostate; and other types of cell proliferative disorders such as psoriasis.

IV. Administration Of Featured Compounds

The compounds of this invention can be administered to a patient alone, or in a pharmaceutical composition comprising the active compound and a carrier or excipient. The compounds can be prepared as pharmaceutically acceptable salts (i.e., non-toxic salts which do not prevent the compound from exerting its effect).

Pharmaceutically acceptable salts can be acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See, e.g., supra. PCT/US92/03736) . Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents. The compounds or pharmaceutical compositions can be administered by different routes including intravenously, intraperitoneally, subcutaneously, and intramuscularly; orally, topically, or transmucosally.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. The compound described herein may be formulated for parenteral administration, such as by intravenous injection. The compounds can also be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external icroenvironment and, because liposomes fuse with cell membranes, are efficiently delivered into the cell cytoplasm. Additionally, due to their hydrophobicity, many small organic molecules may be directly administered intracellularly.

Pharmaceutical compositions suitable for use in the present invention include compositions wherein the active ingredients are contained in an effective amount to achieve its intended purpose. Determination of the effective amounts is within the capability of those skilled in the art, especially in light of the detailed disclosure provided herein.

The pharmaceutical compositions of the present invention may be manufactured in different manners such as conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained, for example by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents may be added, such as the cross-linked polyvinyl pyrrolidone, agar, or alginic acid or a salt thereof such as sodium alginate.

Dragee cores should be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Therapeutically effective doses for the compounds described herein can be estimated initially from cell culture and animal models. For example, a dose can be formulated in animal models to achieve a circulating concentration range that includes the $IC_{50}$ as determined in cell culture assays. Such information can be used to more accurately determine useful doses in humans.

An example of a physiologically carrier is PBTE:D5W. PBTE consists of a solution of 3% w/v benzyl alcohol, 8% w/v polysorbate 80, and 65°. w/v polyethylene glycol (MW= 300 daltons) in absolute ethanol. PBTE:D5W consists of PBTE diluted 1:1 in a solution of 5% dextrose in water.

The use of hydrophobic compounds can be facilitated by different techniques such as combining the compound with a carrier to increase the solubility of the compound and using frequent small daily doses rather than a few large daily doses. For example, the composition can be administered at short time intervals such as by the methods described above or using a pump to control the time interval or achieve continuous administration.

Suitable pumps are commercially available (e.g., the ALZET® pump sold by Alza corporation and the BARD ambulatory PCA pump sold by Bard MedSystems).

The proper dosage depends on various factors such as the type of disease being treated, the particular composition being used, and the size and physiological condition of the patient. For the treatment of cancers the expected daily dose is between 1 to 2000 mg/day, preferably 1 to 250 mg/day, and most preferably 10 to 150 mg/day. Drugs can be delivered less frequently provided plasma levels of the active moiety are sufficient to maintain therapeutic effectiveness.

A factor which can influence the drug dose is body weight. Drugs should be administered at doses ranging from 0.02 to 25 mg/kg/day, preferably 0.02 to 15 mg/kg/-day, most preferably 0.2 to 15 mg/kg/day. Alternatively, drugs can be administered at 0.5 to 1200 mg/m$^2$/day, preferably 0.5 to 150 mg/m$^2$/day, most preferably 5 to 100 mg/m$^2$/day. The average plasma level should be 50 to 5000 $\mu$g/ml, preferably 50 to 1000 $\mu$g/ml, and most preferably 100 to 500 $\mu$g/ml. Plasma levels may be reduced if pharmacological effective concentrations of the drug are achieved at the site of interest.

V. Combination Treatment

The receptor tyrosine kinase inhibitory compounds described herein can be used alone, in combination with other agents able to inhibit protein kinase activity (e.g., anti-sense nucleic acid and ribozymes targeted to nucleic acid encoding a receptor tyrosine kinase, and antibodies able to modulate tyrosine kinase activity, such as anti-HER-2 antibodies which may work by modulating HER-2 activity as described by Hudziak et al., *Mol. Cell. Biol.* 9:1165, 1989; Sarup et al., *Growth Regulation* 1:71, 1991; and Shepard et al., *J. clinical Immunology* 11:117, 1991) and in combination with other types of treatment for cell proliferative disorders.

For example, various different types of general treatments are currently used to treat different types of cancer patients. These general treatments are based on the cancer type and do not specifically target receptor tyrosine kinase activity.

Different chemotherapeutic agents are known in art for treating breast cancer. Cytoxic agents used for treating breast cancer include doxorubicin, cyclophosphamide, methotrexate, 5-fluorouracil, mitomycin C, mitoxantrone, taxol, and epirubicin. *CANCER SURVEYS, Breast Cancer* volume 18, Cold Spring Harbor Laboratory Press, 1993, Another example is the use of different chemotherapeutic agents are used to treat different types of leukemia. O'Rourke and Kalter *Leukemia*, In: *Clinical Oncology*, Eds. Weiss, Appleton and Lange; Norwalk Conn, 1993; Mitus and Rosenthal, *Adult Leukemia*, In: *American Society Textbook of Clinical Oncology*, chapter 30, Eds. Holleb, Fink, and Murphy; and Pui and Rivera, *Infant Leukemia*, In: *American Society Textbook of Clinical Oncology*, chapter 31, Eds. Holleb, Fink, and Murphy; (these references are hereby incorporated by reference herein). Examples of chemotherapeutic agents include treatment of AML using daunorubicin, cytarabine (Ara-C), doxorubicin, amsacrine, mitoxantrone, etoposide (VP-16), thioguanine, mercaptopurine, and azacytidine; treatment of ALL using vincristine, prednisone, doxorubicin and asparginase; treatment of CML using busulfan and hydroxyurea; and treatment of CLL using chlorambucil and cyclophosphamide. Additional treatments include use of alpha-interferon, bone marrow transplantation and transplantation of peripheral blood or umbilical cord blood stem cells.

VI. Diagnostic uses

Another use of the compounds described herein is to help diagnose whether a disorder is driven, to some extent, by a particular receptor tyrosine kinase. Some cancers may be driven by more than one receptor tyrosine kinases. For example, Wada et al., *Oncogene* 5:489–495, 1990, describes co-expression of EGFR and HER2.

A diagnostic assay to determine whether a particular cancer is driven by a specific receptor can be carried out using the following steps: 1) culturing test cells or tissues; 2) administering a compound which can inhibit one or more receptor tyrosine kinase; and 3) measuring the degree of growth inhibition of the test cells.

These steps can be carried out using standard techniques in light of the present disclosure. For example, standard techniques can be used to isolate cells or tissues and culturing in vitro or in vivo. An example of an in vitro assay is a cellular kinase assay as described below. An example of an in vivo assay is a xenograft experiment where the cells or tissues are implanted into another host such as a mouse.

Compounds of varying degree of selectivity are useful for diagnosing the role of a receptor tyrosine kinase. For example, compounds which inhibit more than one type of receptor tyrosine kinase can be used as an initial test compound to determine if one of several receptor tyrosine kinases drive the disorder. More selective compounds can then be used to further eliminate the possible role of different receptor tyrosine kinases in driving the disorder. Test compounds should be more potent in inhibiting receptor tyrosine kinase activity than in exerting a cytotoxic effect (e.g., an $IC_{50}/LD_{50}$ of greater than one). As noted above, in section II.F. infra $IC_{50}$ and $LD_{50}$ can be measured by standard techniques, such as described in the present application and using an MTT assay as described by Mossman supra, or by measuring the amount of LDH released (Korzeniewski and Callewaert, J. supra; Decker and Lohmann-Matthes, supra) . The degree of $IC_{50}/LD_{50}$ of a compound should be taken into account in evaluating the diagnostic assay. Generally, the larger the ratio the more reliable the information. Appropriate controls to take into account the possible cytotoxic effect of a compound, such as treating cells not associated with a cell proliferative disorder (e.g., control cells) with a test compound, can also be used as part of the diagnostic assay.

VII. Examples

Examples are provided below to illustrate different aspects and embodiments of the present invention. These examples are not intended in any way to limit the disclosed invention. Rather, they illustrate methodology by which drugs having the disclosed formulas can be readily identified by routine procedure to ensure that they have the desired activity, and the synthesis of different compounds described herein. Compounds within a formula claimed herein can be screened to determine those with the most appropriate activity prior to administration to an animal or human. Other compounds can also be screened to determine suitability for use in methods of this invention.

Example 1:
Inhibition of Tyrosine Kinase Activity and Tumor Cell Growth

This example illustrates the ability of the exemplary compounds to inhibit receptor tyrosine kinases, such as HER2 and/or EGFR. The following target cells were used for cellular kinase assays: NIH3T3 clone C7 (Honegger et al., supra) engineered to over-express human EGF receptor; NIH3T3 cells engineered to over-express a chimeric receptor containing the EGFR extracellular domain and the HER2 intracellular kinase domain; the human mammary carcinoma line BT474 (ATCC HTB2) expressing HER2; and the human glioblastoma line U1242 that expresses PDGFR-$\beta$. Growth assays were carried out using human mammary epithelial SKBR3 (ATCC HTB30) cells, SKOV3 (ATCC HTB77) human ovarian cancer cell line, A431 cells, MCF7 human breast carcinoma cells, MCF7 cells overexpress the HER2 kinase (MCF7-HER2), NIH3T3 cells, and NIH3T3 cells overexpressing the HER2 kinase (3T3-HER2).

SKBR3 cells over-express HER2. A431 cells over-express EGFR. These cells were dispensed into 96-well plates with test compounds. After 4 days the monolayers were TCA-fixed then stained with sulphorhodamine B. The absorbance versus log drug concentration was plotted and $IC_{50}$ values estimated.

SKOV3 cells also over-express HER2. These cells were plated into soft agar with a test compound and colony growth was quantified 2 weeks later using an Omnicon colony counter.

A. Methods

Unless otherwise stated the effect of various compounds on receptor tyrosine kinases were assayed as described in this section.

1. EGF-receptor Whole Cell Kinase Assay

EGFR kinase activity (EGFR-3T3 assay) in whole cells was measured as described below:

Materials & Reagents

1) EGF Ligand: stock concentration=16.5 $\mu$M; EGF 201, TOYOBO, Co., Ltd. Japan.
2) 05-101 (UBI) (a monoclonal antibody recognizing an EGFR extracellular domain).
3) Anti-Phosphotyosine antibody (polyclonal).
4) TAGO antibody: Goat anti-rabbit IgG horse radish peroxidase conjugate, TAGO, Inc., Burlingame, Calif.

| 5) | TBST buffer: | Tris-HCl, pH 7.2 | 50 mM |
|---|---|---|---|
|  |  | NaCl | 150 mM |
|  |  | Triton X-100 | 0.1% |
| 6) | HNTG 5X stock: | HEPES | 0.1 M |
|  |  | NaCl | 0.75 M |
|  |  | Glycerol | 50% |
|  |  | Triton X-100 | 1.0% |
| 7) | ABTS stock: | Citric Acid | 100 mM |
|  |  | $Na_2HPO_4$ | 250 mM |
|  |  | HCl, conc. | 4.0 pH |
|  |  | ABTS* | 0.5 mg/ml |

*(2,2'-azinobis(3-ethylbenzthiazolinesulfonic acid). Keep solution in dark at 4° C. until use.

8) Stock reagents of:
 EDTA 100 mM pH 7.0
 $Na_3VO_4$ 0.5M
 $Na_4PO_7$ 0.2M

Procedure

The following protocol was used:
I. Pre-coat ELISA Plate

A. Coat ELISA plates (Corning, 96 well, Cat. #25805-96) with 05-101 antibody at 0.5 $\mu$g per well in PBS, 150 $\mu$l final volume/well, and store overnight at 4° C. Coated plates are good for up to 10 days when stored at 4° C.

B. On day of use, remove coating buffer and replace with blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

II. Seeding Cells

A. EGFR/C7 cell line (Honegger, et al., *Cell* 51:199–209, 1987) can be use for this assay.

B. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm, and once at room temperature for 5 minutes.

C. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 $\mu$l per well, in a 96 well microtiter plate. Incubate seeded cells in 5% $CO_2$ at 37° C. for about 40 hours.

III. Assay Procedures.

A. Check seeded cells for contamination using an inverted microscope. Dilute drug stock (10 mg/ml in DMSO) 1:10 in DMEM medium, then transfer 5 $\mu$l to a test well for a final drug dilution of 1:200 and a final DMSO concentration of 1%. Control wells receive DMSO alone. Incubate in 5% $CO_2$ at 37° C. for one hour.

B. Prepare EGF ligand: dilute stock EGF in DMEM so that upon transfer of 10 $\mu$l dilute EGF (1:12 dilution), 25 nM final concentration is attained. C. Prepare fresh HNTG* sufficient for 100 $\mu$l per well; and place on ice.

HNTG*: 10 ml

| HNTG stock | 2.0 ml |
|---|---|
| milli-Q $H_2O$ | 7.3 ml |
| EDTA, 100 mN, pH 7.0 | 0.5 ml |
| $Na_3VO_4$, 0.5 M | 0.1 ml |
| $Na_4PO_7$, 0.2 M | 0.1 ml |

D. After two hours incubation with drug, add prepared EGF ligand to cells, 10 $\mu$l per well, to yield a final concentration of 25 nM. Control wells receive DMEM alone. Incubate, shaking, at room temperature, for 5 minutes.

E. Remove drug, EGF, and DMEM. Wash cells twice with PBS. Transfer HNTG* to cells, 100 $\mu$l per well. Place on ice for 5 minutes. Meanwhile, remove blocking buffer from other ELISA plate and wash with TEST as described above.

F. With a pipette tip securely fitted to a micropipettor, scrape cells from plate and homogenize cell material by repeatedly aspirating and dispensing the HNTG* lysis buffer. Transfer lysate to a coated, blocked, and washed BLISA plate. Incubate shaking at room temperature for one hour.

G. Remove lysate and wash 4 times with TBST. Transfer freshly diluted anti-Ptyr antibody to ELISA plate at 100 $\mu$l per well. Incubate shaking at room temperature for 30 minutes in the presence of the anti-Ptyr antiserum (1:3000 dilution in TBST).

H. Remove the anti-Ptyr antibody and wash 4 times with TEST. Transfer the freshly diluted TAGO anti-rabbit IgG antibody to the ELISA plate at 100 $\mu$l per well. Incubate shaking at room temperature for 30 minutes. anti-rabbit IgG antibody: 1:3000 dilution in TBST I. Remove TAGO detection antibody and wash 4 times with TBST. Transfer freshly prepared ABTS/$H_2O_2$ solution to ELISA plate, 100 μl per well. Incubate at room temperature for 20 minutes. ABTS/$H_2O_2$ solution: 1.2 μl 30% $H_2O_2$ in 10 ml ABTS stock.

J. Stop reaction by adding 50 μl 5N $H_2SO_4$ (optional) and determine O.D. at 410 nm.

K. The maximal phosphotyrosine signal is determined by subtracting the value of the negative controls from the positive controls. The percent inhibition of phosphotyrosine content for extract-containing wells is then calculated, after subtraction of the negative controls.

2. EGFR-HER2 chimeric receptor

HER2 kinase activity (EGFR-3T3) in whole cells was measured as described below:

Materials & Reagents

1) EGF Ligand: stock concentration=16.5 μM; EGF 201, TOYOBO, Co., Ltd. Japan.
2) 05-101 (UBI) (a monoclonal antibody recognizing an EGFR extracellular domain).
3) Anti-Phosphotyosine antibody (polyclonal).
4) TAGO antibody: Goat anti-rabbit IgG horse radish peroxidase conjugate, TAGO, Inc., Burlingame, Calif.

| 5) | TBST buffer: | Tris-HCl, pH 7.2 | 50 mM |
|---|---|---|---|
| | | NaCl | 150 mM |
| | | Triton X-100 | 0.1% |
| 6) | HNTG 5X stock: | HEPES | 0.1 M |
| | | NaCl | 0.75 M |
| | | Glycerol | 50% |
| | | Triton X-100 | 1.0% |
| 7) | ABTS stock: | Citric Acid | 100 mM |
| | | $Na_2HPO_4$ | 250 mM |
| | | HCl, conc. | 0.5 pH |
| | | ABTS* | 0.5 mg/ml |

*(2,2'-azinobis(3-ethylbenzthiazolinesulfonic acid). Keep solution in dark at 4° C. until use.

8) Stock reagents of:
EDTA 100 mM pH 7.0
$Na_3VO_4$ 0.5M
$Na_4PO_7$ 0.2M

Procedure

The following protocol was used:

I. Pre-coat ELISA Plate

A. Coat ELISA plates (Corning, 96 well, Cat. #25805-96) with 05-101 antibody at 0.5 μg per well in PBS, 100 μl final volume/well, and store overnight at 4° C. Coated plates are good for up to 10 days when stored at 4° C.

B. On day of use, remove coating buffer and replace with 100 μl blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

II. Seeding Cells

A. An NIH3T3 cell line overexpressing a chimeric receptor containing the EGFR extracellular domain and extracellular HER2 kinase domain can be used for this assay.

B. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm, at room temperature for 5 minutes.

C. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 μl per well, in a 96 well microtiter plate. Incubate seeded cells in 5% $CO_2$ at 37° C. for about 40 hours.

III. Assay Procedures

A. Check seeded cells for contamination using an inverted microscope. Dilute drug stock (10 mg/ml in DMSO) 1:10 in DMEM medium, then transfer 5 μl to a test well for a final drug dilution of 1:200 and a final DMSO concentration of 1%. Control wells receive DMSO alone. Incubate in 5% $CO_2$ at 37° C. for two hours.

B. Prepare EGF ligand: dilute stock EGF in DMEM so that upon transfer of 10 μl dilute EGF (1:12 dilution), 100 nM final concentration is attained.

C. Prepare fresh HNTG* sufficient for 100 μl per well; and place on ice.
HNTG*: 10 ml

| HNTG*: | 10 ml |
|---|---|
| HNTG stock | 2.0 ml |
| milli-Q $H_2O$ | 7.3 ml |
| EDTA, 100 mM, pH 7.0 | 0.5 ml |
| $Na_3VO_4$, 0.5 M | 0.1 ml |
| $Na_4PO_7$, 0.2 M | 0.1 ml |

D. After 120 minutes incubation with drug, add prepared EGF ligand to cells, 10 μl per well, to a final concentration of 100 nM. Control wells receive DMEM alone. Incubate, shaking, at room temperature, for 5 minutes.

E. Remove drug, EGF, and DMEM. Wash cells twice with PBS. Transfer HNTG* to cells, 100 μl per well. Place on ice for 5 minutes. Meanwhile, remove blocking buffer from other ELISA plate and wash with TBST as described above.

F. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.

G. Remove lysate and wash 4 times with TBST. Transfer freshly diluted anti-Ptyr antibody to ELISA plate at 100 μl per well. Incubate shaking at room temperature for 30 minutes in the presence of the anti-Ptyr antiserum (1:3000 dilution in TBST).

H. Remove the anti-Ptyr antibody and wash 4 times with TBST. Transfer the freshly diluted TAGO anti-rabbit IgG antibody to the ELISA plate at 100 μl per well. Incubate shaking at room temperature for 30 minutes. anti-rabbit IgG antibody: 1:3000 dilution in TBST I. Remove TAGO detection antibody and wash 4 times with TBST. Transfer freshly prepared ABTS/$H_2O_2$ solution to ELISA plate, 100 μl per well.

Incubate shaking at room temperature for 20 minutes. ABTS/$H_2O_2$ solution: 1.0 μl 30% $H_2O_2$ in 10 ml ABTS stock.

J. Stop reaction by adding 50 μl 5N $H_2SO_4$ (optional), and determine O.D. at 410 nm.

K. The maximal phosphotyrosine signal is determined by subtracting the value of the negative controls from the positive controls. The percent inhibition of phosphotyrosine content for extract-containing wells is then calculated, after subtraction of the negative controls.

3. HER2-ELISA

HER2-BT474 assays measuring whole cell HER2 activity was carried out as described below:

Materials & Reagents

1. The cell line used in this assay is BT-474 (ATCC HBT20), a human breast tumor cell line which expresses high levels of HER2 kinase.
2. BT-474 is grown in an incubator with 5% $CO_2$ at 37° C. The growth media is RPMI+10% FBS+GMS-G (Gibco supplement)+Glutamine.
3. A monoclonal anti-HER2 antibody is used in ELISA.

| D-PBS: | $KH_2PO_4$ | 0.20 g/l |
|---|---|---|
| (GIBCO, 310-4190AJ) | $K_2HPO_4$ | 2.16 g/l |
| | KCl | 0.20 g/l |
| | NaCl | 8.00 g/l |
| | pH 7.2 | |

5. Blocking Buffer: TBST plus 5% Milk (Carnation Instant Non-Fat Dry Milk).

| TBST buffer: | Tris-HCl | 50 mM |
|---|---|---|
| | NaCl | 150 mM |
| | pH 7.2 | (HCl, 10 N) |
| | Triton X-100 | 0.1% |

Stock solution of TBS (10X) is prepared, and Triton X-100 is added to the buffer during dilution.

| HNTG buffer: | HEPES | 20 mM |
|---|---|---|
| | NaCl | 150 mM |
| | pH 7.2 | (HCl, 1 N) |
| | Glycerol | 10% |
| | Triton X-100 | 0.2% |

Stock solution (5X) is prepared and kept in 4° C.
8. EDTA-HCl: 0.5M pH 7.0 (10N HCl) as 500X stock.
9. $Na_3VO_4$: 0.5M as 100X stock is kept at −80° C. as aliquots.
10. $Na_4P_2O_7$: 0.2M as 100X stock.
11. Polyclonal antiserum anti-phosphotyrosine.
12. Goat anti-rabbit IgG, horse raddish peroxidase (POD) conjugate, Tago (Cat. No. 4520; Lot No. 1802): Tago, Inc., Burlingame, Calif.

| ABTS solution: | Citric acid | 100 mM |
|---|---|---|
| | $Na_2HPO_4$ | 250 mM |
| | pH 4.0 | (1 N HCl) |
| | ABTS | 0.5 mg/ml |

ABTS: 2.2'-azinobis(3-ethylbenzthiazolinesulfonic acid).
ABTS solution should be kept in the dark at 4° C. The solution should be discarded when it turns green.
14. Hydrogen Peroxide: 30% solution is kept in dark and 4° C.

Procedure

All the following steps are at room temperature and aseptically, unless stated otherwise. All ELISA plate washing is by rinsing with distilled water three times and once with TBST.

1. Cell Seeding
   (a) Grow BT474 cells in tissue culture dishes (10 cm, Corning 25020-100) to 80–90% confluence and collect using Trypsin-EDTA (0.25%, GIBCO).
   (b) Resuspend the cells in fresh medium and transfer to 96-well tissue culture plates (Corning, 25806-96) at about 25,000–50,000 cells/well (100 μl/well). Incubate the cells in 5% $CO_2$ at 37° C. overnight.
2. ELISA Plate Coating and Blocking
   (a) Coat the ELISA plate (Corning 25805-96) with anti HER2 antibody at 0.5 μg/well in 150 μl PBS overnight at 4° C., and seal with parafilm. The antibody coated plates can be used up to 2 weeks, when stored at 4° C.
   (b) On the day of use, remove the coating solution, replace with 200 μl of Blocking Buffer, shake the plate, and then remove the blocking buffer and wash the plate just before adding lysate.
3. Assay Procedures
   (a) Test the drugs in serum-free condition. Before adding drugs, the old media is replaced with serum-free RPMI (90 μl/well).
   (b) Dilute drug stock (in 100% DMSO) 1:10 with RPMI, and transfer 10 μl/well of this solution to the cells to achieve a final drug DMSO concentration at 1%. Incubate the cells in 5% $CO_2$ at 37° C.
   (c) Prepare fresh cell lysis buffer (HNTG*)

| HNTG | 2 ml |
|---|---|
| EDTA | 0.2 ml |
| $Na_3VO_4$ | 0.1 ml |
| $Na_4P_2O_7$ | 0.1 ml |
| $H_2O$ | 7.3 ml |
| HNTG* | 10 ml |

(d) After drug preincubation for two hours remove all the solution from the plate, transfer HNTG* 100 μl/well to the cells, and shake for 10 minutes.
   (e) Use a 12-channel pipette to scrape the cells from the plate, and homogenize the lysate by repeat aspiration and dispensing. Transfer all the lysate to the ELISA plate and shake for 1 hour.
   (f) Remove the lysate, wash the plate, add anti-pTyr (1:3,000 with TBST) 100 μl/well, and shake for 30 minutes.
   (g) Remove anti-pTyr, wash the plate, add goat anti-rabbit IgG conjugated antibody (1:5,000 with TBST) 100 μl/well, and shake for 30 minutes.
   (h) Remove anti-rabbit IgG antibody, wash the plate, and add fresh ABTS/$H_2O_2$ (1.2 μl $H_2O_2$ to 10 ml ABTS) 100 μl/well to the plate to start color development, which usually takes 20 minutes.
   (i) Measure OD 410 nM, Dynatec MR5000.
4. PDGF-R Cellular Assay The PDGF cellular kinase assay was carried out as follows: cells are lysed in 0.2M Hepes, 0.15M NaCl, 10% V/V glycerol, 0.04% Triton X-100, 5 mM EDTA, 5 mM $Na^+$ vanadate and 2 mM $Na^+$ pyrophosphate; cell lysates are then added to an ELISA plate coated with an anti-PDGF receptor antibody (Genzyme); ELISA plates are coated at 0.5 μg of antibody/well in 150 μl of PBS for 18 hours at 4° C. prior to the addition of the lysate; the lysate is incubated in the coated plates for 1 hour and then washed four times in TBST (35 mM Tris-HCl pH 7.0, 0.15M NaCl, 0.1% Triton X-100); anti-phosphotyrosine antibody (100 μl in PBS) is added and the mixture is incubated for 30 minutes at room temperature; the wells were then washed four times in TBST, a secondary antibody conjugated to POD (TAGO) is added to each well, and the treated well are incubated for 30 minutes at room temperature; the wells are then washed four times in TBST, ABTS/$H_2O_2$ solution is added to each well and the wells are incubated for two minutes; absorbance is then measured at 410 nm.

5. Sulforhodamine B (SRB) Assay for Adherent Cells

Sulforhodamine B assays for measuring effects of test compounds on cell growth were based on procedures described by Skehan et al. *J. Natl. Cancer Inst.* 82:1107, 1990. Unless otherwise stated the assays were carried out aseptically as follows:

Material & Methods (1) Sulforhodamine B-Sigma Catalog #S-9012 Working solution: 0.4% Sulforhodamine B=4 gram/liter 1% Acetic Acid.
(2) Trichloroacetic Acid (TCA)-Fisher Catalog #A322 Working solution: 10% TCA=100 gram TCA+1 liter $H_2O$.
(3) Acetic Acid, Glacial-Fisher Catalog #A38 Working solution: 1% Acetic Acid=10 ml Acetic Acid +990 ml $H_2O$.
(4) Tris, crystallized free base-Fisher Catalog #BP152 Working solution: 10 mM tris=1.211 gram Trizma base/liter $H_2O$.

Procedure (5) Aspirate growth media from 96 well plate containing control cells or cell treated with compounds, rinse wells 2 or 3 times with PBS and layer 200 µl cold 10% TCA onto each well. Fix cells for 60 minutes at 4° C.
(6) Discard TCA and rinse wells 5 times with distilled $H_2O$. Dry plate upside down on paper towel.
(7) Stain fixed cells for 10 minutes with 100 µl 0.4% SRB per well.
(8) Pour off SRB solution and rinse wells 5 times with 1% acetic acid.
(9) Dry plate upside down on paper towel.
(10) After wells are completely dry, solubilize dye with 100 µl 10 mM Tris base per well for 5–10 minutes on titer plate shaker.
(11) Read optical density at dual wavelength mode 570 nm and 630 nm on Dynatech ELISA plate reader, Model MR 5000.

6. Soft Agar Assay Protocol

The soft agar assay is well known in the art as a method for measuring the effects of substances on cell growth. Unless otherwise stated the soft agar assays were carried out as follows:

Material & Reagents (1) A Water bath set at 39° C. and another water bath at 37° C.
(2) 2× assay medium is comprised of 2× Dulbecco's Modified Eagle's Medium (DMEM) (Gibco Cat. # CA400-4ANO3) supplemented by the following:
  20% Fetal Bovine Serum (FBS)
  2 mM Sodium Pyruvate
  4 mM Glutamine
  20 mM HEPES
  Non-essential Amino Acids (1:50 from 100x stock)
(3) 1× assay medium made of 1× DMEM supplemented with 10% FBS, 1 mM sodium pyruvate, 2 mM glutamine, 10 mM HEPES, non-essential amino acid (1:100 from 100x stock).
(4) 1.6% SeaPlaque Agarose in autoclave bottle
(5) Sterile 35 mm Corning plates (FMC Bioproducts Cat. #50102)
(6) Sterile 5 ml glass pipets (individually wrapped)
(7) Sterile 15 ml and 50 ml conical centrifuge tubes
(8) Pipets and sterile tips
(9) Sterile microcentrifuge tubes
(10) Cells in T75 flasks: SKOV-3 (ACTT HTB77).
(11) 0.25% Trypsin solution (Gibco # 25200-015).
(12) Procedure for making the base layer:
  (a) Have all the media warmed up in the 37° C. water bath.
  (b) To make 1× of assay medium+0.8% agar: make a 1:2 (vol:vol) dilution of melted agar (cooled to 39° C.), with 2× assay medium.
  (c) Keep all media with agar warm in the 39° C. water bath when not in use.
  (d) Dispense 1 ml of 1× assay medium+0.8% agar into dishes and gently swirl plate to form a uniform base layer. Bubbles should be avoided.
  (e) Refrigerate base layers to solidify (about 20 minutes) Base layers can be stored overnight in the refrigerator.
(13) Procedure for collecting cells:
  (a) Take out one flask per cell line from the incubator; aspirate off medium; wash once with PBS and aspirate off; add 3 ml of trypsin solution.
  (b) After all cells dissociate from the flask, add 3 ml of 1× assay media to inhibit trypsin activity. Pipet the cells up and down, then transfer the suspension into a 15 ml tube.
  (c) Determine the concentration of cells using a Coulter counter, and the viability by trypan blue exclusion.
  (d) Take out the appropriate volume needed to seed 3300 viable cells per plate and dilute it to 1.5 ml with 1× assay medium.
(14) Procedure for making the upper 0.4% agarose layer:
  (a) Add test compounds at twice the desired final assay concentration;+1.5 ml of cell suspension in 1× assay medium 10% FBS;+1.5 ml of 1× assay medium+0.8% agarose*: Total =3.0 ml 1× media 10% FBS+0.4% agarose with 3300 viable cells/ml, with and without test compounds.
(Made by 1:2 dilution of 2× media with 1.6% agar for the base layer procedure above.)
  (b) Plate 1 ml of the Assay Mix onto the 1 ml base layer. The duplicates are plated from the 3 ml volume.
  (c) Incubate the dishes for 2–3 weeks in a 100% humidified, 10% $CO_2$ incubator.
  (d) Colonies that are 60 microns and larger are scored positive.

6. MCF-7 SRB Growth Assay

MCF-7 cells are seeded at 2000 cells/ well in a 96-well flat bottom plate in normal growth media, which was 10% FBS/RPMI supplemented with 2 mM Glutamine. The plate of cells is incubated for about 24 hours at 37° C. after which it receives an equal volume of compound dilution per well making the total volume per well 200 µl. The compound is prepared at 2 times the desired highest final concentration and serially diluted in the normal growth media in a 96-well round bottom plate and then transferred to plate of cells. DMSO serves as the vector control up to 0.2% as final concentration. The cells are then incubated at 37° C. in a humidified 5% $CO_2$ incubator.

Four days following dosing of compound, the media is discarded and 200 µl/well of ice-cold 10% TCA (Trichloroacetic Acid) is added to fix cells. After 60 minutes at 4° C., the TCA is discarded and the plate is rinsed 5 times with water. The plate is then air-dried and 100 µl/well of 0.4% SRB (Sulforhodamine B from Sigma) in 1% Acetic Acid is added to stain cells for 10 minutes at room temperature. The SRB is discarded and the plate is rinsed 5 times with 1% Acetic Acid. After the plate is completely dried, 100 μl/well of 10 mM Tris-base is added to solubilize the dye. After 5 to 10 minutes, the plate is read on a Dynatech ELISA Plate Reader at dual wavelengths at 570 nm and 630 nm.

8. MCF-7/ HER-2 SRB Growth Assay

The protocol is basically the same as that above (for the MCF-7 Growth Assay) except that immediately before the compound is added, the normal growth media is removed and 0.5% FBS/RPMI supplemented with 2 mM Glutamine is added onto the cells. The compound is also prepared in this 0.5% serum media. The plate of cells is incubated for four days and developed as usual.

9. 3T3 Growth Assay

The 3T3 growth assay was carried out as follows:

Materials and Reagents (1) Dulbecco's Modified Eagle Medium (D-MEM), Gibco 11965-050;
(2) Calf serum, Gibco 16170-029;
(3) Trypsin-EDTA, Gibco 25200-056;
(4) Fetal Bovine Serum Certified, Gibco 16000-028;
(5) Dulbecco's Phosphate-Buffered Saline (D-PBS), Gibco 14190-029;
(6) Sulforhodamine B (SRB), Sigma S-9012. 0.4% SRB in 1% acetic acid;
(7) 10 mM Tris-base, Fisher BP152-5;
(8) 10 % TCA, Trichroloacetic acid, Fisher A322-500;
(9) 96-well flat bottom plate (sterile), Corning 08-757-155;
(10) 100 ml reagent reservoir 9 (sterile), Matrix Technologies Corporation, 8086;
(11) Sterile pipet tips, Fisher 21-197-8E;
(12) 50 ml sterile test tubes, Fisher 05-539-6.

Cell Lines

NIH3T3C7 cells in 10% CS+2 mM GLN DMEM
HER2C7 cells in 2% FBS+2 mM GLN DMEM

Procedures (1) HER2C7 (engineered to express HER2) and NIH3T3C7 (as the control) cells are used for this assay. NIH3T3C7 cells are seeded at 2500 cells/well, 10 μl/well in 10% CS+2 mM GLN DMEM, in a 96 well plate; HER2C7 cells are seeded at 6000 cells/well, 100 μl/well in 2% FBS+2 mM GLN DMEM, in a 96 well plate. Cells are incubated at 37° C., 5% $CO_2$ overnight to allow for cell attachment to the plate;

(2) The test compound is added to the cells at day 2. The compounds are prepared in the appropriate growth medium (10% CS+2 mM) GLN DMEM for NIH3T3C7 cells; 2% FBS+2 mM GLN DMEM for HER2C7 cells) in a 96 well plate, and serially diluted. A total of 100 μl/well medium of the diluted compounds is added into the cells. The total volume of each well is 200 μl. Quadruplicates (wells) and 11 concentration points are applied to each compound tested.

(3) After the cells are treated with the compound for 4 days, the cells are washed with PBS and fixed with 200 μl/well ice-cold 10% TCA for one hour at 0°–5° C. condition.

(4) Remove TCA and rinse wells 5 times with deionized water. Dry plates upside down with paper towels. Stain cells with 0.4% SRB at 100 μl/well for 10 minutes.

(5) Pour off SRB and rinse plate 5 times with 1% acetic acid. Dry plate completely.

(6) Solubilize the dye with 10 mM Tris-base at 100 μl/well for 10 minutes on a shaker.

(7) Read the plate at dual wavelengths at 570 nm and 630 nm on Dynatech Elisa plate reader.

B. Results

The effects of different compounds on EGFR, HER2 and PDGFR kinase activities are shown in Table V.

TABLE V

| | Estimated $IC_{50}$ (μM) | | | | | |
|---|---|---|---|---|---|---|
| | Cellular Kinase Assays | | | Growth Assays | | |
| Compound | EGFR (EGF-3T3) | HER2 (BT474) | PDGFR-β | SKBR3 cells | SKOV3 cells | A431 cells |
| M13 | >100 | 14 | 60 | 25 | 20 | |
| M15 | >100 | 16 | ~60 | 20 | 17 | |
| M11 | 40 | <3 | >100 | 4 | 0.5 | |
| M16 | 4 | 18 | 35 | 9 | 4.5 | |
| N10 | >100 | 20 | >100 | 78 | 85 | |
| P13a | 0.003 | 1.6 | | | | |
| P13b | 0.003 | 1.4 | | | | 10 |
| P12a | 0.04 | 7.14 | | | | 10 |
| P12b | 0.06 | 6.82 | | | | 20 |
| P10b | 0.16 | 34 | | | | 20 |
| P10a | 0.20 | 41 | | | | |
| P15 | 0.86 | >50 | | | | |
| M16 | 4.4 | 18.2 | | | | |
| M17 | 8.65 | 8.58 | | | | |
| R11 | 12.5 | 12.5 | | | | |
| M12 | 13.36 | >50 | | | | |
| P14b | 20.86 | >50 | | | | |
| P14a | 22.2 | >50 | | | | |
| M18 | 25 | 25 | | | | |
| R14 | 25 | 25 | | | | |
| R15 | 25 | >50 | | | | |
| R10 | 31.48 | >50 | | | | |
| R9 | 35.5 | 20.7 | | | | |
| M14 | 37.20 | >50 | | | | |
| M19 | >50 | 10.57 | | | | |
| Q11 | >50 | 11.05 | | | | |
| Q10 | 43 | 11.66 | | | | |
| N11 | >50 | 28.03 | | | | |
| M10 | >50 | 30.63 | | | | | nd refers to "not determined."

Table V shows compounds which significantly inhibits the cellular kinase activity HER2, EGFR and/or PDGFR. Such compounds were scored as "hits" in the initial cellular kinase screen. Additional compounds belonging to Groups I-IV were tested and found not to inhibit cellular kinase activity of a receptor with an $IC_{50}$ of less than 50 μM (data not shown). Using the described assay other compounds belonging to Group I-IV, able to significantly inhibit HER2, EGFR and/or PDGFR can be obtained. By analyzing the "hits" important functional groups can be identified thereby facilitating the design of additional compounds able to inhibit a receptor tyrosine kinase. Further testing and characterization can be carried out as described above, for example in the section regarding additional compounds.

Table VI provides cellular kinase assay data and cell growth data for Group 1 compounds. The cellular kinase assay data is shown in the columns labeled HER2BT474, EGFR-3T3, and E/HER2-3T3. The growth assays are shown in the columns marked MCF7-HER2, MCF7, 3T3-HER2 and 3T3. The data was obtained using procedures described above.

TABLE VI

| COMPOUND | HER2-BT474 | EGFR-3T3 | E/HER2-3T3 | MCF7-HER2 | MCF-7 | 3T3-HER2 | 3T3 |
|---|---|---|---|---|---|---|---|
| M9 | | | | | | | |
| M10 | 30.63 | >50 | | | | | |
| M11 | 3.1 | 21 | >100 | 0.2 | 4 | 30 | 75 |
| M12 | >50 | 13.4 | | | | | |
| M13 | 14 | >100 | >100 | | | | |
| M14 | >50 | 37.2 | | | | | |
| M15 | 16 | >100 | >100 | 6 | 15 | | |
| M16 | 26 | 9 | | | | | |
| M17 | 8.58 | 8.65 | | | | | |
| M20 | 3 | >100 | nt | 0.6 | 6 | 4 | 90 |
| M18 | 25 | 25 | | | | | |
| M19 | 10.57 | >50 | | | | | |
| M21 | 7.4 | >100 | >100 | 2 | 14 | 70 | >100 |
| M22 | 4.2 | >50 | >100 | 9 | 44 | | |
| M23 | 26 | 17 | | | | | |
| M24 | 3.1 | >50 | >100 | 1 | 8 | | |
| M25 | 3.1 | >100 | | | | | |
| M26 | 9.6 | >100 | >100 | 26 | 55 | >100 | >100 |
| M27 | 4.6 | >50 | >100 | 6 | 33 | 50 | >100 |
| M28 | 2.2 | nt | nt | 2 | 12 | | |
| M29 | 1.4 | >50 | >100 | 2 | 12 | 15 | >100 |
| M30 | 0.65 | 61 | 18.3 | 2 | 9 | 12 | 70 |
| M31 | 5.4 | >100 | >100 | 46 | >100 | >100 | >100 |
| M32 | 7.3 | 64 | >100 | >50 | | 80 | >100 |
| M33 | 0.17 | >100 | >100 | 0.05 | 1 | 9 | 35 |
| M34 | 0.11 | >100 | >100 | 0.06 | 2 | 5.5 | 40 |
| M35 | 0.29 | >100 | >100 | 0.09 | 0.3 | 0.25 | 18 |
| M36 | 0.4 | 56 | >100 | 2 | 8 | nt | nt |
| M37 | 0.85 | >100 | >100 | 1 | 3 | nt | nt |
| M38 | 14 | >100 | | >100 | >100 | | |
| M39 | 39 | 6.8 | | | | | |

Several compounds showed a positive result in the HER2BT474 assay, while showing little inhibition on the E/HER2-3T3 assay and showing significant inhibition in the HER2 growth assays. A possible explanation for this result is that the compounds are inhibiting HER2 kinase activity, but not autophosphorylation of HER2. these compounds may be acting by inhibiting HER2 transphosphorylation, for example HER2 transphosphorylation by HER4. The data also point out the ability of numerous Group 1 class 2 compounds to inhibit HER2 in a growth assay while having little effect on EGFR in a cellular kinase assay.

Example 2

Chemical Synthesis Examples of synthesis of exemplary compounds belonging to different groups and classes of compounds are described below.

Group I Compounds

M9

M9 was prepared as described by Gazit et al., *J. Med. Chem.* 34:1896 (1991).

M10

M10 was prepared as described by Gazit et al., *J. Med. Chem.* 34:1896 (1991).

M11

M11 was prepared as described by Ohmichi et al, supra. 3,5-Di-tert-butyl-4-hydroxybenzaldehyde (0.47 g, 2 mmol), 0.2 g (2.4 mmol) of thiocyanoacetamide and 30 mg of β-alanine in 40 mL of EtOH (ethanol) were refluxed for 6 hours. Water and HCl were added, and the reaction mixture was extracted with EtOAc (ethyl acetate). Evaporation gave 0.34 g (54% yield) of a yellow solid: mp 210° C.; NMR (acetone $d_6$) δ 8.47 (1 H, s, vinyl), 8.02 (2 H, s), 1.48 (18 H, s); MS m/e 316 ($M^+$, 100), 303 (35), 301 (99), 268 (16), 260-(M $(CH_3)_2$=C,45), 245 (17), 228 (22), 219 (52), 203 (10), 143 (11), 129 (11).

M12

M12 was prepared as described in Ohmichi et al., *Biochemistry* 32:4650 (1993) in two steps. First 3-methoxy-4-hydroxy-5-iodobenzylidene)malononitrile was prepared. To 1.4 g (5 mmol) of 5-iodovanillin and 0.4 g (6 mmol) of malononitrile in 25 mL of ethanol was added 3 drops of piperidine, and the reaction mixture was refluxed for 4 hours. Workup gave 0.8 g (49% yield) of a yellow solid: mp 188° C.; NMR ($CDCl_3$) δ 7.76 (1 H,J=1.8 Hz,$H_6$), 7.65 (1 H,d,J=1.8 Hz,$H_2$), 7.56 (1 H,s,vinyl), 6.85 (1 H,s,OH), 3.99 (3 H,s,$OCH_3$); MS m/e 327 (13), 326 ($M^+$,100) 283 (18), 128 (35), 101 (22).

Second 3-methoxy-4-hydroxy-5-iodobenzylidene) malononitrile (0.65 g, 2 mmol) and 0.6 mL (6 mmol) borontribromide ($BBr_3$) in 40 mL of $CH_2Cl_2$ were stirred under argon for 1 hour at room temperature. Water was added, and the reaction mixture was extracted with EtOAc to give 0.46 g (73% yield) of a light-red solid (yellow in solution) : mp 105° C.; NMR (acetone-$d_6$) δ 8.03 (1 H,s, vinyl), 7.88 (1 H,d,J=2.3 Hz,$H_2$), 7.72 (1 H,d,J=2.3 Hz,$H_6$) ; MS m/e 312 ($M^+$, 38), 254 (74), 185 (M-I,27), 158 (M-I-HCN,11), 157 (64), 130 (19), 129 (23), 127 (100)

M13

M13 was prepared as described by Ohmichi et al, supra. N-Benzylcyanoacetamide (1.05 g, 6 mmol) and 2.5 g of Lawson reagent in 40 mL of toluene were refluxed for 3 hours under $N_2$. Evaporation and chromatography gave 0.52 g (45% yield) of a white solid (N-Benzylcyanoacetamide): mp–87° C.; NMR ($CDCl_3$)δ 7.37 (5 H,m), 4.85 (2 H, d, J=7.0 Hz), 3.96 (2 H, s, $CH_2CN$) ; MS m/e 191 (24), 190 ($M^+$, 100).

N-Benzylcyanoacetamide (0.26 g, 1.4 mmol), 0.19 g (1.4 mM) of 3,4-dihydroxybenzaldehyde, and 15 mg of β-alanine in 30 mL of ethanol were refluxed for 4 hours. Workup (i.e., adding water to the reaction mixture and extracting it with CHCl₃ (or ethyl acetate for polar compounds) washing the organic phase to neutrality, drying on MgSO₄, filtering, and evaporating the phase to dryness) with ethyl acetate gave an oily solid. Trituration with $CH_2Cl_2/C_6H_6$ gave 0.27 g (64% yield) of a yellow solid (M13): mp–195° C.; NMR (acetone-d₆) δ 8.24 (1 H, s, vinyl), 7.69 (1 H, d, J=2.2 Hz, H₂), 7.45–7.28 (6 H, m), 6.93 (1 H. d, J =8.3 Hz, H₅) 5.06 (2 H, s, CH₂N) ; MS m/e 310 (M⁺, 25), 293 (M-OH, 35) 172 (M—SH—NHCH₂C₆H₅, 15), 123 (15), 106 (55), 91 (100).

M14

M14 was prepared as described by Birchall and Harney *Chem. Abst.* 88:535 (1978).

M15

M15 was synthesized in two steps. First, 3.2 g of 3-trifluoromethylaniline and 3 g of methyl cyanoacetate were heated at 100° C., under N₂, 18 hours. Chromatography on silica gel (elution with 2% CH₃OH in CH₂C₂) and trituration with benzene gave 0.88 g of N-3-trifluoromethylphenyl cyanoacetamide as a grey-white solid, mp 127° C. MS: 228 (M⁺, 56), 188 (M—CH₂CN, 19), 160 (M—COCH₂CN, 100). NMR CDCl₃ δ 7.84–7.50 (4 H,m), 3.60 (2 H, s, CH₂CN).

Second, 0.38 g, of N-3-trifluoromethylphenyl cyanoacetamide, 20 mg β-alanine and 0.22 g of 3,4-dihydroxybenzaldehyde were refluxed in 15 ml ethanol for 6 hours. Workup gave 0.52 g of M15 as a green-yellow solid, mp 250° C. NMR acetone d₆ δ 8.19 (1H, s, vinyl), 7.75 (1H, d, J=2.2 Hz, H₂), 7.46 (1H, dd, J=8.3, 2.2 Hz, H₆), 7.01 (1H, d, J=8.3 Hz, H₅), 8.24, 8.03, 7.61, 7.50 (4H). MS:-348 (M⁺, 68), 188 (CONHC₆H₄CF₃, 100), 161(90), 114(44).

M16

0.69 g, of 5-iodo vaniline, 0.5 g N-3-phenyl-n-propyl cyanoacetamide and 50 mg β-alanine in 30 ml ethanol were refluxed 5 hours. Evaporation gave an oil which was triturated with benzene-hexane and filtered to give 3-(4-hydroxyl-3-iodo-5-methoxyphenyl-2[(3-phenyl-n-propyl) aminocarbonyl acrylnitrile as a bright yellow solid (0.82 g, 71% yield, mp–83° C.). (3-methoxy 4 hydroxy 5-iodo α-cis cinnamone (3'phenyl propane) amide). (Should be kept solid and protected from light. Material in solution, 2 weeks at room light deteriorated partially.) NMR CDCl₃ δ 8.12(1H, S), 7.75(1H,d,J=2.0 Hz), 7.68 (1H,d,J=2.0 Hz), 7.30–7.10 (5H,m), 3.96 (3H,S,OCH₃), 3.45 (2H,q,J=6.0 Hz), 2.70 (2H,t,J=6.0 Hz), 1.95 (2H, quin, J=6.0 Hz). MS-462 (M⁺, 53), 357 (M—CH2)₃Ph,18), 335(M-I,100), 327(M—NH (CH₂), Ph, 31), m/e.

0.5 g 3-(4-hydroxyl-3-iodo-5-methoxyphenyl-2[(3-phenyl-n-propyl)aminocarbonyl acrylnitrile and 0.4 ml BBr₃, in 30 ml CH₂Cl₂ were stirred at room temperature 1.5 hours. Water was added and the reaction extracted with EtAc. Evaporation and trituration with benzene-hexane gave M16 as a light brown solid, 0.3 g, 63% yield, mp–184° C. NMR acetone d₆ δ 8.0(1H,S,vinyl), 7.88(1H,d, J=2.0 Hz), 7.66(1H,d,J=2.0 Hz), 7.30(5H,m,Ph), 3.42(2H,t,J=6.0 Hz), 2.70(2H,t,J=6.0 Hz), 1.96(2H, quin., J=6.0 Hz). MS-448(M⁺,3%), 321(M-I,8), 217(21), 201(33), 118(100), m/e.

M17

0.7 g, of 3,5-di-t-butyl-4-hydroxy-benzaldehyde, 0.46 g of 3-amino 4 cyano 5-cyanomethyl pyrazole (prepared according to Carboni et al., *J. Chem. Soc.*, 80:2838, 1958) and 40 mg β-alanine were refluxed in 10 ml ethanol 15 hours. Cooling and filtering gave 0.5 g, of M17, 46% yield, yellow solid, mp–255° C. NMR CDCl₃ δ 7.92(1H,S,vinyl), 7.80(2H,S), 5.76(1H,S,OH), 3.75(2H,br,S,NH₂), 1.48(18H, S). MS-364(M⁺1,28), 363(M₊, 100%), 348(M-CH₃,58), 292 (M-56-CH₃, 31), 147(41), m/e.

M18

0.7 g of 3,5-di-t-butyl-4-hydroxy-benzaldehyde, and 0.68 g of 1-phenyl-3-amino-4-cyano 5-pyrazole acetonitrile (prepared according to Carboni et al., *J. Chem. Soc.*, supra), and 40 mg β-alanine were refluxed 15 hours. Chromatography gave 0.27 g, 20% yield, yellow solid, mp–215° C. NMR CDCl₃ δ 8.02(1H,S,vinyl), 7.89(2H,S), 7.80–7.72(5H, m), 1.48(18H,S)

M19

18 g of 2,6-di isopropyl phenol and 1.8 g HMTA (hexamethylene tetraamine) in 60 ml TFA (trifluoro acetic acid) was refluxed 3.5 hours. Workup, chromatography on silica gel (CH₂Cl₂) and trituration with hexane gave 5.3 g, 26% yield, white solid, mp–103° C. (3,5,-di-iso-propyl 4 hydroxybenzaldehyde). NMR CDCl₃ δ 9.87(1H,S,CHO), 7.63(2H,S), 3.19(2H,septet,J=7.7 Hz), 1.30(12H,d,J=7.7 Hz).

0.4 g of 3,5,-diisopropyl-4-hydroxy benzaldehyde), 0.15 g of malononitrile and 3 drops piperidine in 30 ml ethanol were refluxed 3.5 hours. Workup and trituration with hexane gave 0.28 g, 56% yield, yellow solid, mp–150° C. NMR CDCl₃ δ 7.69(2H,S), 7.65(1H,S, vinyl), 3.16(2H,septet, J=7.0 Hz), 1.29(12H,d,J=7.0 Hz). MS-254(M⁺,59), 239(M-CH₃,95), 197(M-2CN₃—HCN, 100%), 149(25), m/e.

M20:(E)-3-(3, 5-di-t-butyl-4-hydroxyphenyl)-2-[(3-phenyl-n-propyl)aminocarbonyl]acrylonitrile M20 was prepared using 3,5-di-t-butyl-4-hydroxybenzaldehyde and N-3-phenyl-n-propyl cyanoacetamide under the similar conditions as desciбed for M21 infra.

M21: (E)-3-(3, 5-diisopropyl-4-hydroxyphenyl)-2-[(3-phenyl-n-propyl)aminocarbonyl]acrylonitrile A solution of 4.12 grams (20 mmole) of 3,5-diisopropyl-4-hydroxylbenzaldehyde and 4.24 grams (21 mmole) of N-(3-phenyl-n-propyl)cyanoacetamide was refluxed in 40 ml of ethanol for five hours. The mixture was then poured into 200 ml of diluted hydrochloric acid solution and extracted with methylene chloride (2×150 ml). The organic layer was then washed with water, 5% sodium bicarbonate solution, brine, dried over sodium sulfate, filtered and concentrated. The crude solid was then recrystallized from tolene to provide 5.4 grams (13.9 mmole, 69%) of M21 as light brown solid. The purity of this material is over 95% of HPLC and the structure confirmed by NMR, MS and IR.

M22: (E)-2-(1-amino-2, 2-dicyanoethenyl-3-(3,5-diisopropyl-4-hydroxyphenyl)acrylonitrile)

0.5 g, of 3,5-diisopropyl-4-hyrdroxybenzaldehyde, 0.35 g of malononitrile dimer and 30 mg β-alanine in 30 ml ethanol were refluxed 4 hours. Evaporation gave oily yellow solid. Trituration with acetone-hexane gave 25 mg yellow solid (M22), mp–209° C. Chromatography of mother liquid gave another 460 mg of M22.

M23: (E)-2-benzylaminocarbonyl-3-(3, 4-dihydroxy-5-iodophenyl)acrylonitrile)

a) 0.56 g of iodo vanilline, 0.38 g of N-benzylcyanoacetamide (Gazit et al, *J. Med. Chem.* 34:1896, 1991), and 40 mg β-alanine in 20 ml ethanol were refluxed hours. Cooling and filtering gave 0.72 g of the condensation product yellow solid, mp–204° C. NMR CDCl₃ δ8.19(1H,S,vinyl), 7.77(1H,d,J=1.8 Hz), 7.70(1H,d, J=1.8 Hz), 7.35(5H,m), 4.60(2H,d,J=6.0 Hz), 3.97(3H,S).

b) 0.4 g of the produce from step (a) and 0.5 ml BBr₃ in 20ml CH₂Cl₂ were stirred 2 hours at room temperature. Workup (H₂O, EtAc) gave 0.16 g of M23, yellow solid, mp–220° C. NMR acetone d₆ δ 8.05(1H,S,Vinyl), 7.85(1H, d,J=2.1 Hz), 7.70(1H,d,J=2.1 Hz), 7.30(5H,m), 4.6(2H,S).

M24: (E)-3-(3, 5-diisopropyl-4-hydroxyphenyl)-2-[(3-phenyl-n-propyl)aminothiocarbonyl]acrylonitrile 0.6 g of 3,5-diisopropyl-4-hydroxybenzaldehyde, and 0.6 g of N-3-phenyl-n-propylcyanothioacetamide and 40 mg β-alanine in 40 ml ethanol were refluxed 4 hours. Evaporation and chromatography gave 0.6 g of M24 as an orange viscous oil that did not crystalyze. NMR CDCl$_3$ δ8.76(1H, S,vinyl), 7.78 (2H,S,H$_{2,6}$) 7.25(5H,m), 5.60(1H,S,OH), 3.90 (2H,q,J=7.0 Hz), 3.17(2H,Septet, J=7.0 Hz), 2.76(2H,t, J=7.0 Hz), 2.11(2H, quintet, J=7.0 Hz), 1.29(12H,d,J=7.0 Hz). MS-407(M+1,55), 406(M+, 70), 373(M—CH3—H$_2$O, 100), 363 (M-isopropyl, 72), 272 (M–NH(CH$_2$)$_3$ Ph, 20), 259 (58), 230 (28), 91 (28), m/e.

M25 (E)-2-aminothiocarbonyl-3-(3, 5-diisopropyl-4-hydroxyphenyl)acrylonitrile

M25 was prepared using 3,5-diisopropyl-4-hydroxybenzaldehyde and cyanothioacetamide under similar conditions as described for M11.

M26: (E)-3-(3, 5-diisopropyl-4-hydroxyphenyl-2-[(-pyrid-2-yl)sulfonyl]acrylonitrile A solution of 450 mg (2.2 mmole) of 3,5-diisopropy-4-hydroxylbenzaldehyde and 400 mg (2.2 mmole) of 2-pyridinesulfonlyacetonitrile (Lancaster catalog number 7114) in 10 ml of ethanol was refluxed with few drop of piperidine for 3 hours. The reaction was then cooled to room temperature and added with about 5 ml of water until crystallization began. After standing at 0° C. for 2 hours, all the solid was collected and dried by suction filtration to provide 350 mg M26 (0.95 mmole, 43% yield) as an orange solid. The purity of this material is over 95% by HPLC and the structure confirmed by NMR, MS and IR.

M27: (E)-2-cyanomethylsulfonyl-3-(3, 5-diisopropyl-4-hydroxyphenyl)acrylonitrile)

A mixture of 500 mg of 3,5-diisopropyl-4-hydroxybenzaldehyde and 700 mg of sulfonyl diacetonitrile in 6 ml of ethanol was refluxed with a few drops of piperidine for 4 hours. Ethanol was removed in a rotavap and the mixture worked up with ethyl acetate, diluted acid and brine. A portion of the crude was then purified by HPLC on a C-18 column to provide 50 mg of M27 along with 30 mg of M29.

M28: (E)-3-(3, 5-diisopropyl-4-hydroxyphenyl)-2-[(4-trifluoromethyl)-phenylaminocarbonyl]acrylonitrile A mixture of 3.0 g of 3,5-diisopropyl-4-hydroxybenzaldehyde and 3.8 grams of N-4-trifluoromethylphenyl cyanoacetamide in 15 ml of ethanol containing 0.2 ml of piperidine was heated at 100° C. for 6 hours. The mixture was then cooled at 0° C. for 2 hours and the solid collected by filtration. The crude product was then further crystallized in ethanol and water to provide 3.6 grams of M28.

M29 (E,E)-2-[[1-cyano-2-(3, 5-diisopropyl-4-hydroxyphenyl) ethenyl]sulfonyl]-3-(3,5-diisopropyl-4-hydroxyphenyl)acrylonitrile)

M29 was obtained in the preparation of M27, as described above.

M30: (E)-3-(3, 5-diisopropyl-4-hydroxyphenyl)-2-(phenylsulfonyl)acrylonitrile)

M30 was prepared with 3,5-diisopropyl-4-hydroxybenzaldehyde and phenylsulfonyl acetonitrile under the similar conditions as described for M26.

M31: (E)-3-(3, 5-dimethyl-4-hydroxyphenyl)-2-(phenylsulfonyl)acrylonitrile)

M31 was prepared with 3,5-dimethyl-4-hydroxybenzaldehyde and phenylsulfonyl acetonitrile under similar conditions as described for M26.

M32: (E)-3-(3, 5-dimethyl-4-hydroxyphenyl)-2-[(pyrid-2-yl)sulfonyl]acrylonitrile)

M32 was prepared with 3,5-dimethyl-4-hydroxybenzaldehyde and (pyrid-2-yl)sulfonyl acetonitrile under similar conditions as described for M26.

M33: (E)-3-(3, 5-di-t-butyl-4-hydroxyphenyl)-2-(phenylsulfonyl)acrylonitrile

M33 was prepared with 3,5-di-t-butyl-4-hydroxybenzaldehyde and phenylsulfonly acetonitrile under similar conditions as described for M26.

M34: (E)-3-(3, 5-di-t-butyl-4-hydroxyphenyl)-2-[(pyrid-2-yl)sulfonyl]acrylonitrile M34 was prepared with 3,5-di-t-butyl-4-hydroxybenzaldehyde and (pyrid-2-yl)sulfonly acetonitrile under similar conditions as described for M26.

M35: (E)-3-(3, 5-di-t-butyl-4-hydroxyphenyl)-2-[(4-trifluoromethyl) phenylaminocarbonyl]acrylonitrile M35 was prepared with 3,5-di-t-butyl-4-hydroxybenzaldehyde and N-4-trifluoromethylphenyl cyanoacetamide under similar conditions as described for M28.

M36: (E)-3-(3, 5-di-t-butyl-4-hydroxyphenyl)-2-(cyanomethylsulfonyl)acrylonitrile M36 was prepared with 3,5-di-t-butyl-4-hydroxybenzaldehyde and sulfonyl diacetonitrile under similar conditions as described for M27.

M37: (E,E)-2-[[1-cyano-2-(3, 5-diisopropyl-4-hydroxyphenyl)ethenyl]sulfonyl]-3-(3,5-di- t-butyl-4-hydroxyphenyl)acrylonitrile M37 was obtained in the preparation of M36.

M38: (E,E)-[1-cyano-2-(3, 5-dimethyl-4-hydroxyphenyl) ethenyl]sulfonyl-(3, 5-dimethyl-4-hydroxyphenyl) acrylonitrile M38 was prepared with 3,5-dimethyl-4-hydroxybenzaldehyde and sulfonyl diacetonitrile under the similar conditions as described for M29.

M39 (E)-3-(3-hydroxy-4-nitrophenyl)-2-[(3-phenyl-n-propyl)aminocarbonyl]acrylonitrile M-39 was prepared with 3-hyroxy-4-nitro benzaldehyde and N-3-phenyl-n-propyl cyanoacetamide under similar conditions as described for M28.

M40: (E)-2-(benzylaminosulfonyl)-3-(3, 5-di-t-butyl-4-hydroxyphenyl)acrylonitrile)

A: To a solution of 2.14 g of benzylamine in 10 ml of ether at 5° C. was slowly added a solution of 1.37 g of cyanomethylsulfonylchloride [Sammes, et al., J. Chem. Soc. (C), 2151, 1971] in 5 ml of ether. The resulting mixture was then stirred for another 30 minutes, poured into 50 ml of water and extracted with 50 ml of ethyl acetate. The organic layer was then washed with brine, dried over magnesium sulfate, filtered and concentrated. The crude sulfonamide was then purified on a silica gel column (1:1 hexane/ethyl acetate) to provide 1.52 g of N-benzyl cyanomethylsulfonamide.

B: A mixture of 250 mg of 3,5-di-t-butyl-4-hydroxybenzaldehyde and 230 mg of N-benzyl cyanomethyl sulfonamide in 2 ml of ethanol with 2 drops of piperidine was heated at 100° C. for 3 hours. The cooled mixture was then diluted with 10 ml of water and extracted with 50 ml of ethyl acetate. The organic extract was then washed with brine, dried over sodium sulfate, filtered and concentrated. Crystallization of the crude with ethyl acetate and hexane yield 206 mg of M40.

M41: (E)-2-(benzylaminosulfonyl)-3-(3, 5-diisopropyl-4-hydroxyphenyl)acrylonitrile)

M41 was prepared with 3,5-diisopropyl-4-hydroxybenzaldehyde and N-benzyl cyanomethylsulfonamide under similar conditions as described for M40 (part B).

M42: (E)-2-(benzylaminosulfonyl)-3-(3, 5-dimethyl-4-hydroxyphenyl)acrylonitrile

M42 was prepared with 3,5-dimethyl-4-hydroxybenzaldehyde and N-benzyl cyanomethylsulfonamide under similar conditions as described for M40 (part B).

M43: (E)-3-(3, 5-di-t-butyl-4-hydroxyphenyl)-2-[(3-phenyl-n-propyl)aminosulfonyl]acrylonitrile)

A: N-3-Phenyl-n-propyl cyanomethylsulfonamide was prepared with 3-phenyl-n-propylamine and cyanomethylsulfonly chloride under similar conditions as described for N-benzyl cyanomethylsulfonamide (Part A, M40).

B: N-3-Phenyl-n-propyl cyanomethylsulfonamide and 3,5-di-t-butyl-4-hydroxybenzaldehyde was condensed under similar conditions as described for M40 (Part B) to yield M43.

M44: (E)-3-(3, 5-diisopropyl-4-hydroxyphenyl)-2-[(3-phenyl-n-propyl)aminosulfonyl]acrylonitrile M44 was prepared with 3,5-diisopropyl-4-hydroxybenzaldehyde and N-3-phenyl-n-propyl cyanomethylsulfonamide under similar conditions as described for M40.

M45: (E)-3-(3, 5-dimethyl-4-hydroxyphenyl)-2-[(3-phenyl-n-propyl)aminosulfonyl]acrylonitrile M45 was prepared with 3,5-dimethyl-4-hydroxybenzaldehyde and N-3-phenyl-n-propyl cyanomethylsulfonamide under similar conditions as described for M40 (part B).

GROUP II COMPOUNDS

N10

0.7 g of benzofurazone-l-oxide and 1 g, of benzoyl acetone in 10 ml $Et_3N$ (triethylamine) were stirred overnight at room temperature. After 1 hour a precipitate was formed. The mixture was stirred overnight at room temperature. Filtering and washing with methanol gave 0.67 g of N10 as a lemon yellow solid, mp-240° C. NMR $CDCl_3$ δ 8.7–8.6 (2H,m,$H_5$,8),7.9–7.5(7H,m) 2.52(3H,S). MS-280 ($M^+$, 60%), 248(M—$O_2$,35), 219(M—$H_2O$—$COCH_3$, 25), 187 (M—Ph—O, 30), 159(M—Ph—$COCH_3$, 100), m/e.

N11

N11 can be obtained from the ABIC, Isreali pharmaceutical company.

N16

0.7 g of benzofuroxane, 0.9 g of acetyl acetone and 10 ml $NH_3$, in 50 ml methanol were stirred 20 hours at room temperature. Workup and chromatography on silica gel (elution with $CH_2Cl_2$) gave 25 mg of N16 as a light yellow solid, mp 181° C. NMR $CDCl_3$ δ 8.60(2H,m), 8.31(1H,S, $H_2$) 7.85(2H,m), 2.62(3H,S). MS-176($M^+$, 100), 159(M—OH,15), 143 (M—OH—O,7), 129(M—$CH_3$—$O_2$,12), m/e.

N17

0.9 g of benzofuroxane, 0.9 g of phenyl acetone and 10 ml $NH_3$ in 30 ml methanol were stirred 20 hours at room temperature. Workup ($H_2O$,$CH_2Cl_2$) gave an oil. Trituration with hexane gave 0.33 g of N17, mp-195° C., light yellow solid. NMR $CDCl_3$ δ 8.66(2H,m), 7.85(2H,m), 7.50(5H,M), 2.50(3H,S). MS-252($M^+$,100%), 235(M—OH, 15), 218 (M—$CH_3$—OH, 45), 206(H—$O_2CH_2$, 15), 206(M—Ph—N—$O_2$—$CH_2$, 01⁺, 17), m/e.

N18

To 1.4 g of benzofuroxane and 1.1 g of methylcyanoacetate in 15 ml DMF (dimethylformamide) at 0° C. was to 1.2 g of DBU (diaza bicyclo [5.4.0] undec-7-ene). The color turned violet. After 10 minutes in the cold 50 ml $H_2O$ and 1 ml concentrated HCl was added. The solid was filtered to give 0.9 g of N18 as a deep yellow solid, mp-235° C. NMR $CDCl_3$ δ 7.45,m. (K. Ley and Seng, synth., supra)

N19

To 0.7 g of benzofuroxane and 0.3 g, 4.5 mM, malononitrile in 10 ml DMF at 0° C. was added 0.3 ml $Et_3N$. The color turned red. After 10 minutes in the cold and 1 hour at room temperature 60 ml $H_2O$ was added and the reaction filtered to give 0.5 g of N19 as a orange solid, mp-265° C. NMR DMSO $d_6$ δ 8.28–7.70, m. (Ley and Seng Synth. supra, reports a mp-232° C.).

N21

0.7 g of benzofuroxane, 1 g of α-chloro 3,4-dihydroxy acetophenone and 1 g of 3-phenyl propyl amine in 30 ml methanol were stirred at room temperature 1 hour. Filtering and washing with ethanol gave 0.96 g of N21 as a grey-white solid, mp-122° C. NMR acetone $d_6$ δ 7.47(2H,m), 7.20(9H, m), 6.88(1H,d,J=8.8 Hz, $H_5$), 4.86(S), 3.25(2H,t,J=7.0 Hz), 2.68(2H,t,J=7.0 Hz), 1.90(2H,quin. J=7.0 Hz). MS-186 (M—$O_2$—Ph—Ph$(OH)_2$, 15), 137(40), 118(100), 109(7), 91(50), m/e.

N22

0.7 g of benzofuroxane, 0.94 g of 2-chloro benzoyl acetonitrile and 10 ml $NH_3$ in 30 ml methanol were stirred 20 hours at room temperature. Workup ($H_2O$, $CH_2Cl_2$) and trituration with hexane gave 0.55 g of N22 as a yellow solid, mp-54° C. NMR $CDCl_3$ δ 7.50 m. MS-262(M—Cl, 100%), 246 (M—Cl—O, 55), 232(M—Cl—$NO_2$, 18), 204(22), m/e.

N23

0.7 g of benzofuroxane, 1.2 g of ethyl benzoyl acetate and 10 ml $NH_3$ in 30 ml methanol were stirred 20 hours at room temperature. Workup, chromatography on silica gel (3% $CH_2OH$ in $CH_2Cl_2$) and trituration with methanol gave 0.1 g of N23 as a yellow solid, mp-95° C. NMR $CDCl_3$ 8.66, 7.91(4H,AA'BB'm), 7.54(5H,m), 4.27(2H,q,J=7.0 Hz), 1.07 (3H,t,J=7.0 Hz).

N24

N24 can be prepared as described by Ley and Sing Synthesis, supra.

N25

0.35 g of N10, 90 mg of formaldehyde and 0.6 ml dimethyl amine (25% in water) in 30 ml methanol and 10 ml water were refluxed 2 hours. Workup ($H_2O$, $CH_2Cl_2$) and chromatography on silica gel (elution with 2% $CH_3OH$ in $CH_2Cl_2$) gave 0.1 g of N25 as a yellow solid, mp-122° C. NMR $CDCl_3$ δ 8.65(2H,m), 7.90(3H,m), 7.62(2H,m), 7.51 (2H,m) 3.12(2H,t,J=6.8 Hz), 2.70(2H,t,J=6.8 Hz), 2.08(6H, S,$CH_3$).

N26

1.4 g of benzofuroxane, 1.2 g of acetyl acetone and 10 ml $Et_3N$ in 20 ml methanol were stirred 24 hours at room temperature. Workup ($H_2O$,HCl, $CH_2Cl_2$) chromatography (elution with 2% $CH_3OH$ in $CH_2Cl_2$) and trituration with $CH_2Cl_2$-hexane gave 0.15 g of N26 as a yellow solid, mp 145° C. NMR $CDCl_3$ δ 8.60(2H,m), 7.90(2H,m), 2.74(3H, S,acetyl), 2.53(3H,S,$CH_3$). (C. H. Issidoredes, M. J. Haddadin J. Org. Chem., 31:4067 (1966), mp-154° C., 78%, NMR CDCl δ 8.48(2H,m), 7.76(2H,m), 2.66(3H,S), 2.45 (3H,S))

N27

1.5 g of benzofuroxane, 2.2 g of dibenzoyl methane and 1 g KOH in 40 ml methanol were stirred 2 hours at room temperature. Filtering and washing with methanol gave 2.2 g of N27 as a bright yellow solid, mp-243° C. (J. Org. Chem. supra, mp-234° C.) . NMR $CDCl_3$ δ 8.70(m), 7.94 (m), 7.80(m), 7.60(m), 7.4(m).

N28

0.5 g N27 and 1 g KOH in 15 ml methanol were heated 10 minutes at reflux, cooling and filtering gave 0.3 g of N28 as a yellow solid, mp-207° C. NMR $CDCl_3$ δ 8.75, 8.63 (2H,m, $H_{5,8}$), 8.50(1H,S,$H_2$), 7.90(4H,m,$H_{5,6}$⁺Ph), 7.56(3H, m). (J. Organic Chem., supra mp-204° C.).

GROUP III COMPOUNDS 4-chloro quinazoline 4.6 g of 4-quinazolinone, 5 ml phosphorochloride ($POCl_3$) and 5 ml dimethyl aniline in 50 ml toluene were refluxed 3.5 hours. Workup (NH$_3$, H$_2$O, EtAc) gave green oil. Chromatography on silica gel (CH$_2$Cl$_2$) gave 1.48 g of 4-chloro quinazoline as a light brown solid, mp–83° C., 29% yield. NMR CDCl$_3$ δ 9.05(1H,S), 8.27(1H,m), 8.1–7.9 (2H, m) 7.75(1H,m).

P10a and P10b a) 0.73 g of 4-chloro quinazoline and 0.58 g of 3-chloroaniline in 20 ml ethanol were refluxed 0.5 hour. Cooling and filtering gave 0.83 g of P10a (HCl salt) as a, bright-yellow solid mp–240° C.

b) 400 mg P10a was treated with Na$_2$CO$_3$ —H$_2$O and extracted with CH$_2$Cl$_2$. Evaporation gave 0.28 g of P10a as a green-white solid, mp–198° C., the free base. NMR CDCl$_3$ δ8.82(1H,S), 7.97–7.80(4H,m), 7.59(2H,m), 7.35(1H,t,J= 8.3 Hz), 7.15(1H,m).

6-methyl 4-guinazolinone 8 g of 5-methyl 2-aminobenzoic acid and 15 ml formamide was heated at 170° C. 1.5 hour. Water was added and the solid filtered to give 7.3 g of 6-methyl 4-quinazolinone as a light brown-white solid, mp–268° C.

8-methyl 4-quinazolinone 6 g of 2-amino 3 methyl benzoic acid and 8 ml formamide were heated at 170° C. for 1.5 hours. Water was added and solid filtered to provide 4.6 g of 8-methyl 4-quinazolinone as a white solid, mp–260° C. NMR acetone d$_6$ δ 8.14(1H,br,S), 8.06(1H,m), 7.66(1H,m), 7.38(1H,m), 2.58(3H,S).

8-methyl 4 chloro quinazoline 4 g of 8-methyl 4-quinazolinone, 5 ml POCl$_3$ and 5 ml dimethyl aniline in 40 ml toluene were refluxed 3.5 hours. Workup and trituration with hexane gave 2.6 g of 8-methyl 4 chloro quinazoline, mp–122° C. NMR CDCl$_3$ δ 9.07(1H, S), 8.12(1H,d,J=7.7 Hz), 7.8(1H,d,J=6.0 Hz), 7.60(1H,t), 2.78(3H,S).

P11a and P11b a) 0.9 g of 8-methyl 4-chloro quinazoline, and 0.7 g of m-chloroaniline in 20 ml ethanol were refluxed 0.5 hours. Cooling and filtering gave 1 g of P11a (HCl salt) as a white solid, mp–222° C. Insoluble in H$_2$O, EtOH, CH$_2$Cl$_2$ or acetone.

b) 0.5 g P11a gave (i.e., treatment with aqueous Na$_2$CO$_3$ and extracting with CH$_2$Cl$_2$) 0.16 g of P11b as a white solid mp–195° C. NMR CDCl$_3$ δ 8.87(1H,S), 7.96(1H,t,J=1.8 Hz), 7.75–7.40(4H,m), 7.34(1H,t,J=7.7 Hz), 7.15(1H,m), 2.75(3H,S).

P12a and P12b a) 0.39 g of 4-chloro-6-methyl quinazoline, and 0.29 g of m-chloroaniline were refluxed 0.5 hours. Cooling and filtering gave 0.44 g of P12a (HCl salt) as a white solid, mp–245° C.

0.32 g of P12a (Na$_2$CO$_3$, H$_2$O, CH$_2$Cl$_2$) gave 0.2 g of P12b as a white solid, mp–210° C. NMR CDCl$_3$ δ 8.78(1H, S), 7.96(1H,br,S), 7.85(1H,d,J=9.2 Hz), 7.60(3H,m), 7.34 (1H,t,J=8.0 Hz), 7.14(1H,m), 2.58(3H,S).

P13a and P13b a) 0.4 g of 4-chloro 6,7-dimethoxy quinazoline and 0.24 g m-chloro aniline in 10 ml ethanol were refluxed 0.5 hours. Cooling and filtering gave 0.52 g of P13a (HCl salt) as a white solid (P13a), mp–270° C.

b) 0.4 g of P13a gave (Na$_2$CO$_3$,H$_2$O,CH$_2$Cl$_2$), 70 mg of P13b as a white solid, mp–177° C. NMR CDCl$_3$ δ 8.68(1H, S), 7.83(1H,S), 7.5–7.1(5H,S) 4.0(6H,S).

P14a and P14b a) 0.45 g of 4-chloro 6-methyl quinazoline and 0.35 g of 3,4-methylenedioxy aniline were refluxed in 25 ml ethanol 0.5 hour. Cooling and filtering gave P14a (HCl salt) as a light green solid (P14a) 0.61 g, mp–255 ° C.

0.4 g P14a gave (Na$_2$CO$_3$,H$_2$O,CH$_2$Cl$_2$) 0.21 g P14b as a light brown solid, mp–203° C. NMR CDCl$_3$ δ 8.68 (1H,S, H,) 7.80(1H,d,J=8.8 Hz,H$_8$), 7.60(2H,m), 7.35(1H,m) 6.95 (1H,dd,J=8.8,2.5 Hz, H$_7$), 6.81(1H,d,J=8.2 Hz,H$_5$') 6.0(2H, S), 2.54(3H,S)

P15

0.45 g of 4-chloro 6-methyl quinazolone and 0.405 g, of m-trifluoromethylaniline in 20 ml ethanol were refluxed 1 hour. Treatment with aqueous Na$_2$CO$_3$ and extraction with CH$_2$Cl$_2$ gave 0.2 g of P15 as a white solid, mp–215° C., as the free base. NMR CDCl$_3$ δ 8.78(1H,S), 8.06(2H,m), 7.86(1H,d,J=7.6 Hz), 7.65(2H,m), 7.54(1H,t,J=8.0 Hz), 7.42 (1H,m), 2.58(3H,S).

GROUP IV COMPOUNDS

Q10

0.7 g of 2,5-dihydroxy benzaldehyde and 0.75 g of 3-amino methyl benzoate in 40 ml methanol were refluxed 3 hours, cooled, and 0.5 g sodiumcyanoborohydride (NaCNBH$_4$) were added. After 12 hours at room temperature workup (H$_2$O, EtAc) and chromatography (silica gel, elution with 5% CH$_3$OH in CH$_2$Cl$_2$) gave 0.42 of Q10 as a light yellow solid, mp 175° C. NMR acetone-d$_6$ δ 7.78, 6.68 (4H, ABq, J$_{AB}$=8.8 Hz), 6.74 (1H, d, J=3.0 Hz,H$_6$), 6.72 (1H, d, J=8.5 Hz,H$_3$), 6.55 (1H, d, J=8.5, 3.0 Hz,H$_4$), 4.34 (2H, s, CH$_2$N), 3.76 (3H, s, COOCH$_3$)

Q11

To 4 g m-chloro-aniline in 20 ml HCl and 20 ml H$_2$O, cooled in ice, was added 2.4 g sodium nitrite (NaNO$_2$) during 0.5 hours. Then it was added into solution of 2.2 g malononitrile and 10 g potassium acetate (KA)c in 100 ml ethanol. After 0.5 hours in the cold and 1 hour at room temperature the solid was filtered, washed with water and dried to give 2.4 g of Q11 as a yellow solid, mp–170° C. NMR CDCl$_3$ δ 7.4–7.2, m.

OTHER COMPOUNDS

N29

0.5 g N27 and 2 g sodium dithionit in 15 ml H$_2$O and 15 ml methanol were heated at 100° C. for 20 minutes. Cooling and filtering followed by TLC, chromatography on silica gel (2% CH$_3$OH in CH$_2$Cl$_2$ produce N29, 0.05 g 10% yield, mp–130° C. NMR CDCl$_3$ δ 8.60(1H,m), 8.25(1H,m), 7.8–7.4(12H,m)

Trimethylene 1,3-bis acetamide 2.2 g 30 mM, 1,3 diaminopropane and 5.4 g 60 mM, methyl cyano acetate were stirred one hour at room temperature. Trituration with ethanol and filtering gave 4.0 g, 74% yield, white solid, mp–148° C. MS-208(M$^+$,22%) 140(10%), 125(17%), 111(100%), 72(20%), m/e.

R9 and R13

To 5 g of 1-phenyl-1,2-dioxo-propane in 40 ml CHCl$_3$ was added dropwise 2.1 ml, 40 mM, or bromine. After 4 hours at room temperature workup (H$_2$O, thiosulphate, CH$_2$Cl$_2$) gave 4.9 g, 64%, yellow oil, 95% pure (3-bromo-1,2-dioxo-1-phenyl-propane). NMR CDCl$_3$ δ 8.04(2H,m), 7.65 (3H,m), 4.39(2H,S). R9: To 4.9 g of the above 3-bromo-1, 2-dioxo-1-phenyl-propane in 20 ml cold ethanol was added 2.93 g of 4,5 dimethylphenylene diamine. After 10 minutes the reaction was filtered to give 3.7 g of R9 as a white solid, mp–144° C. NMR CDCl$_3$ δ 7.88(2H,br. S), 7.70(2H,m), 7.5(3H,m), 4.73(2H,S, CH$_2$Br), 2.51(6H,S, CH$_3$).

R13: 0.4 g of 4,5-dimethyl phenylene diamine and 0.44 g of 1,2-dioxo-1-phenyl-propane in 20 ml ethanol were refluxed two hours. Cooling and filtering gave 0.6 g of R13 as a white solid mp–98° C. NMR CDCl$_3$ δ 7.84(1H,S), 7.78(1H,S), 7.60 (2H,m), 7.45(3H,m), 2.73(3H,S,CH$_3$ at position 2), 2.48(3H,S), 2.46(3H,S).

R10

0.3 g of 3.4-dihydroxy 5-bromo benzaldehyde, 0.15 g, of bis-cyanoacetamide, and 25 mg β-alanine in 20 ml ethanol were refluxed 3 hours. Cooling and filtering gave 0.24 g, 57% yield, yellow solid, mp–283° C.

R11

0.33 g of R9, 0.08 g of 1,3-propane dithiol and 0.1 g postassium hydroxide (KOH), in 25 ml ethanol were stirred 24 hours at room temperature. Workup ($H_2O$, $CH_2Cl_2$) and trituration with hexane gave 0.18 g of R11 as a white solid, mp–165° C. NMR $CDCl_3$ δ 7.85(2H,S), 7.82(2H,S) 7.70 (4H,m), 7.48(6H,m), 3.96(4H,S), 2.61(4H,t,J=7.6 Hz).

R12

To 0.7 g of benzofuroxane and 1.2 g KOH in 20 ml $H_2O$ and 20 ml methanol was added 1.2 g of N-1-phenyl-n-propyl-cyanoacetamide. The color turned black-violet and then brown. After 1 hour at room temperature 1 ml HCl (concentrated) was added. Filtering gave 0.38 g of R12 as a yellow-brown solid (mp 1650). NMR $CDCl_3$ δ 7.82, 7.48 (4H,AA'BB'm), 7.20(5H,m), 3.54(2H,q,J=7.0 Hz), 2.76(2H, t,J=7.0 Hz), 2.01(2H,quin,J=7.0 Hz). MS-311 ($M^+$, 10), 295(M—O,8), 278(M—O—OH, 11), 207(15), 145(18), 91(100), m/e.

R14

1.8 g of 4,5-dichloro 1,2-phenylene diamine and 1.5 g of phenyl glyoxal hydrate in 30 ml ethanol were refluxed 2 hours. Cooling and filtering gave 2.2 g light violet solid. Evaporation and chromatography of the mother liquid gave 0.2 g of R14 as white solid, mp–155° C. Overall yield—866. NMR $CDCl_3$ δ 9.32(1H,S,$H_2$), 8.28(1H,br.S), 8.24(1H,br.S), 8.18(2H,m), 7.58(3H,m).

R15

0.92 of Ninhydrin and 0.68 g of 4,5-dimethyl 1,2-phenylene diamine in 20 ml ethanol were refluxed 1.5 hours. Cooling and filtering gave 1.1 g of R15 as a yellow solid, mp–256° C. NMR $CDCl_3$ δ 8.05–7.50(6H,m), 2.47(3H,S), 2.46(3H,S).

Other embodiments are within the following claims.

We claim:

1. A compound having the chemical formula:

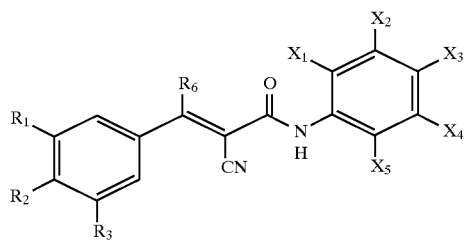

or a pharmaceutically acceptable salt thereof, wherein $R_1$, $R_2$, and $R_3$ are each independently selected from the group consisting of alkyl, alkenyl, alkynyl, alkoxy, alkylaryl, halogen, hydrogen, OH, amine, thioether, SH and $NH_2$;

$R_6$ is selected from the group consisting of alkyl, alkenyl, alkynyl, alkylaryl, halogen, hydrogen, amine, thioether, SH and $NH_2$; and $X_1$, $X_2$, $X_3$, $X_4$, and $X_5$ are each independently selected from the group consisting of hydrogen, halogen, trihalomethyl, alkyl, alkenyl, alkynyl, alkoxy, and $NO_2$, provided that at least one of $X_1$, $X_2$, $X_3$, $X_4$, and $X_5$ is a trihalomethyl.

2. The compound of claim 1, wherein $R_2$ is OH, $R_6$ is hydrogen, and four of $X_1$, $X_2$, $X_3$, $X_4$, and $X_5$ are hydrogen.

3. The compound of claim 1, wherein said compound inhibits HER-2 activity.

4. A compound having the chemical formula:

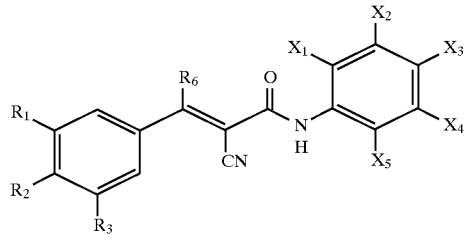

or a pharmaceutically acceptable salt thereof, wherein $R_1$, $R_2$, and $R_3$ are each independently selected from the group consisting of alkyl, alkenyl, alkynyl, alkoxy, alkylaryl, halogen, hydrogen, OH, amine, thioether, SH and $NH_2$;

$R_6$ is hydrogen; and $X_1$, $X_2$, $X_3$, $X_4$, and $X_5$ are each independently selected from the group consisting of hydrogen, halogen, trihalomethyl, alkyl, alkenyl, alkynyl, alkoxy, and $NO_2$, provided that at least one of $X_1$, $X_2$, $X_3$, $X_4$, and $X_5$ is a trihalomethyl.

5. The compound of claim 4, wherein $R_2$ is OH and four of $X_1$, $X_2$, $X_3$, $X_4$, and $X_5$ are hydrogen.

6. The compound of claim 4, wherein $R_1$ and $R_3$ are alkyl.

7. The compound of claim 4, wherein said compound inhibits HER-2 activity.

8. The compound of claim 4, wherein said compound is either (E)-3-(3,5-diisopropyl-4-hydroxyphenyl)-2-[(4-trifluoromethyl) phenylaminocarbonyl]acrylonitrile or (E)-3-(3,4-dihydroxyphenyl)-2-[(3-trifluoromethyl) phenylaminocarbonyl]acrylonitrile.

9. The compound (E)-3-(3,5-diisopropyl-4-hydroxyphenyl)-2-[(4-trifluoromethyl) phenylaminocarbonyl]acrylonitrile or a pharmaceutically acceptable salt thereof.

10. A pharmaceutical composition, comprising a therapeutically effective amount of a compound of any one of claims 1–9 and a pharmaceutically acceptable carrier or excipient.

11. A method of treating a patient having a cell proliferative disorder, wherein the disorder is sensitive to treatment by a compound of any one of claims 1–9, comprising administering to said patient a therapeutically effective amount of a compound of any one of claims 1–9.

12. The method of claim 11, wherein said disorder is characterized by inappropriate activity of EGFR.

13. The method of claim 11, wherein said cell proliferative disorder is a cancer.

14. The method of claim 13, wherein said cancer is selected from the group consisting of breast carcinomas, stomach adenocarcinomas, salivary gland adenocarcinomas, endometrial cancers, ovarian adenocarcinomas, gastric cancers, colorectal cancers, and glioblastomas.

15. The method of claim 14, wherein said cancer is a breast carcinoma.

16. A method of treating a patient having a cancer characterized by over-activity of HER2, wherein said cancer is sensitive to treatment by a compound of any one of claims 1–9, comprising administering to said patient a therapeutically effective amount of a compound of any one of claims 1–9.

17. A method of treating a patient having a cancer characterized by inappropriate activity of EGFR, wherein said cancer is sensitive to treatment by a compound of any one of claims 1–9, comprising administering to said patient a therapeutically effective amount of a compound of any one of claims 1–9.

* * * * *